(12) United States Patent
Katagiri

(10) Patent No.: US 6,852,498 B2
(45) Date of Patent: Feb. 8, 2005

(54) OOMYCETE FTSZ-MT AS A TARGET FOR OOMYCETE-SPECIFIC ANTIMICROBIALS

(75) Inventor: Fumiaki Katagiri, San Diego, CA (US)

(73) Assignee: Syngenta Participations AG, Basel (CH)

(*) Notice: Subject to any disclaimer, the term of this patent is extended or adjusted under 35 U.S.C. 154(b) by 160 days.

(21) Appl. No.: 09/770,509

(22) Filed: Jan. 25, 2001

(65) Prior Publication Data

US 2003/0082657 A1 May 1, 2003

(51) Int. Cl.[7] .............................................. G01N 33/53
(52) U.S. Cl. ........................................ 435/7.8; 435/7.1
(58) Field of Search ............................. 435/6, 7.1, 7.2, 435/7.8

(56) References Cited

U.S. PATENT DOCUMENTS 5,981,836 A  11/1999  Osteryoung ................. 800/278
6,197,300 B1 *  3/2001  Fueyo et al. ............. 424/185.1

OTHER PUBLICATIONS

Desnottes, Trends in Biotechnology, vol. 14 pp. 134–140 (1996).*

Berendsen, Science vol. 282, pp. 642–643 (1998).*

Beech et al., Mitochondrial FtsZ in a Chromophyte Alga, Science, 287:1276–1279 (2000), Database Entry Q9M7M6.

Beech et al., "FtsZ and Organelle Division in Protists", Protist, 151: 11–16 (2000).

Kamoun et al., "Initial assessment of gene diversity for the oomycete pathogen Phytophthora infestans based on expressed sequences," Fungal Genet. Biol., 28: 94–106 (1999), Database Entry BE777302.

Margolin, William, "Organelle division: Self–assembling GTPases caught in the middle", Current Biology, 10: R328–R330 (2000).

Beech et al., "Mitochondrial FtsZ in a Chromophyte Alga," Science, vol. pp. 1276–1279, Feb. 18, 2000.

* cited by examiner

Primary Examiner—Terry Mckelvey
Assistant Examiner—Nancy T. Vogel
(74) Attorney, Agent, or Firm—Mary Kakefuda

(57) ABSTRACT

The invention relates to a genes isolated from an oomycete that encode homologs of an FtsZ protein. The invention includes methods of using these proteins to discover new antimicrobials, based on the essentiality of the gene for normal growth and development. The invention can also be used in screening assays to identify inhibitors that are potential antimicrobials. These antimicrobials may be used in a method of controlling oomycete growth on crop plants and seeds.

4 Claims, 11 Drawing Sheets

FtsZ-mt2 consensus2 Map.MPD (1 > 1423) Site and Sequence  Page 1
Enzymes: 50 of 502 enzymes (Filtered)
Settings: Circular, Certain Sites Only, Standard Genetic Code

```
             EcoRV
               |
GATGGCGATATCCCGCATGAAAGCTGCGGCGATGGCGCTGCTACGTGCCCGCCAGACCTCCCAGTCCGCCACTCA
CTACCGCTATAGGGCGTACTTTCGACGCCGCTACCGCGACGATGCACGGGCGGTCTGGAGGGTCAGGCGGTGAGT  75

Met Ala Ile Ser Arg Met Lys Ala Ala Ala Met Ala Leu Leu Arg Ala Arg Gln Thr Ser Gln Ser Ala Thr Gln
                                       Pst I
                                       | Pvu II                           Taq I
                                       ||                                   |
ACACCTCGCCTTCTCTACTGAAGCCACTGATGCTGCAGCTGCCGCGGTTACGCATGGGCTTTAAAAAGGCTCGAAA
TGTGGAGCGGAAGAGATGACTTCGGTGACTACGACGTCGACGGCGCAATGCGTACCCGAAATTTTTCCGAGCTTT  150

His Leu Ala Phe Ser Thr Glu Ala Thr Asp Ala Ala Ala Ala Ala Leu Arg Met Gly Phe Lys Lys Ala Arg Lys

Taq I
                                                                             |
AGACGAGGATGGCGGTGTGAAAGTGGGGCTGGAGGCAGAGCCCGATTCACCAACAGATGTGAGCGCCGTTTCGAC
TCTGCTCCTACCGCCACACTTTCACCCCGACCTCCGTCTCGGGCTAAGTGGTTGTCTACACTCGCGGCAAAGCTG  225

Asp Glu Asp Gly Gly Val Lys Val Gly Leu Glu Ala Glu Pro Asp Ser Pro Thr Asp Val Ser Ala Val Ser Thr

Sac I
                                     |
GCCAGTAGTAGAGAAGAAGCTCGTGCCGCCAGCCATGAGCTCCACACAGCCACTTTGGCTCACACAGGACCATCC
CGGTCATCATCTCTTCTTCGAGCACGGCGGTCGGTACTCGAGGTGTGTCGGTGAAACCGAGTGTGTCCTGGTAGG  300

Pro Val Val Glu Lys Lys Leu Val Pro Pro Ala Met Ser Ser Thr Gln Pro Leu Trp Leu Thr Gln Asp His Pro

TGTGACAGACCTGTCGGGCTTTGCACCGAAGATTGTGGTGGTTGGCGTCGGAGGAGCTGGAGGAAATGCGGTGAA
ACACTGTCTGGACAGCCCGAAACGTGGCTTCTAACACCACCAACCGCAGCCTCCTCGACCTCCTTTACGCCACTT  375

Val Thr Asp Leu Ser Gly Phe Ala Pro Lys Ile Val Val Val Gly Val Gly Gly Ala Gly Gly Asn Ala Val Asn
```

FIGURE 1A

Page 2

FtsZ-mt2 consensus2 Map.MPD (1 > 1423) Site and Sequence

```
     Sau3A
     | BssH II    Pst I                          Blp I
     |  |          |                              |
CAACATGATCGCGCGCGGCCTGCAGGGTGTGGAGTTTCTTGTTTGCAACACGGATGCTCAGCACTTACGCACGAC
GTTGTACTAGCGCGCGCCGGACGTCCCACACCTCAAAGAACAAACGTTGTGCCTACGAGTCGTGAATGCGTGCTG   450

Asn Met Ile Ala Arg Gly Leu Gln Gly Val Glu Phe Leu Val Cys Asn Thr Asp Ala Gln His Leu Arg Thr Thr

GCTGACGGAGAACCGCGTTCAGATGGCTCCTGAATTGACTGGAGGACTGGGCTGTGGCGCTAACCCCGAAGTTGG
CGACTGCCTCTTGGCGCAAGTCTACCGAGGACTTAACTGACCTCCTGACCCGACACCGCGATTGGGGCTTCAACC   525

Leu Thr Glu Asn Arg Val Gln Met Ala Pro Glu Leu Thr Gly Gly Leu Gly Cys Gly Ala Asn Pro Glu Val Gly

CCGAGAGGCGGCAGAGGCCGCGATTGATGAGATTTTGGAGCGCGTTCAGGGTGCAAACATGATGTTTGTTACTGC
GGCTCTCCGCCGTCTCCGGCGCTAACTACTCTAAAACCTCGCGCAAGTCCCACGTTTGTACTACAAACAATGACG   600

Arg Glu Ala Ala Glu Ala Ala Ile Asp Glu Ile Leu Glu Arg Val Gln Gly Ala Asn Met Met Phe Val Thr Ala

Sac I
                                      |
GGGTATGGGTGGCGGAACAGGTACAGGTGCAGCACCCGTCATTGCTCAGGCTGCCTTAGATGCTGGTATCCTCAC
CCCATACCCACCGCCTTGTCCATGTCCACGTCGTGGGCAGTAACGAGTCCGACGGAATCTACGACCATAGGAGTG   675

Gly Met Gly Gly Gly Thr Gly Thr Gly Ala Ala Pro Val Ile Ala Gln Ala Ala Leu Asp Ala Gly Ile Leu Thr

CGTAGCTGTCGTTACTAAGCCGTTCCGGTTTGAGGGAAACAACCGTGCAAAGCTTGCGGCACAAGGCCTCGCTGA
GCATCGACAGCAATGATTCGGCAAGGCCAAACTCCCTTTGTTGGCACGTTTCGAACGCCGTGTTCCGGAGCGACT   750

Val Ala Val Val Thr Lys Pro Phe Arg Phe Glu Gly Asn Asn Arg Ala Lys Leu Ala Ala Gln Gly Leu Ala Glu

Sac I
                                      |
ACTGAAGGATAGCGTCGATACGATGCTTGTGATCCCGAACCAAAACTTGTTCAACATGTCAAATGAGCGCACCTC
TGACTTCCTATCGCAGCTATGCTACGAACACTAGGGCTTGGTTTTGAACAAGTTGTACAGTTTACTCGCGTGGAG   825

Leu Lys Asp Ser Val Asp Thr Met Leu Val Ile Pro Asn Gln Asn Leu Phe Asn Met Ser Asn Glu Arg Thr Ser
```

FIGURE 1B

Page 3

FtsZ-mt2 consensus2 Map.MPD (1 > 1423)  Site and Sequence

```
GTTGATGGACGCATTCAGAATGGCGGACAATGTGCTTCTGGACGGTGTCAAGAACATTTCGGATTTGATGGTGAT
CAACTACCTGCGTAAGTCTTACCGCCTGTTACACGAAGACCTGCCACAGTTCTTGTAAAGCCTAAACTACCACTA  900

Leu Met Asp Ala Phe Arg Met Ala Asp Asn Val Leu Leu Asp Gly Val Lys Asn Ile Ser Asp Leu Met Val Met

GCCTGGGCTCATTAACCTTGACTTTGCGGATGTTCAATCGGTCATGCAAAATATGGGAAACGCTATGATGGGAAG
CGGACCCGAGTAATTGGAACTGAAACGCCTACAAGTTAGCCAGTACGTTTTATACCCTTTGCGATACTACCCTTC  975

Pro Gly Leu Ile Asn Leu Asp Phe Ala Asp Val Gln Ser Val Met Gln Asn Met Gly Asn Ala Met Met Gly Ser

Nal I
                                                       |
TGGAGAGGCCGATGGAGAGAATCGGGCTCTGCGTGCTGCTGAAGATGCATTGGCGAACCCTCTTCTGGGTGATAT
ACCTCTCCGGCTACCTCTCTTAGCCCGAGACGCACGACGACTTCTACGTAACCGCTTGGGAGAAGACCCACTATA  1050

Gly Glu Ala Asp Gly Glu Asn Arg Ala Leu Arg Ala Ala Glu Asp Ala Leu Ala Asn Pro Leu Leu Gly Asp Ile

Taq I                              Sau3A I
      |                                  |
TTCGATTAAGGACGCCAAGGGCATGATCGTTAATATCACGGGAGGCTCCGACCTGACGCTATTTGAAGTTGATCA
AAGCTAATTCCTGCGGTTCCCGTACTAGCAATTATAGTGCCCTCCGAGGCTGGACTGCGATAAACTTCAACTACT  1125

Ser Ile Lys Asp Ala Lys Gly Met Ile Val Asn Ile Thr Gly Gly Ser Asp Leu Thr Leu Phe Glu Val Asp Glu

Bip I              Sau3A I                    Taq I Taq I
     |                   |                          |     |
GGCTGCTGAGCGTGTGACGCGGGAACTTGATGATCCACACGCCAACATCATCTTCGGTTCGACCTTCGACGACTC
CCGACGACTCGCACACTGCGCCCTTGAACTACTAGGTGTGCGGTTGTAGTAGAAGCCAAGCTGGAAGCTGCTGAG  1200

Ala Ala Glu Arg Val Thr Arg Glu Leu Asp Asp Pro His Ala Asn Ile Ile Phe Gly Ser Thr Phe Asp Asp Ser
                        Afl III
                        Mlu I
                         |
GCTGGGCGGCAAGCTACGCGTCTCCGTGGTTGCCACTGGTATTGCCGACCCCGACAAGTTATAGAAGCCGTGATG
CGACCCGCCGTTCGATGCGCAGAGGCACCAACGGTGACCATAACGGCTGGGGCTGTTCAATATCTTCGGCACTAC  1275

Leu Gly Gly Lys Leu Arg Val Ser Val Val Ala Thr Gly Ile Ala Asp Pro Asp Lys Leu  *
```

FIGURE 1C

Page 4

FtsZ-mt2 consensus2 Map.MPD (1> 1423)  Site and Sequence
___

TTGGCCAGTATCAAAGCGTAAGCAGGGGAATGACACCTAATGACGTGATTGCTCAAGAAATCTCTACAATTTGAA
AACCGGTCATAGTTTCGCATTCGTCCCCTTACTGTGGATTACTGCACTAACGAGTTCTTTAGAGATGTTAAACTT  1350

```
    Cla I
    Taq I              Sau3A I
```
GTGGCATCGATGTCTCCACGCACCCGCGCGTGCTGATCGGATTGGTATTATACGGACTGCTTCATACTTAGTT
CACCGTAGCTACAGAGGTGCGTGGGCGCGCACGACTAGCCTAACCATAATATGCCTGACGAAGTATGAATCAA  1423

FIGURE 1D

|  | Source Organism (organelle) | GenBank Accession No. |
|---|---|---|
| SEQ ID NO: 11 | Agrobacterium tumefaciens | O30992 |
| SEQ ID NO: 12 | Sinorhizobium melilote | P30327 |
| SEQ ID NO: 13 | Bartonella clarridgeiae | AAD31718 |
| SEQ ID NO: 14 | Rickettsia prowazekii | Q9ZCQ3 |
| SEQ ID NO: 15 | Caulobacter crescentus | P52976 |
| SEQ ID NO: 16 | Cyanidioschyzon merolae (mt) | BAA85115 |
| SEQ ID NO: 4 | Phytophthora infestans -mt2 | this invention |
| SEQ ID NO: 17 | Mallomonas splendens (mt) | AAF35432 |
| SEQ ID NO: 2 | Phytophthora infestans -mt1 | this invention |
| SEQ ID NO: 18 | Gentiana lutea (cp) | T51088 |
| SEQ ID NO: 19 | Nicotiana tabacum (cp, 2-1) | T51087 |
| SEQ ID NO: 20 | Arabidopsis thaliana (cp, 2-1) | T49028 |
| SEQ ID NO: 21 | Physcomitrella patens (cp, 1) | T51089 |
| SEQ ID NO: 22 | Physcomitrella patens (cp, 2) | T51090 |
| SEQ ID NO: 23 | Guillardia theta (cp) | CAB40398 |
| SEQ ID NO: 24 | Mallomonas spendens (cp) | AAF35433 |
| SEQ ID NO: 25 | Anabaena PCC7120 | CAA83241 |
| SEQ ID NO: 26 | Synechocystis PCC6803 | P73456 |
| SEQ ID NO: 27 | Arabidopsis thaliana (cp, 1-1) | Q42545 |
| SEQ ID NO: 28 | Pisum sativum (cp) | T06774 |
| SEQ ID NO: 29 | Nicotiana tabacum (cp, 1-3) | CAB89287 |
| SEQ ID NO: 30 | Nicotiana tabacum (cp, 1) | CAB41987 |
| SEQ ID NO: 31 | Nicotiana tabacum (cp, 1-1) | CAB89286 |
| SEQ ID NO: 32 | Nicotiana tabacum (cp, 2) | AAF23770 |

```
Bacterial FtsZ    1                                                50
SEQ ID NO: 11  PRITVFGVGGGGGNAVNNMITVGLQGVDFVVANTDAQALTMT..KADRVIQLGVNVTEGL
SEQ ID NO: 12  PRITVFGVGGGGGNAVNNMITAGLQGVDFVVANTDAQALTMT..KAERIIQMGVAVTEGL
SEQ ID NO: 13  PRITVFGVGGGGGNAVNNMINAGLQGVDFVVANTDAQALAMS..KAERVIQLGAAVTEGL
SEQ ID NO: 14  PTITVFGVGGAGSNAVNNMIHANLQGANFVVANTDAQQLEHS..LCINKIQLGVSTTRGL
SEQ ID NO: 15  PRIVVFGVGGAGGNAVNNMIEAGLEGVEFVVANTDAQQLQFA..KTDRRIQLGVQITQGL
Mitochondrial FtsZ
SEQ ID NO: 16  PRIMVVGVGGAGGNAVNNMIASSLPGVEFLVANTDAQALKMS..LCPNRIQLGASLTEGL
SEQ ID NO:  4  PKIVVVGVGGAGGNAVNNMIARGLQGVEFLVCNTDAQHLRTT..LTENRVQMAPELTGGL
SEQ ID NO: 17  PKICVFGVGGGGCNAVNNMIARKLSGVEFVCANTDAQHLSTC..LTENKLQLGKESTQGL
SEQ ID NO:  2  AS....................QLEGVEFIVANTDCQALGRS..LAPHKITLGKDITKGL
Chloroplast FtsZ
SEQ ID NO: 18  AKIKVVGVGGGGSNAVNRMIESAMKGVEFWIVNTDVQAIKMSPVYLENRLQIGQELTRGL
SEQ ID NO: 19  AKIKVVGVGGGGSNAVNRMIESSMKGVEFWIVNTDIQAMRMSPVAAEQRLPIGQELTRGL
SEQ ID NO: 20  ARIKVIGVGGGGSNAVNRMIESEMSGVEFWIVNTDIQAMRMSPVLPDNRLQIGKELTRGL
SEQ ID NO: 21  AKIKVIGVGGGGSNAVNRMLESEMQGVEFWIVNTDAQAMALSPVPAQNRLQIGQKLTRGL
SEQ ID NO: 22  AKIKVIGVGGGGSNAVNRMLESEMQGVEFWIVNTDAQAMALSPVPAQNRLQIGQKLTRGL
SEQ ID NO: 23  CVIKVIGVGGGGGNAVNRMVG.GVEGVEFWSINTDAQALSRS..LAPNTCNIGAKLTRGL
SEQ ID NO: 24  .....................GVELWVVNTDAQALSRS..SAKRRLNIGKVLSRGL
SEQ ID NO: 25  ANIKVIGVGGGGGNAVNRMIESDVSGVEFWSINTDAQALTLA..GAPSRLQIGQKLTRGL
SEQ ID NO: 26  AKIKVGGGGCNAVNRMIASGVTGIDFWAINTDSQALTNT..NAPDCIQIGQKLTRGL
SEQ ID NO: 27  ARIKVIGVGGGGNNAVNRMISSGLQSVDFYAINTDSQALLQFSA..ENPLQIGELLTRGL
SEQ ID NO: 28  AKIKVVGIGGGGNNAVNRMIGSGLQGVDFYAINTDAQALLHSAA..ENPIKIGELLTRGL
SEQ ID NO: 29  AKIKVIGVGGGGNNAVNRMIGSGLQGVDFYAINTDAQALLQSAA..ENPLQIGELLTRGL
SEQ ID NO: 30  AKIKVIGVGGGGNNAVNRMIGSGLQGVDFYAINTDAQALLQSAA..ENPLQIGELLTRGL
SEQ ID NO: 31  AKIKVVGVGGGGNNAVNRMIGSGLQGVDFYAVNTDAQALLQSTV..ENPIQIGELLTRGL
SEQ ID NO: 32  AKIKVVGVGGGGNNAVNRMIGSGLQGVDFYAVNTDAQALLQSTV..ENPIQIGELLTRGL
```

FIGURE 2A

```
Bacterial FtsZ  60                                                   110
SEQ ID NO: 11   GAGSQPEVGRAAAEECIDEIIDHLNGTHMCFVTAGMGGGTGTGAAPVVAQAARNKGILTV
SEQ ID NO: 12   GAGSQPEVGRAAAEECIDEIIDHLQGTHMCFVTAGMGGGTGTGAAPIVAQAARNKGILTV
SEQ ID NO: 13   GAGALPEVGRAAADECIDEIIDHLADSHMVFITAGMGGGTGTGAAPVVANAAREKGILTV
SEQ ID NO: 14   GAGASPEVGALAAQESENEIRSSLENSNMVFITAGMGGGTGTGSAPIIARIAKELGILTV
SEQ ID NO: 15   GAGAHPEVGMSAAEESFPEIGEHLDGAHMVFITAGMGGGTGTGAAPIIAKCARERGILTV
Mitochondrial FtsZ
SEQ ID NO: 16   GAGARPDIGRAAAEEAYETLKREFRGVHLLFVTAGMGGGTGTGAAPIIARAAAELGCLTV
SEQ ID NO:  4   GCCANPEVGREAAEAAIDEILERVQGANMMFVTAGMGGGTGTGAAPVIAQAALDAGILTV
SEQ ID NO: 17   GCGANPESGRRAAEESKEEIARYIADANMVFITAGMGGGTGTGAAPVVAEVCMEKDILTV
SEQ ID NO:  2   GAGSKPELGKRSAEQQKVDIQRMLQDSNMLFITGGMGGGTCTGAAPVVASVARELGILTV
Chloroplast FtsZ
SEQ ID NO: 18   GAGGNPDIGMNAAKESKEAIEEAVYGADMVFVTAGMGGGTGTGGAPVIAGIAKSMGILTV
SEQ ID NO: 19   GAGGNPDIGMNAANESKQAIEEAVYGADMVFVTAGMGGGTGTGAAPIIAGTAKSMGILTV
SEQ ID NO: 20   GAGGNPEIGMNAARESKEVIEEALYGSDMVFVTAGMGGGTGTGAAPVIAGIAKAMGILTV
SEQ ID NO: 21   GAGGNPEIGCSAAEESKAMVEEALRGADMVFVTAGMGGGTGTGAAPVIAGVAKQLGILTV
SEQ ID NO: 22   GAGGNPEIGCSAAEESKAMVEEALRGADMVFVTAGMGGGTGSGAAPIIAGVAKQLGILTV
SEQ ID NO: 23   GAGGNPEIGRKAAEESRDLIAEAVSAGDLVFVTAGMGGGTGSGAAPIVAEVAKEMGCLTV
SEQ ID NO: 24   GAGGNPAIGAKAAEESREEIMAVVKNADLVFVTAGMGGGTGSGAAPVVAECAKEAGALTV
SEQ ID NO: 25   GAGGNPAIGQKAAEESRDEIATALEGADLVFITAGMGGGTGTGAAPIVAEVAKEMGALTV
SEQ ID NO: 26   GAGGNPAIGQKAAEESRDEIARSLEGTDLVFITAGMGGGTGTGAAPIVAEVAKEMGCLTV
SEQ ID NO: 27   GTGGNPLLGEQAAEESKDAIANALKGSDLVFITAGMGGGTGSGAAPVVAQISKDAGYLTV
SEQ ID NO: 28   GTGGNPLLGEQAAEESKEAIANALKGSDLVFITAGMGGGTGSGAAPVVAQISKEAGYLTV
SEQ ID NO: 29   GTGGNPLLGEQAAEESKEAIANSLKGSDMVFITAGMGGGTGSGAAPVVAQIAKEAGYLTV
SEQ ID NO: 30   GTGGNPLLGEQAAEESKEAIANSLKGSDMVFITAGMGGGTGSGAAPVVAQIAKEAGYLTV
SEQ ID NO: 31   GTGGNPLLGEQAAEESKEHIANALKGSDMVFITAGMGGGTGSGAAPVVAQIAKEAGYLTV
SEQ ID NO: 32   GTGGNPLLGEQAAEESKEHIANALKGSDMVFITAGMGGGTGSGAAPVVAQIAKEAGYLTV
Bacterial FtsZ  120                                                  170
SEQ ID NO: 11   GVVTKPFHFEGGRRMRLAEQGIEELQKSVDTLIVIPNQNLFRIANDKTTFADAFAMADQV
SEQ ID NO: 12   GVVTKPFHFEGGRRMRIADQGISDLQKSVDTLIVIPNQNLFRIANDKTTFADAFAMADQV
SEQ ID NO: 13   GVVTKPFQFEGARRMKTAEAGIEELQKSVDTLIVIPNQNLFRIANEKTTFSDAFAMADQV
SEQ ID NO: 14   GVVTKPFHFEGGHRMKTADKGLIELQQFVDTLIVIPNQNLFRIANEQTTFADAFKMADDV
SEQ ID NO: 15   GVVTKPFHFEGRHRMRLADSGIQELQRYVDTLIVIPNQNLFRVANERTTFAEAFGMADQV
Mitochondrial FtsZ
SEQ ID NO: 16   AVVTKPFHFEGMIRMKTAEQGIVELTEHVDTMLVIPNQNLFKVASPRTSFLDAFRLADHV
SEQ ID NO:  4   AVVTKPFRFEGNNRAKLAAQGLAELKDSVDTMLVIPNQNLFNMSNERTSLMDAFRMADNV
SEQ ID NO: 17   AVVTKPFSFEGKHRARLANEGIRSLEDRVDTLIIIPNQNIFKLINASTSMADAFGLADDI
SEQ ID NO:  2   GVVSTPFRSEGPNRTRLANAGVKELAKYVDTLIVVPNQNLLALADKSTTMLEAFRYADDV
Chloroplast FtsZ
SEQ ID NO: 18   GIVTTPFSFEGRRRAVQAQEGIAALRDNVDTLIVIPNDKLLTAVSPSTPVTEAFNLADDI
SEQ ID NO: 19   GIVTTPFSFEGRRRAVQAQEGIAALRENVDTLIVIPNDKLLTAVSPSTPVTEAFNLADDI
SEQ ID NO: 20   GIATTPFSFEGRRRTVQAQEGLASLRDNVDTLIVIPNDKLLTAVSQSTPVTEAFNLADDI
SEQ ID NO: 21   GIVTTPFAFEGRRRAVQAHEGIAALKNNVDTLITIPNNKLLTAVAQSTPVTEAFNLADDI
SEQ ID NO: 22   GIVTTPFAFEGRRRSVQAHEGIAALKNNVDTLITIPNNKLLTAVAQSTPVTEAFNLADDI
SEQ ID NO: 23   GVVTKPFAFEGKRRMQQANDAILNLRNKVDTLIVVSNDKLLQIVPDNTPLQDAFSVADDI
SEQ ID NO: 24   GVVTKPFGFEGRKRMQQARNAILEMKDKVDTLIVVSNDKLLKIVPDNTPLTEAFLVADDI
SEQ ID NO: 25   GVVTRPFVFEGRRRTSQAEQGIEGLKSRVDTLIIIPNNKLLEVIPEQTPVQEAFRYADDV
SEQ ID NO: 26   GIVTRPFTFEGRRRAKQAEEGINALQSRVDTLIVIPNNQLLSVIPAETPLQEAFRVADDI
SEQ ID NO: 27   GVVTYPFSFEGRKRSLQALEAIEKLQKNVDTLIVIPNDRLLDIADEQTPLQDAFLLADDV
SEQ ID NO: 28   GVVTYPFSFEGRKRSLQALEAIEKLQKNVDTLIVIPNDRLLDIADEQMPLQDAFRLADDV
SEQ ID NO: 29   GVVTYPFSFEGRKRSVQALEAIEKLQKNVDTLIVIPNDRLLDIADEQTPLQDAFLLADDV
SEQ ID NO: 30   GVVTYPFSFEGRKRSVQALEAIEKLQKNVDTLIVIPNDRLLDIADEQTPLQDAFLLADDV
SEQ ID NO: 31   GVVTYPFSFEGRKRSLQALEAIEKLQKNVDTLIVIPNDRLLDIADEQTPLQNAFLLADDV
SEQ ID NO: 32   GVVTYPFSFEGRKRSLQALEAIEKLQKNVDTLIVIPNDRLLDIADEQTPLQNAFLLADDV
```

FIGURE 2B

```
Bacterial FtsZ   180                                                            230
SEQ ID NO: 11    LYSGVACITDLMVKEGLINLDFADVRSVMREMARPMMGTGE....ASGPARAMQAAEAAI
SEQ ID NO: 12    LYSGVACITDLMVKEGLINLDFADVRSVMREMGRAMMGTGE....ASGEGRAMAAAEAAI
SEQ ID NO: 13    LYSGVASITDLMIKEGLINLDFADVRSVMHEMGRAMMGTGE....ASGDGRALAAAEAAI
SEQ ID NO: 14    LHAGVRGVTDLMIMPGLINLDFADIKAVMSEMGKAMMGTGE....DSGEDRAIKAAESAI
SEQ ID NO: 15    LHSGVRSITDLMVLPGLINLDFADVRTVMTEMGKAMMGTGE....GTAEDRALMAAQNAI
Mitochondrial FtsZ
SEQ ID NO: 16    LYSGVRSITDLMTVPGLINLDFADVRSVVREMGRAMMGSGEVEMEAGNEERAIRASEAAI
SEQ ID NO:  4    LLDGVKNISDLMVMPGLINLDFADVQSVMQNMGNAMMGSGEAD....GENRALRAAEDAL
SEQ ID NO: 17    LLAGVKSITDLMVRPGLINLDFADVRTVMSGMGHAIMGTGQAE....GEDRAIRAANDAL
SEQ ID NO:  2    LLEGVKGVTDLIVRPGLINL........................................
Chloroplast FtsZ
SEQ ID NO: 18    LRQGVRGISDIITIPGLVNVDFADVRAIMANAGSSLMGIGT....ATGKTRARDAALNAI
SEQ ID NO: 19    LRQGVRGISDIITIPGLVNVDFADVRAIMANAGSSLMGIGT....ATGKTRARDAALNAI
SEQ ID NO: 20    LRQGVRGISDIITIPGLVNVDFADVRAIMANAGSSLMGIGT....ATGKSRARDAALNAI
SEQ ID NO: 21    LRQGVRGISDIITVPGLVNVDFADVRAIMANAGSSLMGIGT....ATGKSRAREAALSAI
SEQ ID NO: 22    LRQGVRGISDIITVPGLVNVDFADVRAIMANAGSSLMGIGT....ATGKSKAREAALSAI
SEQ ID NO: 23    LRQGVVGISEIIVRPGLINVDFADVRSVMADAGSALMGIGT....GSGKTRAQDAAVAAI
SEQ ID NO: 24    LRQGVVGITEIIVKPGLVNVDFADVRTIMGNAGTALMGIGH....GKGKNRAKDAALSAI
SEQ ID NO: 25    LRQGVQGISDIITIPGLVNVDFADVRAVMADAGSALMGIGV....SSGKSRAREAAIAAI
SEQ ID NO: 26    LRQGVQGISDIIIIPGLVNVDFADVRAVMADAGSALMGIGV....GSGKSRAKEAATAAI
SEQ ID NO: 27    LRQGVQGISDIITIPGLVNVDFADVKAVMKDSGTAMLGVGV....SSSKNRAEEAAEQAT
SEQ ID NO: 28    LRQGVQGISDIITIPGLVNVDFADVKAVMKDSGTAMLGVGV....SSGKNRAEEAAEQAT
SEQ ID NO: 29    LRQGVQGISDIITIPGLVNVDFADVKAVMKDSGTAMLGVGV....SSSKNRAEEAAEQAT
SEQ ID NO: 30    LRQGVQGISDIITIPGLVNVDFADVKAVMKDSGTAMLGVGV....SSSKNRAEEAAEQAT
SEQ ID NO: 31    LCQGVQGISDIITIPGLVNVDFADVKAIMKDSGTAMLGVGV....SSSRNRAEEAAEQAT
SEQ ID NO: 32    LCQGVQGISDIITIPGLVNVDFADVKAIMKDSGTAMLGVGV....SSSRNRAEEAAEQAT
Bacterial FtsZ   240                                                            290
SEQ ID NO: 11    ANPLLD.ETSMKGAQGLLISITGGRDLTLFEVDEAATRIREEVDP.DANIILGATFDEAL
SEQ ID NO: 12    ANPLLD.ETSMKGAQGLLISITGGRDLTLFEVDEAATRIREEVDP.DANIILGATFDEEL
SEQ ID NO: 13    ANPLLD.DTSMRGARGLLISITGGRDMTLFEVDEAANRIREEVDA.DANVIFGAIDDESL
SEQ ID NO: 14    SNPLLD.HSSMCGARGVLINITGGPDMTLFEVDNAANRIREEVDNIDANIIFGSTFNPEL
SEQ ID NO: 15    ANPLLD.EVSLKGAKAVLVNVTGGMDMTLLEVDEAANAISDQVDP.EANIIFGAAFDPSL
Mitochondrial FtsZ
SEQ ID NO: 16    CNPLLD.ETSLRGARGVLVNITGGTDMTLFEIDAAANRIREQVDP.DANIIFGSAFDASM
SEQ ID NO:  4    ANPLLG.DISIKDAKGMIVNITGGSDLTLFEVDEAAERVTRELDDPHANIIFGSTFDDSL
SEQ ID NO: 17    NNPLLGGDFSVRSAKGMLVNITGGKDLTLVEVDAAAQRITSEIEDEDANVIFGSSFDESL
SEQ ID NO:  2    ............................................................
Chloroplast FtsZ
SEQ ID NO: 18    QSPLLD..IGIERATGIVWNITGGSDLTLFEVNAAAEVIYDLVDP.SANLIFGAVVDPSL
SEQ ID NO: 19    QSPLLD..IGIERATGIVWNITGGSDLTLFEVNAAAEVIYDLVDP.SANLIFGAVIDPSI
SEQ ID NO: 20    QSPLLD..IGIERATGIVWNITGGSDLTLFEVNAAAEVIYDLVDP.TANLIFGAVVDPAL
SEQ ID NO: 21    QSPLLD..VGIERATGIVWNITGGSDMTLFEVNAAAEVIYDLVDP.NANLIFGAVVDEAL
SEQ ID NO: 22    QSPLLD..VGIERATGIVWNITGGSDMTLFEVNAAAEVIYDLVDP.NANLIFGAVVDEAL
SEQ ID NO: 23    SSPLLD..FPIEKARGIVFNITGGQDMTLHEINSAAEVIYEAVDS.NANIIFGALVDDNM
SEQ ID NO: 24    SSPLLD..FPITRAKGIVFNIVGGSDMSLQEINAAAEVIYENVDQ.DANIIFGAMVDDKM
SEQ ID NO: 25    SSPLLE..CSIEGARGVVFNITGGSDLTLHEVNAAAETIYEVVDP.NANIIFGAVIDDRL
SEQ ID NO: 26    SSPLLE..SSIQGAKGVVFNVTGGTDLTLHEVNVAAEIIYEVVDA.DANIIFGAVIDDRL
SEQ ID NO: 27    LAPLIG..SSIQSATGVVYNITGGKDITLQEVNRVSQVVTSLADP.SANIIFGAVDDRY
SEQ ID NO: 28    LAPLIG..SSIQSATGVVYNITGGKDITLQEVNRVSQVVTSLADP.SANIIFGAVDDRY
SEQ ID NO: 29    LAPLIG..SSIQSATGVVYNITGGKDITLQEVNRVSQVVTSLADP.SANIIFGAVDERY
SEQ ID NO: 30    LAPLIG..SSIQSATGVVYNITGGKDITLQEVNRVSQVVTSLADP.SANIIFGAVDERY
SEQ ID NO: 31    LAPLIG..LSIQSATGVVYNITGGKDITLQEVNKVSQVVTSLADP.SANIIFGAVVDERY
SEQ ID NO: 32    LAPLIG..SSIQSATGDVYNITGGKDITLQEVNKVSQVVTSLADP.SANIIFGAVVDERY
```

FIGURE 2C

Bacterial FtsZ                300

SEQ ID NO: 11    E.GLIRVSVVATGI
SEQ ID NO: 12    E.GLIRVSVVATGI
SEQ ID NO: 13    E.GVIRVSVVATGI
SEQ ID NO: 14    K.GIIRVSVVATGI
SEQ ID NO: 15    E.GVIRVSVVATGM

Mitochondrial FtsZ

SEQ ID NO: 16    Q.GRLRVSVLATGI
SEQ ID NO:  4    G.GKLRVSVVATGI
SEQ ID NO: 17    Q.GSIRVSIVATGI
SEQ ID NO:  2    ..............

Chloroplast FtsZ

SEQ ID NO: 18    C.GQVSITLIATGF
SEQ ID NO: 19    S.GQVSITLIATGF
SEQ ID NO: 20    S.GQVSITLIATGF
SEQ ID NO: 21    H.GQVSITLIATGF
SEQ ID NO: 22    H.DQISITLIATGF
SEQ ID NO: 23    EN.EISITVVATGF
SEQ ID NO: 24    TSGEVSITVLATGF
SEQ ID NO: 25    Q.GEVRITVIATGF
SEQ ID NO: 26    Q.GEMRITVIATGF
SEQ ID NO: 27    .TGEIHVTIIATGF
SEQ ID NO: 28    .TGEIHVTIIATGF
SEQ ID NO: 29    .NGEIHVTIIATGF
SEQ ID NO: 30    .NGEIHVTIIATGF
SEQ ID NO: 31    .NGEIQVTLIATGF
SEQ ID NO: 32    .NGEIQVTLIATGF

FIGURE 2D

SEQUENCE LISTING

<160> NUMBER OF SEQ ID NOS: 32

<210> SEQ ID NO 1
<211> LENGTH: 535
<212> TYPE: DNA
<213> ORGANISM: Phytophthora infestans
<220> FEATURE:
<221> NAME/KEY: CDS
<222> LOCATION: (2)...(535)

<400> SEQUENCE: 1

```
c gcg tcg caa ttg gaa ggt gtg gag ttc att gta gcc aac aca gac tgt      49
  Ala Ser Gln Leu Glu Gly Val Glu Phe Ile Val Ala Asn Thr Asp Cys
   1               5                  10                  15 cag gct ctg gga cgc tcg ctg gcg ccg cac aag atc acg ctg ggc aaa        97
Gln Ala Leu Gly Arg Ser Leu Ala Pro His Lys Ile Thr Leu Gly Lys
             20                  25                  30 gat atc acc aag gga cta gga gct gga tcc aaa cct gag ctg ggt aaa       145
Asp Ile Thr Lys Gly Leu Gly Ala Gly Ser Lys Pro Glu Leu Gly Lys
         35                  40                  45 cgc tct gcg gaa cag cag aaa gtg gat atc caa cgg atg tta cag gac       193
Arg Ser Ala Glu Gln Gln Lys Val Asp Ile Gln Arg Met Leu Gln Asp
     50                  55                  60 agc aac atg ctg ttt atc acg ggc gga atg ggc ggc gga acc tgc aca       241
Ser Asn Met Leu Phe Ile Thr Gly Gly Met Gly Gly Gly Thr Cys Thr
 65                  70                  75                  80 gga gcc gca cct gtc gtg gcc agt gta gcc agg gag ctg ggg atc cta       289
Gly Ala Ala Pro Val Val Ala Ser Val Ala Arg Glu Leu Gly Ile Leu
                 85                  90                  95 acg gtc gga gta gta agc aca ccg ttc cga tcc gaa gga ccc aat cgc       337
Thr Val Gly Val Val Ser Thr Pro Phe Arg Ser Glu Gly Pro Asn Arg
            100                 105                 110 act cgt ctg gcc aat gct gga gta aaa gaa ctg gcc aag tac gtc gac       385
Thr Arg Leu Ala Asn Ala Gly Val Lys Glu Leu Ala Lys Tyr Val Asp
        115                 120                 125 acc tta att gtc gtg ccc aac cag aac ttg ctg gct ttg gca gac aag       433
Thr Leu Ile Val Val Pro Asn Gln Asn Leu Leu Ala Leu Ala Asp Lys
    130                 135                 140 agc acg acc atg ttg gaa gcc ttc cgg tat gcc gac gac gtg ctg ctt       481
Ser Thr Thr Met Leu Glu Ala Phe Arg Tyr Ala Asp Asp Val Leu Leu
145                 150                 155                 160 gaa gga gtt aaa ggt gtc acg gac ttg atc gtt cgc ccg gga ctt atc       529
Glu Gly Val Lys Gly Val Thr Asp Leu Ile Val Arg Pro Gly Leu Ile
                165                 170                 175 aat ttg                                                                535
Asn Leu
```

<210> SEQ ID NO 2
<211> LENGTH: 178
<212> TYPE: PRT
<213> ORGANISM: Phytophthora infestans

<400> SEQUENCE: 2

```
Ala Ser Gln Leu Glu Gly Val Glu Phe Ile Val Ala Asn Thr Asp Cys
 1               5                  10                  15

Gln Ala Leu Gly Arg Ser Leu Ala Pro His Lys Ile Thr Leu Gly Lys
             20                  25                  30

Asp Ile Thr Lys Gly Leu Gly Ala Gly Ser Lys Pro Glu Leu Gly Lys
         35                  40                  45
```

```
Arg Ser Ala Glu Gln Gln Lys Val Asp Ile Gln Arg Met Leu Gln Asp
    50                  55                  60

Ser Asn Met Leu Phe Ile Thr Gly Gly Met Gly Gly Thr Cys Thr
65                  70                  75                  80

Gly Ala Ala Pro Val Val Ala Ser Val Ala Arg Glu Leu Gly Ile Leu
                85                  90                  95

Thr Val Gly Val Val Ser Thr Pro Phe Arg Ser Glu Gly Pro Asn Arg
            100                 105                 110

Thr Arg Leu Ala Asn Ala Gly Val Lys Glu Leu Ala Lys Tyr Val Asp
            115                 120                 125

Thr Leu Ile Val Val Pro Asn Gln Asn Leu Leu Ala Leu Ala Asp Lys
            130                 135                 140

Ser Thr Thr Met Leu Glu Ala Phe Arg Tyr Ala Asp Asp Val Leu Leu
145                 150                 155                 160

Glu Gly Val Lys Gly Val Thr Asp Leu Ile Val Arg Pro Gly Leu Ile
                165                 170                 175

Asn Leu

<210> SEQ ID NO 3
<211> LENGTH: 220
<212> TYPE: DNA
<213> ORGANISM: Phytophthora infestans
<220> FEATURE:
<221> NAME/KEY: CDS
<222> LOCATION: (2)...(220)
<223> OTHER INFORMATION: cDNA

<400> SEQUENCE: 3 c gcg cgc ggc ctg cag ggt gtg gag ttt ctt gtt tgc aac acg gat gct      49
  Ala Arg Gly Leu Gln Gly Val Glu Phe Leu Val Cys Asn Thr Asp Ala
  1               5                   10                  15 cag cac tta cgc acg acg ctg acg gag aac cgc gtt cag atg gct cct      97
Gln His Leu Arg Thr Thr Leu Thr Glu Asn Arg Val Gln Met Ala Pro
            20                  25                  30 gaa ttg act gga gga ttg ggc tgt ggc gct aac ccc gaa gtt ggc cga     145
Glu Leu Thr Gly Gly Leu Gly Cys Gly Ala Asn Pro Glu Val Gly Arg
        35                  40                  45 gag gcg gca gag gcc gcg att gat gag att ttg gag cgc gtt cag ggt     193
Glu Ala Ala Glu Ala Ala Ile Asp Glu Ile Leu Glu Arg Val Gln Gly
    50                  55                  60 gca aac atg atg ttt gtt act gcg ggt                                 220
Ala Asn Met Met Phe Val Thr Ala Gly
 65                 70

<210> SEQ ID NO 4
<211> LENGTH: 73
<212> TYPE: PRT
<213> ORGANISM: Phytophthora infestans

<400> SEQUENCE: 4

Ala Arg Gly Leu Gln Gly Val Glu Phe Leu Val Cys Asn Thr Asp Ala
1               5                   10                  15

Gln His Leu Arg Thr Thr Leu Thr Glu Asn Arg Val Gln Met Ala Pro
            20                  25                  30

Glu Leu Thr Gly Gly Leu Gly Cys Gly Ala Asn Pro Glu Val Gly Arg
        35                  40                  45

Glu Ala Ala Glu Ala Ala Ile Asp Glu Ile Leu Glu Arg Val Gln Gly
    50                  55                  60
```

```
Ala Asn Met Met Phe Val Thr Ala Gly
 65                  70

<210> SEQ ID NO 5
<211> LENGTH: 388
<212> TYPE: DNA
<213> ORGANISM: Phytophthora infestans
<220> FEATURE:
<221> NAME/KEY: intron
<222> LOCATION: (143)...(204)
<221> NAME/KEY: intron
<222> LOCATION: (265)...(370)
<221> NAME/KEY: CDS
<222> LOCATION: (2)...(142)
<221> NAME/KEY: CDS
<222> LOCATION: (205)...(264)
<221> NAME/KEY: CDS
<222> LOCATION: (371)...(388)

<400> SEQUENCE: 5 c gcg cgc ggc ctg cag ggt gtg gag ttt ctt gtt tgc aac acg gat gct    49
  Ala Arg Gly Leu Gln Gly Val Glu Phe Leu Val Cys Asn Thr Asp Ala
   1               5                  10                  15 cag cac tta cgc acg acg ctg acg gag aac cgc gtt cag atg gct cct    97
Gln His Leu Arg Thr Thr Leu Thr Glu Asn Arg Val Gln Met Ala Pro
             20                  25                  30 gaa ttg act gga gga ttg ggc tgt ggc gct aac ccc gaa gtt ggg        142
Glu Leu Thr Gly Gly Leu Gly Cys Gly Ala Asn Pro Glu Val Gly
         35                  40                  45 tgagtgactg cgtaaaagcg gtattttttt ttcttacata ctgaccttaa ctattgatta    202 gc cga gag gcg gca gag gcc gcg att gat gag att ttg gag cgc gtt    249
   Arg Glu Ala Ala Glu Ala Ala Ile Asp Glu Ile Leu Glu Arg Val
        50                  55                  60 cag ggt gca aac atg gtttgtctcg gtgacattgc gtttctcaag acgttccgat    304
Gln Gly Ala Asn Met
            65 ttgagcgaat gacttggtga tgacaacgat atgattatta acttctgctt ttatgcccct    364 atatag atg ttt gtt act gcg ggt                                        388
       Met Phe Val Thr Ala Gly
                70

<210> SEQ ID NO 6
<211> LENGTH: 20
<212> TYPE: DNA
<213> ORGANISM: Artificial Sequence
<220> FEATURE:
<223> OTHER INFORMATION: PCR primer
<221> NAME/KEY: misc_feature
<222> LOCATION: (1)...(20)
<223> OTHER INFORMATION: n = inosine

<400> SEQUENCE: 6
aaygcngtna ayaayatgat                                                 20

<210> SEQ ID NO 7
<211> LENGTH: 20
<212> TYPE: DNA
<213> ORGANISM: Artificial Sequence
<220> FEATURE:
<223> OTHER INFORMATION: PCR primer
<221> NAME/KEY: misc_feature
<222> LOCATION: (1)...(20)
<223> OTHER INFORMATION: n = inosine

<400> SEQUENCE: 7
gtnccngtnc cnccncccat                                                 20
```

<210> SEQ ID NO 8
<211> LENGTH: 20
<212> TYPE: DNA
<213> ORGANISM: Artificial Sequence
<220> FEATURE:
<223> OTHER INFORMATION: PCR primer
<221> NAME/KEY: misc_feature
<222> LOCATION: (1)...(17)
<223> OTHER INFORMATION: n = inosine

<400> SEQUENCE: 8
gtncknacrt cngcraartc                                                    20

<210> SEQ ID NO 9
<211> LENGTH: 1423
<212> TYPE: DNA
<213> ORGANISM: Phytophthora infestans
<220> FEATURE:
<221> NAME/KEY: CDS
<222> LOCATION: (2)...(1261)

<400> SEQUENCE: 9

```
g atg gcg ata tcc cgc atg aaa gct gcg gcg atg gcg ctg cta cgt gcc      49
  Met Ala Ile Ser Arg Met Lys Ala Ala Ala Met Ala Leu Leu Arg Ala
   1               5                  10                  15 cgc cag acc tcc cag tcc gcc act caa cac ctc gcc ttc tct act gaa        97
Arg Gln Thr Ser Gln Ser Ala Thr Gln His Leu Ala Phe Ser Thr Glu
            20                  25                  30 gcc act gat gct gca gct gcc gcg tta cgc atg ggc ttt aaa aag gct       145
Ala Thr Asp Ala Ala Ala Ala Ala Leu Arg Met Gly Phe Lys Lys Ala
        35                  40                  45 cga aaa gac gag gat ggc ggt gtg aaa gtg ggg ctg gag gca gag ccc       193
Arg Lys Asp Glu Asp Gly Gly Val Lys Val Gly Leu Glu Ala Glu Pro
    50                  55                  60 gat tca cca aca gat gtg agc gcc gtt tcg acg cca gta gta gag aag       241
Asp Ser Pro Thr Asp Val Ser Ala Val Ser Thr Pro Val Val Glu Lys
 65                  70                  75                  80 aag ctc gtg ccg cca gcc atg agc tcc aca cag cca ctt tgg ctc aca       289
Lys Leu Val Pro Pro Ala Met Ser Ser Thr Gln Pro Leu Trp Leu Thr
                85                  90                  95 cag gac cat cct gtg aca gac ctg tcg ggc ttt gca ccg aag att gtg       337
Gln Asp His Pro Val Thr Asp Leu Ser Gly Phe Ala Pro Lys Ile Val
            100                 105                 110 gtg gtt ggc gtc gga gga gct gga gga aat gcg gtg aac aac atg atc       385
Val Val Gly Val Gly Gly Ala Gly Gly Asn Ala Val Asn Asn Met Ile
        115                 120                 125 gcg cgc ggc ctg cag ggt gtg gag ttt ctt gtt tgc aac acg gat gct       433
Ala Arg Gly Leu Gln Gly Val Glu Phe Leu Val Cys Asn Thr Asp Ala
    130                 135                 140 cag cac tta cgc acg acg ctg acg gag aac cgc gtt cag atg gct cct       481
Gln His Leu Arg Thr Thr Leu Thr Glu Asn Arg Val Gln Met Ala Pro
145                 150                 155                 160 gaa ttg act gga gga ctg ggc tgt ggc gct aac ccc gaa gtt ggc cga       529
Glu Leu Thr Gly Gly Leu Gly Cys Gly Ala Asn Pro Glu Val Gly Arg
                165                 170                 175 gag gcg gca gag gcc gcg att gat gag att ttg gag cgc gtt cag ggt       577
Glu Ala Ala Glu Ala Ala Ile Asp Glu Ile Leu Glu Arg Val Gln Gly
            180                 185                 190 gca aac atg atg ttt gtt act gcg ggt atg ggt ggc gga aca ggt aca       625
Ala Asn Met Met Phe Val Thr Ala Gly Met Gly Gly Gly Thr Gly Thr
        195                 200                 205
```

-continued

| | |
|---|---|
| ggt gca gca ccc gtc att gct cag gct gcc tta gat gct ggt atc ctc<br>Gly Ala Ala Pro Val Ile Ala Gln Ala Ala Leu Asp Ala Gly Ile Leu<br>210              215                  220 | 673 |
| acc gta gct gtc gtt act aag ccg ttc cgg ttt gag gga aac aac cgt<br>Thr Val Ala Val Val Thr Lys Pro Phe Arg Phe Glu Gly Asn Asn Arg<br>225                  230                  235              240 | 721 |
| gca aag ctt gcg gca caa ggc ctc gct gaa ctg aag gat agc gtc gat<br>Ala Lys Leu Ala Ala Gln Gly Leu Ala Glu Leu Lys Asp Ser Val Asp<br>                 245                  250                  255 | 769 |
| acg atg ctt gtg atc ccg aac caa aac ttg ttc aac atg tca aat gag<br>Thr Met Leu Val Ile Pro Asn Gln Asn Leu Phe Asn Met Ser Asn Glu<br>             260                  265                  270 | 817 |
| cgc acc tcg ttg atg gac gca ttc aga atg gcg gac aat gtg ctt ctg<br>Arg Thr Ser Leu Met Asp Ala Phe Arg Met Ala Asp Asn Val Leu Leu<br>         275                  280                  285 | 865 |
| gac ggt gtc aag aac att tcg gat ttg atg gtg atg cct ggg ctc att<br>Asp Gly Val Lys Asn Ile Ser Asp Leu Met Val Met Pro Gly Leu Ile<br>     290                  295                  300 | 913 |
| aac ctt gac ttt gcg gat gtt caa tcg gtc atg caa aat atg gga aac<br>Asn Leu Asp Phe Ala Asp Val Gln Ser Val Met Gln Asn Met Gly Asn<br>305                  310                  315              320 | 961 |
| gct atg atg gga agt gga gag gcc gat gga gag aat cgg gct ctg cgt<br>Ala Met Met Gly Ser Gly Glu Ala Asp Gly Glu Asn Arg Ala Leu Arg<br>                 325                  330                  335 | 1009 |
| gct gct gaa gat gca ttg gcg aac cct ctt ctg ggt gat att tcg att<br>Ala Ala Glu Asp Ala Leu Ala Asn Pro Leu Leu Gly Asp Ile Ser Ile<br>             340                  345                  350 | 1057 |
| aag gac gcc aag ggc atg atc gtt aat atc acg gga ggc tcc gac ctg<br>Lys Asp Ala Lys Gly Met Ile Val Asn Ile Thr Gly Gly Ser Asp Leu<br>         355                  360                  365 | 1105 |
| acg cta ttt gaa gtt gat gag gct gct gag cgt gtg acg cgg gaa ctt<br>Thr Leu Phe Glu Val Asp Glu Ala Ala Glu Arg Val Thr Arg Glu Leu<br>     370                  375                  380 | 1153 |
| gat gat cca cac gcc aac atc atc ttc ggt tcg acc ttc gac gac tcg<br>Asp Asp Pro His Ala Asn Ile Ile Phe Gly Ser Thr Phe Asp Asp Ser<br>385                  390                  395              400 | 1201 |
| ctg ggc ggc aag cta cgc gtc tcc gtg gtt gcc act ggt att gcc gac<br>Leu Gly Gly Lys Leu Arg Val Ser Val Val Ala Thr Gly Ile Ala Asp<br>                 405                  410                  415 | 1249 |
| ccc gac aag tta tagaagccgt gatgttggcc agtatcaaag cgtaagcagg<br>Pro Asp Lys Leu<br>             420 | 1301 |
| ggaatgacac ctaatgacgt gattgctcaa gaaatctcta caatttgaag tggcatcgat | 1361 |
| gtctccacgc acccgcgcgt gctgatcgga ttggtattat acggactgct tcatacttag | 1421 |
| tt | 1423 |

<210> SEQ ID NO 10
<211> LENGTH: 420
<212> TYPE: PRT
<213> ORGANISM: Phytophthora infestans

<400> SEQUENCE: 10

Met Ala Ile Ser Arg Met Lys Ala Ala Ala Met Ala Leu Leu Arg Ala
 1               5                  10                  15

Arg Gln Thr Ser Gln Ser Ala Thr Gln His Leu Ala Phe Ser Thr Glu
                 20                  25                  30

Ala Thr Asp Ala Ala Ala Ala Leu Arg Met Gly Phe Lys Lys Ala
             35                  40                  45

```
Arg Lys Asp Glu Asp Gly Gly Val Lys Val Gly Leu Glu Ala Glu Pro
 50                  55                  60

Asp Ser Pro Thr Asp Val Ser Ala Val Ser Thr Pro Val Val Glu Lys
 65                  70                  75                  80

Lys Leu Val Pro Pro Ala Met Ser Ser Thr Gln Pro Leu Trp Leu Thr
                 85                  90                  95

Gln Asp His Pro Val Thr Asp Leu Ser Gly Phe Ala Pro Lys Ile Val
             100                 105                 110

Val Val Gly Val Gly Gly Ala Gly Gly Asn Ala Val Asn Asn Met Ile
         115                 120                 125

Ala Arg Gly Leu Gln Gly Val Glu Phe Leu Val Cys Asn Thr Asp Ala
 130                 135                 140

Gln His Leu Arg Thr Thr Leu Thr Glu Asn Arg Val Gln Met Ala Pro
145                 150                 155                 160

Glu Leu Thr Gly Gly Leu Gly Cys Gly Ala Asn Pro Glu Val Gly Arg
                165                 170                 175

Glu Ala Ala Glu Ala Ala Ile Asp Glu Ile Leu Glu Arg Val Gln Gly
             180                 185                 190

Ala Asn Met Met Phe Val Thr Ala Gly Met Gly Gly Gly Thr Gly Thr
         195                 200                 205

Gly Ala Ala Pro Val Ile Ala Gln Ala Ala Leu Asp Ala Gly Ile Leu
 210                 215                 220

Thr Val Ala Val Val Thr Lys Pro Phe Arg Phe Glu Gly Asn Asn Arg
225                 230                 235                 240

Ala Lys Leu Ala Ala Gln Gly Leu Ala Glu Leu Lys Asp Ser Val Asp
                245                 250                 255

Thr Met Leu Val Ile Pro Asn Gln Asn Leu Phe Asn Met Ser Asn Glu
             260                 265                 270

Arg Thr Ser Leu Met Asp Ala Phe Arg Met Ala Asp Asn Val Leu Leu
         275                 280                 285

Asp Gly Val Lys Asn Ile Ser Asp Leu Met Val Met Pro Gly Leu Ile
 290                 295                 300

Asn Leu Asp Phe Ala Asp Val Gln Ser Val Met Gln Asn Met Gly Asn
305                 310                 315                 320

Ala Met Met Gly Ser Gly Glu Ala Asp Gly Glu Asn Arg Ala Leu Arg
                325                 330                 335

Ala Ala Glu Asp Ala Leu Ala Asn Pro Leu Leu Gly Asp Ile Ser Ile
             340                 345                 350

Lys Asp Ala Lys Gly Met Ile Val Asn Ile Thr Gly Gly Ser Asp Leu
         355                 360                 365

Thr Leu Phe Glu Val Asp Glu Ala Ala Glu Arg Val Thr Arg Glu Leu
 370                 375                 380

Asp Asp Pro His Ala Asn Ile Ile Phe Gly Ser Thr Phe Asp Ser
385                 390                 395                 400

Leu Gly Gly Lys Leu Arg Val Ser Val Val Ala Thr Gly Ile Ala Asp
                405                 410                 415

Pro Asp Lys Leu
            420

<210> SEQ ID NO 11
<211> LENGTH: 583
<212> TYPE: PRT
<213> ORGANISM: Agrobacterium tumefaciens

<400> SEQUENCE: 11
```

-continued

```
Met Thr Ile Gln Leu Gln Lys Pro Asp Ile Thr Glu Leu Lys Pro Arg
 1               5                  10                 15

Ile Thr Val Phe Gly Val Gly Gly Gly Asn Ala Val Asn Asn
             20              25              30

Met Ile Thr Val Gly Leu Gln Gly Val Asp Phe Val Ala Asn Thr
         35              40              45

Asp Ala Gln Ala Leu Thr Met Thr Lys Ala Asp Arg Val Ile Gln Leu
 50                  55                  60

Gly Val Asn Val Thr Glu Gly Leu Gly Ala Gly Ser Gln Pro Glu Val
 65              70              75                  80

Gly Arg Ala Ala Ala Glu Glu Cys Ile Asp Glu Ile Ile Asp His Leu
                 85              90                  95

Asn Gly Thr His Met Cys Phe Val Thr Ala Gly Met Gly Gly Gly Thr
             100             105             110

Gly Thr Gly Ala Ala Pro Val Val Ala Gln Ala Ala Arg Asn Lys Gly
             115             120             125

Ile Leu Thr Val Gly Val Val Thr Lys Pro Phe His Phe Glu Gly Gly
 130             135             140

Arg Arg Met Arg Leu Ala Glu Gln Gly Ile Glu Glu Leu Gln Lys Ser
145                 150             155                 160

Val Asp Thr Leu Ile Val Ile Pro Asn Gln Asn Leu Phe Arg Ile Ala
                 165             170             175

Asn Asp Lys Thr Thr Phe Ala Asp Ala Phe Ala Met Ala Asp Gln Val
             180             185             190

Leu Tyr Ser Gly Val Ala Cys Ile Thr Asp Leu Met Val Lys Glu Gly
         195             200             205

Leu Ile Asn Leu Asp Phe Ala Asp Val Arg Ser Val Met Arg Glu Met
         210             215             220

Ala Arg Pro Met Met Gly Thr Gly Glu Ala Ser Gly Pro Ala Arg Ala
225                 230             235                 240

Met Gln Ala Ala Glu Ala Ala Ile Ala Asn Pro Leu Leu Asp Glu Thr
             245             250             255

Ser Met Lys Gly Ala Gln Gly Leu Leu Ile Ser Ile Thr Gly Gly Arg
             260             265             270

Asp Leu Thr Leu Phe Glu Val Asp Glu Ala Ala Thr Arg Ile Arg Glu
             275             280             285

Glu Val Asp Pro Asp Ala Asn Ile Ile Leu Gly Ala Thr Phe Asp Glu
             290             295             300

Ala Leu Glu Gly Leu Ile Arg Val Ser Val Val Ala Thr Gly Ile Asp
305                 310             315                 320

Arg Val Ala Gly Ile Gly Glu Gln Asn Ile Ala Glu Met Arg Ala Ala
                 325             330             335

Ala Ala Lys Pro Leu Ile Arg Pro Ser Ala Val Ala Pro Ala Pro
             340             345             350

Ala Ala Val Gln Pro Ala His Ala Val Ser Gln Ala Pro Lys Thr Val
             355             360             365

Asp Gln Ile Ala Gln Thr Ile Arg Ser Ala Glu Ala Glu Met Glu Arg
             370             375             380

Glu Leu Gly Phe Ala Ala His Gln Gln Pro Ser Gln Asp Phe Arg Pro
385                 390             395                 400

Gln Ser Lys Leu Phe Ala Ser Ser Pro Ala Glu Ala Pro Ala Ala Leu
                 405             410             415
```

```
Arg Pro Ala Gln Pro Val Gln Ala Ala Pro Ala Pro Val Ala Gln
            420                 425                 430

Ala Pro Val Tyr His Ala Pro Glu Gln Val Ala Val Pro Ala Pro Arg
            435                 440                 445

Met Gln Gln Ala Gln Ala Pro Val Tyr Gln Glu Pro Ala Pro Val Gly
            450                 455                 460

Arg Gln Pro Glu Pro Val Arg Met Pro Lys Val Glu Asp Phe Pro Pro
465                 470                 475                 480

Val Val Lys Ala Glu Met Asp His Arg Asp Arg Ala Thr Pro Val Ala
            485                 490                 495

Gln Glu Glu Arg Gly Pro Met Gly Leu Leu Lys Arg Ile Thr Asn Ser
            500                 505                 510

Leu Gly Arg Arg Glu Glu Glu Val Pro Ser Asp Met Met Asp Ala
            515                 520                 525

Pro Ser Met Ala Pro Gln Arg Arg Ala Pro Leu Ser Pro Glu Ala Ser
            530                 535                 540

Leu Tyr Ala Pro Arg Arg Gly Gln Leu Asp Asp His Gly Arg Ala Thr
545                 550                 555                 560

Pro Ser Ser Ser His His Asp Asp Asp Gln Leu Glu Ile Pro Ala
            565                 570                 575

Phe Leu Arg Arg Gln Ser Asn
            580

<210> SEQ ID NO 12
<211> LENGTH: 590
<212> TYPE: PRT
<213> ORGANISM: Sinorhizobium meliloti

<400> SEQUENCE: 12

Met Ala Ile Asn Leu Gln Lys Pro Asp Ile Thr Glu Leu Lys Pro Arg
 1               5                  10                  15

Ile Thr Val Phe Gly Val Gly Gly Gly Asn Ala Val Asn Asn
            20                  25                  30

Met Ile Thr Ala Gly Leu Gln Gly Val Asp Phe Val Val Ala Asn Thr
            35                  40                  45

Asp Ala Gln Ala Leu Thr Met Thr Lys Ala Glu Arg Ile Ile Gln Met
    50                  55                  60

Gly Val Ala Val Thr Glu Gly Leu Gly Ala Gly Ser Gln Pro Glu Val
65                  70                  75                  80

Gly Arg Ala Ala Ala Glu Glu Cys Ile Asp Glu Ile Ile Asp His Leu
            85                  90                  95

Gln Gly Thr His Met Cys Phe Val Thr Ala Gly Met Gly Gly Thr
            100                 105                 110

Gly Thr Gly Ala Ala Pro Ile Val Ala Gln Ala Ala Arg Asn Lys Gly
            115                 120                 125

Ile Leu Thr Val Gly Val Val Thr Lys Pro Phe His Phe Glu Gly Gly
            130                 135                 140

Arg Arg Met Arg Ile Ala Asp Gln Gly Ile Ser Asp Leu Gln Lys Ser
145                 150                 155                 160

Val Asp Thr Leu Ile Val Ile Pro Asn Gln Asn Leu Phe Arg Ile Ala
            165                 170                 175

Asn Asp Lys Thr Thr Phe Ala Asp Ala Phe Ala Met Ala Asp Gln Val
            180                 185                 190

Leu Tyr Ser Gly Val Ala Cys Ile Thr Asp Leu Met Val Lys Glu Gly
            195                 200                 205
```

```
Leu Ile Asn Leu Asp Phe Ala Asp Val Arg Ser Val Met Arg Glu Met
        210                 215                 220
Gly Arg Ala Met Met Gly Thr Gly Glu Ala Ser Gly Glu Gly Arg Ala
225                 230                 235                 240
Met Ala Ala Ala Glu Ala Ala Ile Ala Asn Pro Leu Leu Asp Glu Thr
                245                 250                 255
Ser Met Lys Gly Ala Gln Gly Leu Leu Ile Ser Ile Thr Gly Gly Arg
            260                 265                 270
Asp Leu Thr Leu Phe Glu Val Asp Glu Ala Ala Thr Arg Ile Arg Glu
        275                 280                 285
Glu Val Asp Pro Asp Ala Asn Ile Ile Leu Gly Ala Thr Phe Asp Glu
    290                 295                 300
Glu Leu Glu Gly Leu Ile Arg Val Ser Val Val Ala Thr Gly Ile Asp
305                 310                 315                 320
Arg Thr Ala Ala Glu Val Ala Gly Arg Ser Ala Asp Phe Arg Pro Val
                325                 330                 335
Ala Pro Lys Pro Ile Val Arg Pro Ser Ala Val Pro Ala Gln Pro
            340                 345                 350
Gln Pro Thr Val Ser Leu Gln Pro Val Pro Gln Pro Val Gln
        355                 360                 365
Gln Pro Leu Gln Gln Gln Asn Val Asp His Ile Ala Leu Ala Ile Arg
    370                 375                 380
Glu Ala Glu Met Glu Arg Glu Leu Asp Ile Ala Ala Arg Ala Gln Val
385                 390                 395                 400
Ala Ala Pro Ala Pro Gln Pro Gln Pro His Leu Gln Glu Glu Ala Phe
                405                 410                 415
Arg Pro Gln Ser Lys Leu Phe Ala Gly Val Ala Pro Thr Glu Ala Ala
            420                 425                 430
Pro Val Met Arg Pro Ala Gln Pro Ala Pro Arg Pro Val Glu Met Gln
        435                 440                 445
Ala Pro Val Gln Pro Gln Met Gln Ala Gln Pro Val Gln Gln Glu Pro
    450                 455                 460
Thr Gln Val Val Arg Gln Gln Ala Glu Pro Val Arg Met Pro Lys Val
465                 470                 475                 480
Glu Asp Phe Pro Pro Val Val Lys Ala Glu Met Asp Tyr Arg Thr Gln
                485                 490                 495
Pro Ala Pro Ala His Gln Glu Glu Arg Gly Pro Met Gly Leu Leu Asn
            500                 505                 510
Arg Ile Thr Ser Ser Leu Gly Leu Arg Glu Arg Glu Ala Thr Asn Val
        515                 520                 525
Ser Ser Asp Met Thr Ala Ala Pro Ser Ala Ala Ser Gln Gln Arg
    530                 535                 540
Arg Pro Leu Ser Pro Glu Ala Ser Leu Tyr Ala Pro Arg Arg Gly Gln
545                 550                 555                 560
Leu Asp Asp His Gly Arg Ala Ala Pro Gln Met Arg Ser His Glu Asp
                565                 570                 575
Asp Gln Leu Glu Ile Pro Ala Phe Leu Arg Arg Gln Ser Ser
            580                 585                 590

<210> SEQ ID NO 13
<211> LENGTH: 581
<212> TYPE: PRT
<213> ORGANISM: Bartonella clarridgeiae
```

<400> SEQUENCE: 13

```
Met Thr Ile Asn Leu His Arg Pro Asp Ile Ala Glu Leu Lys Pro Arg
 1               5                  10                  15

Ile Thr Val Phe Gly Val Gly Gly Gly Gly Asn Ala Val Asn Asn
             20                  25                  30

Met Ile Asn Ala Gly Leu Gln Gly Val Asp Phe Val Val Ala Asn Thr
             35                  40                  45

Asp Ala Gln Ala Leu Ala Met Ser Lys Ala Glu Arg Val Ile Gln Leu
     50                  55                  60

Gly Ala Ala Val Thr Glu Gly Leu Gly Ala Gly Ala Leu Pro Glu Val
 65                  70                  75                  80

Gly Arg Ala Ala Ala Asp Glu Cys Ile Asp Glu Ile Ile Asp His Leu
                 85                  90                  95

Ala Asp Ser His Met Val Phe Ile Thr Ala Gly Met Gly Gly Gly Thr
                100                 105                 110

Gly Thr Gly Ala Ala Pro Val Val Ala Asn Ala Ala Arg Glu Lys Gly
            115                 120                 125

Ile Leu Thr Val Gly Val Val Thr Lys Pro Phe Gln Phe Glu Gly Ala
        130                 135                 140

Arg Arg Met Lys Thr Ala Glu Ala Gly Ile Glu Glu Leu Gln Lys Ser
145                 150                 155                 160

Val Asp Thr Leu Ile Val Ile Pro Asn Gln Asn Leu Phe Arg Ile Ala
                165                 170                 175

Asn Glu Lys Thr Thr Phe Ser Asp Ala Phe Ala Met Ala Asp Gln Val
            180                 185                 190

Leu Tyr Ser Gly Val Ala Ser Ile Thr Asp Leu Met Ile Lys Glu Gly
        195                 200                 205

Leu Ile Asn Leu Asp Phe Ala Asp Val Arg Ser Val Met His Glu Met
    210                 215                 220

Gly Arg Ala Met Met Gly Thr Gly Glu Ala Ser Gly Asp Gly Arg Ala
225                 230                 235                 240

Leu Ala Ala Ala Glu Ala Ala Ile Ala Asn Pro Leu Leu Asp Asp Thr
                245                 250                 255

Ser Met Arg Gly Ala Arg Gly Leu Leu Ile Ser Ile Thr Gly Gly Arg
            260                 265                 270

Asp Met Thr Leu Phe Glu Val Asp Glu Ala Ala Asn Arg Ile Arg Glu
        275                 280                 285

Glu Val Asp Ala Asp Ala Asn Val Ile Phe Gly Ala Ile Asp Asp Glu
    290                 295                 300

Ser Leu Glu Gly Val Ile Arg Val Ser Val Val Ala Thr Gly Ile Asp
305                 310                 315                 320

Arg Glu Ile Asn Asp Val Ile Gln Pro Ser Asn Thr Lys Phe His Arg
                325                 330                 335

Ser Ala Thr Ser Met Arg Lys Asn Asp Ala Gly Val Thr Gln Thr Ser
            340                 345                 350

Ser Gln Ser Ser Leu Arg Ser Glu Ser Met Val Glu Val Ile Glu
        355                 360                 365

Ala Leu Glu Val Glu Met Lys Gln Pro Ile Glu Glu Pro Phe Cys Pro
    370                 375                 380

Lys Ser Gln Phe Phe Val Gln Ser Thr Asp Thr Tyr Thr Pro Arg Ser
385                 390                 395                 400

Met Asn Ala Ala Ser Tyr Gly Gln Asn Ile His Gly Gln Thr Ser Asn
                405                 410                 415
```

-continued

```
Ala Leu Arg Met Gln Val Gly Cys Val Ser Gln Gln Pro Val Ala Lys
            420                 425                 430

Ala Val Asn Met Glu Ala Thr Ala His Val Leu Asp Asp Met Thr Arg
            435                 440                 445

Ile Val Glu Gln Lys Lys Gln Ala Gln Met Gln Ser His Ser Met
        450                 455                 460

Ser Met Arg Met Pro Glu Leu Lys Asp Phe Pro Ser Ser Ile Arg Gly
465                 470                 475                 480

Gln Ser Thr Asn Phe Ser Asn Ala Asp Gln Gly Pro Arg Asn Leu Trp
                485                 490                 495

Gln Arg Leu Lys Gln Ser Leu Thr Tyr Arg Glu Glu Ala Glu Pro Glu
            500                 505                 510

Ala Arg Leu Glu Pro Ala Val Asn Ser Ser Leu Cys Lys Asp Ser His
            515                 520                 525

Ile Ser Ser Ala Ser Ser Gln Gly Ile Ser Gln Asp Thr Ser Val Tyr
            530                 535                 540

Ile Pro Arg His Ser Thr Glu Leu Gln Gln His Ala Ser Gln Asp Gln
545                 550                 555                 560

Asn Val Cys Val Ser Glu Glu Asp Glu Leu Glu Ile Pro Ala Phe Leu
                565                 570                 575

Arg Arg Gln Ala Asn
            580

<210> SEQ ID NO 14
<211> LENGTH: 452
<212> TYPE: PRT
<213> ORGANISM: Rickettsia prowazekii

<400> SEQUENCE: 14

Met Val Leu Asn Ile Lys Ala Pro Glu Asn Ile Val Leu Lys Pro Thr
1               5                   10                  15

Ile Thr Val Phe Gly Val Gly Gly Ala Gly Ser Asn Ala Val Asn Asn
            20                  25                  30

Met Ile His Ala Asn Leu Gln Gly Ala Asn Phe Val Val Ala Asn Thr
        35                  40                  45

Asp Ala Gln Ser Leu Glu His Ser Leu Cys Ile Asn Lys Ile Gln Leu
    50                  55                  60

Gly Val Ser Thr Thr Arg Gly Leu Gly Ala Gly Ala Ser Pro Glu Val
65                  70                  75                  80

Gly Ala Leu Ala Ala Gln Glu Ser Glu Asn Glu Ile Arg Ser Ser Leu
                85                  90                  95

Glu Asn Ser Asn Met Val Phe Ile Thr Ala Gly Met Gly Gly Gly Thr
            100                 105                 110

Gly Thr Gly Ser Ala Pro Ile Ile Ala Arg Ile Ala Lys Glu Leu Gly
        115                 120                 125

Ile Leu Thr Val Gly Val Val Thr Lys Pro Phe His Phe Glu Gly Gly
    130                 135                 140

His Arg Met Lys Thr Ala Asp Lys Gly Leu Ile Glu Leu Gln Gln Phe
145                 150                 155                 160

Val Asp Thr Leu Ile Val Ile Pro Asn Gln Asn Leu Phe Arg Ile Ala
                165                 170                 175

Asn Glu Gln Thr Thr Phe Ala Asp Ala Phe Lys Met Ala Asp Asp Val
            180                 185                 190

Leu His Ala Gly Val Arg Gly Val Thr Asp Leu Met Ile Met Pro Gly
```

```
            195                 200                 205
Leu Ile Asn Leu Asp Phe Ala Asp Ile Lys Ala Val Met Ser Glu Met
    210                 215                 220
Gly Lys Ala Met Met Gly Thr Gly Glu Asp Ser Gly Glu Asp Arg Ala
225                 230                 235                 240
Ile Lys Ala Ala Glu Ser Ala Ile Ser Asn Pro Leu Leu Asp His Ser
                245                 250                 255
Ser Met Cys Gly Ala Arg Gly Val Leu Ile Asn Ile Thr Gly Gly Pro
            260                 265                 270
Asp Met Thr Leu Phe Glu Val Asp Asn Ala Ala Asn Arg Ile Arg Glu
        275                 280                 285
Glu Val Asp Asn Ile Asp Ala Asn Ile Ile Phe Gly Ser Thr Phe Asn
    290                 295                 300
Pro Glu Leu Lys Gly Ile Ile Arg Val Ser Val Ala Thr Gly Ile
305                 310                 315                 320
Asp Ala Asp Lys Val Pro Lys Tyr Lys Leu Ala Ile Asp Lys Asn Thr
                325                 330                 335
Asn Thr Leu Pro Glu Glu Thr Tyr Asn Glu Ser Ile Ile Gln His Thr
            340                 345                 350
Gln Ile Glu Thr Ile Pro Ser Phe Asn Ser Tyr Ser Thr Glu Asn Ile
        355                 360                 365
Glu Ile Asn Glu Ser Ser Ile Lys Gln Asp Tyr Thr Gly Asn Glu Gln
    370                 375                 380
Glu Leu Arg Leu His Val Asn Ala Val Asn Lys Pro Glu Asn Asn Ser
385                 390                 395                 400
Gln Lys Ser Ser Phe Leu Gly Lys Ile Trp Glu Ser Leu Arg Thr Ser
                405                 410                 415
Asn Asn Gln Thr Leu Glu Arg Lys Asn Val Ile Val Asn Thr Val Asp
            420                 425                 430
Gln Asp Asn Lys Glu Ser Asp Ile His Asp Ile Pro Ala Phe Leu Arg
        435                 440                 445
Lys Lys Arg Asp
    450

<210> SEQ ID NO 15
<211> LENGTH: 508
<212> TYPE: PRT
<213> ORGANISM: Caulobacter crescentus

<400> SEQUENCE: 15

Met Ala Ile Ser Leu Ser Ala Pro Arg Thr Thr Glu Leu Lys Pro Arg
  1               5                  10                  15
Ile Val Val Phe Gly Val Gly Gly Ala Gly Gly Asn Ala Val Asn Asn
                 20                  25                  30
Met Ile Glu Ala Gly Leu Glu Gly Val Glu Phe Val Val Ala Asn Thr
             35                  40                  45
Asp Ala Gln Gln Leu Gln Phe Ala Lys Thr Asp Arg Arg Ile Gln Leu
         50                  55                  60
Gly Val Gln Ile Thr Gln Gly Leu Gly Ala Gly Ala His Pro Glu Val
 65                  70                  75                  80
Gly Met Ser Ala Ala Glu Glu Ser Phe Pro Glu Ile Gly Glu His Leu
                 85                  90                  95
Asp Gly Ala His Met Val Phe Ile Thr Ala Gly Met Gly Gly Gly Thr
                100                 105                 110
```

-continued

```
Gly Thr Gly Ala Ala Pro Ile Ile Ala Lys Cys Ala Arg Glu Arg Gly
        115                 120                 125
Ile Leu Thr Val Gly Val Val Thr Lys Pro Phe His Phe Glu Gly Arg
    130                 135                 140
His Arg Met Arg Leu Ala Asp Ser Gly Ile Gln Glu Leu Gln Arg Tyr
145                 150                 155                 160
Val Asp Thr Leu Ile Val Ile Pro Asn Gln Asn Leu Phe Arg Val Ala
                165                 170                 175
Asn Glu Arg Thr Thr Phe Ala Glu Ala Phe Gly Met Ala Asp Gln Val
            180                 185                 190
Leu His Ser Gly Val Arg Ser Ile Thr Asp Leu Met Val Leu Pro Gly
        195                 200                 205
Leu Ile Asn Leu Asp Phe Ala Asp Val Arg Thr Val Met Thr Glu Met
    210                 215                 220
Gly Lys Ala Met Met Gly Thr Gly Gly Thr Ala Glu Asp Arg Ala
225                 230                 235                 240
Leu Met Ala Ala Gln Asn Ala Ile Ala Asn Pro Leu Leu Asp Glu Val
                245                 250                 255
Ser Leu Lys Gly Ala Lys Ala Val Leu Val Asn Val Thr Gly Gly Met
            260                 265                 270
Asp Met Thr Leu Leu Glu Val Asp Glu Ala Ala Asn Ala Ile Ser Asp
        275                 280                 285
Gln Val Asp Pro Glu Ala Asn Ile Ile Phe Gly Ala Ala Phe Asp Pro
    290                 295                 300
Ser Leu Glu Gly Val Ile Arg Val Ser Val Val Ala Thr Gly Met Asp
305                 310                 315                 320
Gly Ala Ser Ile Ala Gln Ile Glu Pro Lys Pro Val Ser Arg Asn Ile
                325                 330                 335
Ser Ala Ala Pro Leu Ile Ala Glu Thr Ser Arg Pro Ala Pro Gln Pro
            340                 345                 350
Glu Pro Ala Arg Pro Thr Ala Arg Tyr Glu Ala Ala Arg Pro Ala Glu
        355                 360                 365
Arg Pro Val Ala Phe Ala Pro Glu Pro Ala Pro Glu Pro Glu Ile Val
    370                 375                 380
Met Ser Ala Pro Gln Pro Glu Pro Glu Ala Glu Leu Tyr Tyr Asp Glu
385                 390                 395                 400
Pro Thr Val Ala Glu Glu Pro Arg Val Ser Ala Ala Pro Ala Arg Ser
                405                 410                 415
Val Asn Arg Ile Val Asp Pro Leu Val Asp Asp Val Ala Glu Glu Pro
            420                 425                 430
Leu Phe Pro Glu Asn Asn Tyr Tyr Glu Glu Arg Arg Pro Gln Lys Gln
        435                 440                 445
Gly Gly Phe Phe Ser Met Phe Gly Gly Arg Gln Arg Tyr Glu Gln
    450                 455                 460
Gln Ala Ser Ala Pro Gln Ala Gln Ala Arg Ser Ala Gln Ser Ala Arg
465                 470                 475                 480
Pro Gln Leu Gln Pro Ile Glu Thr Pro Gln Ala Asp Asp Ala Glu Asp
                485                 490                 495
Leu Glu Ile Pro Ser Phe Leu Arg Arg Leu Ala Asn
            500                 505
```

<210> SEQ ID NO 16
<211> LENGTH: 407
<212> TYPE: PRT

<213> ORGANISM: Cyanidioschyzon merolae

<400> SEQUENCE: 16

| Met | Thr | Gly | Ala | Leu | Arg | Tyr | Arg | Ala | Leu | Ala | Arg | Val | Ile | Glu | Arg |
|---|---|---|---|---|---|---|---|---|---|---|---|---|---|---|---|
| 1 | | | | 5 | | | | | 10 | | | | | 15 | |

Cys Leu Gly Ser Arg Ala Leu Gly Glu Ser Gly Ser Ala Ala Ala Val
            20                  25                  30

Ser Asn Tyr Val Trp Gln Arg Glu Ala Ser Arg Gly Phe Val Leu Gly
        35                  40                  45

Thr Arg Leu Leu Pro Trp Cys Pro Leu Gly Ser Arg Leu Leu His Ser
50                  55                  60

Pro Ser Gln Thr Ala Ser Val Ile Arg Met Asn Thr Gly Ser Phe Ala
65                  70                  75                  80

Pro Lys Pro Asp Leu Gly Glu Gln Gln Pro Asn Thr Leu Thr Gly Gln
                85                  90                  95

Pro Arg Ile Met Val Val Gly Val Gly Gly Ala Gly Gly Asn Ala Val
            100                 105                 110

Asn Asn Met Ile Ala Ser Ser Leu Pro Gly Val Glu Phe Leu Val Ala
        115                 120                 125

Asn Thr Asp Ala Gln Ala Leu Lys Met Ser Leu Cys Pro Asn Arg Ile
    130                 135                 140

Gln Leu Gly Ala Ser Leu Thr Glu Gly Leu Gly Ala Gly Ala Arg Pro
145                 150                 155                 160

Asp Ile Gly Arg Ala Ala Ala Glu Glu Ala Tyr Glu Thr Leu Lys Arg
                165                 170                 175

Glu Phe Arg Gly Val His Leu Leu Phe Val Thr Ala Gly Met Gly Gly
            180                 185                 190

Gly Thr Gly Thr Gly Ala Ala Pro Ile Ile Ala Arg Ala Ala Ala Glu
        195                 200                 205

Leu Gly Cys Leu Thr Val Ala Val Val Thr Lys Pro Phe His Phe Glu
    210                 215                 220

Gly Met Ile Arg Met Lys Thr Ala Glu Gln Gly Ile Val Glu Leu Thr
225                 230                 235                 240

Glu His Val Asp Thr Met Leu Val Ile Pro Asn Gln Asn Leu Phe Lys
                245                 250                 255

Val Ala Ser Pro Arg Thr Ser Phe Leu Asp Ala Phe Arg Leu Ala Asp
            260                 265                 270

His Val Leu Tyr Ser Gly Val Arg Ser Ile Thr Asp Leu Met Thr Val
        275                 280                 285

Pro Gly Leu Ile Asn Leu Asp Phe Ala Asp Val Arg Ser Val Val Arg
    290                 295                 300

Glu Met Gly Arg Ala Met Met Gly Ser Gly Glu Val Glu Met Glu Ala
305                 310                 315                 320

Gly Asn Glu Glu Arg Ala Ile Arg Ala Ser Glu Ala Ala Ile Cys Asn
                325                 330                 335

Pro Leu Leu Asp Glu Thr Ser Leu Arg Gly Ala Arg Gly Val Leu Val
            340                 345                 350

Asn Ile Thr Gly Gly Thr Asp Met Thr Leu Phe Glu Ile Asp Ala Ala
        355                 360                 365

Ala Asn Arg Ile Arg Glu Gln Val Asp Pro Asp Ala Asn Ile Ile Phe
    370                 375                 380

Gly Ser Ala Phe Asp Ala Ser Met Gln Gly Arg Leu Arg Val Ser Val
385                 390                 395                 400

Leu Ala Thr Gly Ile Pro Ser
            405

<210> SEQ ID NO 17
<211> LENGTH: 401
<212> TYPE: PRT
<213> ORGANISM: Mallomonas splendens

<400> SEQUENCE: 17

Met Arg Ile Thr Gly Ala Asn Arg Ile Leu Ser Leu Ser Arg Ile Arg
 1               5                  10                  15

His Phe Ser Asp Gly Ala Ser Leu Asn Lys Ala Phe Leu Arg Ser Val
            20                  25                  30

Lys Pro Gly Val Lys Pro Glu Gln Tyr Asp Ser Arg Ser Gly Asn Ser
        35                  40                  45

Ser Gln Ala Gln Ser Thr Glu His Val Lys Asp Lys Phe Val Glu Pro
    50                  55                  60

Gly Asn Leu Arg Phe Arg Thr Gly Glu Tyr Ile Thr Glu Phe Leu Pro
65                  70                  75                  80

Lys Ile Cys Val Phe Gly Val Gly Gly Gly Cys Asn Ala Val Asn
                85                  90                  95

Asn Met Ile Ala Arg Lys Leu Ser Gly Val Glu Phe Val Cys Ala Asn
                100                 105                 110

Thr Asp Ala Gln His Leu Ser Thr Cys Leu Thr Glu Asn Lys Leu Gln
            115                 120                 125

Leu Gly Lys Glu Ser Thr Gln Gly Leu Gly Cys Gly Ala Asn Pro Glu
    130                 135                 140

Ser Gly Arg Arg Ala Ala Glu Glu Ser Lys Glu Glu Ile Ala Arg Tyr
145                 150                 155                 160

Ile Ala Asp Ala Asn Met Val Phe Ile Thr Ala Gly Met Gly Gly Gly
                165                 170                 175

Thr Gly Thr Gly Ala Ala Pro Val Val Ala Glu Val Cys Met Glu Lys
            180                 185                 190

Asp Ile Leu Thr Val Ala Val Thr Lys Pro Phe Ser Phe Glu Gly
        195                 200                 205

Lys His Arg Ala Arg Leu Ala Asn Glu Gly Ile Arg Ser Leu Glu Asp
    210                 215                 220

Arg Val Asp Thr Leu Ile Ile Pro Asn Gln Asn Ile Phe Lys Leu
225                 230                 235                 240

Ile Asn Ala Ser Thr Ser Met Ala Asp Ala Phe Gly Leu Ala Asp Asp
                245                 250                 255

Ile Leu Leu Ala Gly Val Lys Ser Ile Thr Asp Leu Met Val Arg Pro
            260                 265                 270

Gly Leu Ile Asn Leu Asp Phe Ala Asp Val Arg Thr Val Met Ser Gly
        275                 280                 285

Met Gly His Ala Ile Met Gly Thr Gly Gln Ala Glu Gly Glu Asp Arg
    290                 295                 300

Ala Ile Arg Ala Ala Asn Asp Ala Leu Asn Asn Pro Leu Leu Gly Gly
305                 310                 315                 320

Asp Phe Ser Val Arg Ser Ala Lys Gly Met Leu Val Asn Ile Thr Gly
                325                 330                 335

Gly Lys Asp Leu Thr Leu Val Glu Val Asp Ala Ala Gln Arg Ile
            340                 345                 350

Thr Ser Glu Ile Glu Asp Glu Asp Ala Asn Val Ile Phe Gly Ser Ser
        355                 360                 365

-continued

Phe Asp Glu Ser Leu Gln Gly Ser Ile Arg Val Ser Ile Val Ala Thr
        370                 375                 380

Gly Ile Glu Ala Pro Gly Ala Ala Ala Thr Ala Ala Pro Val Ile
385                 390                 395                 400

Arg

<210> SEQ ID NO 18
<211> LENGTH: 483
<212> TYPE: PRT
<213> ORGANISM: Gentiana lutea

<400> SEQUENCE: 18

Met Ala Thr Ser Thr Ser Pro Cys Phe Thr Pro Tyr Asp Ile Gln Ser
1               5                   10                  15

Pro Ser Arg Val Met Thr Thr Phe Gly Gly Arg Ile Ser Pro Met Lys
            20                  25                  30

Met Asn Leu Phe His Glu Lys Lys Val Phe Trp Val Phe Asp Gln Lys
        35                  40                  45

Gly Ser Arg Ile Tyr Pro His Phe Lys Cys Ser Thr Asn Ser His Asn
50                  55                  60

Val Asn Gln His Gln Ser Lys Asp Pro Phe Leu Asn Leu His Pro Glu
65                  70                  75                  80

Ile Ser Leu Leu Arg Gly Asp Gly Asn Asn Thr Leu Val Asp Ser Arg
                85                  90                  95

Val Asp Thr Ala Gly Ser Gly Arg Ser Val Thr Glu Ser Leu Arg Asp
            100                 105                 110

Ser Ser Ser Ser Asn Asn Tyr Ser Glu Ala Lys Ile Lys Val Val Gly
        115                 120                 125

Val Gly Gly Gly Gly Ser Asn Ala Val Asn Arg Met Ile Glu Ser Ala
130                 135                 140

Met Lys Gly Val Glu Phe Trp Ile Val Asn Thr Asp Val Gln Ala Ile
145                 150                 155                 160

Lys Met Ser Pro Val Tyr Leu Glu Asn Arg Leu Gln Ile Gly Gln Glu
                165                 170                 175

Leu Thr Arg Gly Leu Gly Ala Gly Gly Asn Pro Asp Ile Gly Met Asn
            180                 185                 190

Ala Ala Lys Glu Ser Lys Glu Ala Ile Glu Glu Ala Val Tyr Gly Ala
        195                 200                 205

Asp Met Val Phe Val Thr Ala Gly Met Gly Gly Gly Thr Gly Thr Gly
210                 215                 220

Gly Ala Pro Val Ile Ala Gly Ile Ala Lys Ser Met Gly Ile Leu Thr
225                 230                 235                 240

Val Gly Ile Val Thr Thr Pro Phe Ser Phe Glu Gly Arg Arg Arg Ala
                245                 250                 255

Val Gln Ala Gln Glu Gly Ile Ala Ala Leu Arg Asp Asn Val Asp Thr
            260                 265                 270

Leu Ile Val Ile Pro Asn Asp Lys Leu Leu Thr Ala Val Ser Pro Ser
        275                 280                 285

Thr Pro Val Thr Glu Ala Phe Asn Leu Ala Asp Asp Ile Leu Arg Gln
290                 295                 300

Gly Val Arg Gly Ile Ser Asp Ile Ile Thr Ile Pro Gly Leu Val Asn
305                 310                 315                 320

Val Asp Phe Ala Asp Val Arg Ala Ile Met Ala Asn Ala Gly Ser Ser
                325                 330                 335

-continued

```
Leu Met Gly Ile Gly Thr Ala Thr Gly Lys Thr Arg Ala Arg Asp Ala
            340                 345                 350

Ala Leu Asn Ala Ile Gln Ser Pro Leu Leu Asp Ile Gly Ile Glu Arg
            355                 360                 365

Ala Thr Gly Ile Val Trp Asn Ile Thr Gly Gly Ser Asp Leu Thr Leu
            370                 375                 380

Phe Glu Val Asn Ala Ala Ala Glu Val Ile Tyr Asp Leu Val Asp Pro
385                 390                 395                 400

Ser Ala Asn Leu Ile Phe Gly Ala Val Asp Pro Ser Leu Cys Gly
            405                 410                 415

Gln Val Ser Ile Thr Leu Ile Ala Thr Gly Phe Lys Arg Gln Glu Glu
            420                 425                 430

Ser Asp Lys Arg Ser Ile Gln Ala Gly Gly Gln Leu Ala Pro Gly Asp
            435                 440                 445

Ala Asn Gln Gly Ile Asn Arg Arg Pro Ser Ser Phe Ser Glu Ser Gly
            450                 455                 460

Ser Val Glu Ile Pro Glu Phe Leu Arg Lys Lys Gly Arg Ser Arg Tyr
465                 470                 475                 480

Pro Arg Ala

<210> SEQ ID NO 19
<211> LENGTH: 468
<212> TYPE: PRT
<213> ORGANISM: Nicotiana tabacum

<400> SEQUENCE: 19

Met Ala Thr Cys Thr Ser Ala Val Phe Met Pro Pro Asp Thr Arg Arg
1               5                   10                  15

Ser Arg Gly Val Leu Thr Leu Gly Gly Arg Leu Cys Ala Leu Lys
            20                  25                  30

Met Gln Asp Glu Lys Ile Gly Phe Leu Gly Val Asn Gln Lys Gly Ser
            35                  40                  45

Ser Ser Leu Pro Gln Phe Lys Cys Ser Ser Asn Ser His Ser Val Asn
            50                  55                  60

Gln Tyr Gln Asn Lys Asp Ser Phe Leu Asn Leu His Pro Glu Ile Ser
65                  70                  75                  80

Leu Leu Arg Gly Glu Glu Ser Ser Ser Gly Asn Val Thr Glu Ser Leu
            85                  90                  95

Met Asp Ser Ser Arg Ser Asn Asn Phe Asn Glu Ala Lys Ile Lys Val
            100                 105                 110

Val Gly Val Gly Gly Gly Gly Ser Asn Ala Val Asn Arg Met Ile Glu
            115                 120                 125

Ser Ser Met Lys Gly Val Glu Phe Trp Ile Val Asn Thr Asp Ile Gln
            130                 135                 140

Ala Met Arg Met Ser Pro Val Ala Glu Gln Arg Leu Pro Ile Gly
145                 150                 155                 160

Gln Glu Leu Thr Arg Gly Leu Gly Ala Gly Asn Pro Asp Ile Gly
            165                 170                 175

Met Asn Ala Ala Asn Glu Ser Lys Gln Ala Ile Glu Glu Ala Val Tyr
            180                 185                 190

Gly Ala Asp Met Val Phe Val Thr Ala Gly Met Gly Gly Gly Thr Gly
            195                 200                 205

Thr Gly Ala Ala Pro Ile Ile Ala Gly Thr Ala Lys Ser Met Gly Ile
            210                 215                 220
```

-continued

```
Leu Thr Val Gly Ile Val Thr Thr Pro Phe Ser Phe Glu Gly Arg Arg
225                 230                 235                 240

Arg Ala Val Gln Ala Gln Glu Gly Ile Ala Ala Leu Arg Glu Asn Val
            245                 250                 255

Asp Thr Leu Ile Val Ile Pro Asn Asp Lys Leu Leu Thr Ala Val Ser
        260                 265                 270

Pro Ser Thr Pro Val Thr Glu Ala Phe Asn Leu Ala Asp Asp Ile Leu
    275                 280                 285

Arg Gln Gly Val Arg Gly Ile Ser Asp Ile Ile Thr Ile Pro Gly Leu
290                 295                 300

Val Asn Val Asp Phe Ala Asp Val Arg Ala Ile Met Ala Asn Ala Gly
305                 310                 315                 320

Ser Ser Leu Met Gly Ile Gly Thr Ala Thr Gly Lys Thr Arg Ala Arg
            325                 330                 335

Asp Ala Ala Leu Asn Ala Ile Gln Ser Pro Leu Leu Asp Ile Gly Ile
        340                 345                 350

Glu Arg Ala Thr Gly Ile Val Trp Asn Ile Thr Gly Gly Ser Asp Leu
    355                 360                 365

Thr Leu Phe Glu Val Asn Ala Ala Glu Val Ile Tyr Asp Leu Val
370                 375                 380

Asp Pro Ser Ala Asn Leu Ile Phe Gly Ala Val Ile Asp Pro Ser Ile
385                 390                 395                 400

Ser Gly Gln Val Ser Ile Thr Leu Ile Ala Thr Gly Phe Lys Arg Gln
            405                 410                 415

Glu Glu Ser Asp Gly Arg Pro Leu Gln Gly Asn Gln Leu Thr Gln Gly
        420                 425                 430

Asp Val Ser Leu Gly Asn Asn Arg Arg Pro Ala Ser Phe Leu Glu Gly
    435                 440                 445

Gly Ser Val Glu Ile Pro Glu Phe Leu Arg Lys Gly Arg Ser Arg
450                 455                 460

Tyr Pro Arg Ala
465

<210> SEQ ID NO 20
<211> LENGTH: 397
<212> TYPE: PRT
<213> ORGANISM: Arabidopsis thaliana

<400> SEQUENCE: 20

Met Leu Arg Gly Glu Gly Thr Ser Thr Ile Val Asn Pro Arg Lys Glu
1               5                   10                  15

Thr Ser Ser Gly Pro Val Val Glu Asp Phe Glu Glu Pro Ser Ala Pro
            20                  25                  30

Ser Asn Tyr Asn Glu Ala Arg Ile Lys Val Ile Gly Val Gly Gly Gly
        35                  40                  45

Gly Ser Asn Ala Val Asn Arg Met Ile Glu Ser Glu Met Ser Gly Val
    50                  55                  60

Glu Phe Trp Ile Val Asn Thr Asp Ile Gln Ala Met Arg Met Ser Pro
65                  70                  75                  80

Val Leu Pro Asp Asn Arg Leu Gln Ile Gly Lys Glu Leu Thr Arg Gly
                85                  90                  95

Leu Gly Ala Gly Gly Asn Pro Glu Ile Gly Met Asn Ala Ala Arg Glu
            100                 105                 110

Ser Lys Glu Val Ile Glu Glu Ala Leu Tyr Gly Ser Asp Met Val Phe
```

-continued

```
                115                 120                 125
Val Thr Ala Gly Met Gly Gly Thr Gly Thr Gly Ala Ala Pro Val
    130                 135                 140
Ile Ala Gly Ile Ala Lys Ala Met Gly Ile Leu Thr Val Gly Ile Ala
145                 150                 155                 160
Thr Thr Pro Phe Ser Phe Glu Gly Arg Arg Thr Val Gln Ala Gln
                165                 170                 175
Glu Gly Leu Ala Ser Leu Arg Asp Asn Val Asp Thr Leu Ile Val Ile
                180                 185                 190
Pro Asn Asp Lys Leu Leu Thr Ala Val Ser Gln Ser Thr Pro Val Thr
                195                 200                 205
Glu Ala Phe Asn Leu Ala Asp Asp Ile Leu Arg Gln Gly Val Arg Gly
    210                 215                 220
Ile Ser Asp Ile Ile Thr Ile Pro Gly Leu Val Asn Val Asp Phe Ala
225                 230                 235                 240
Asp Val Arg Ala Ile Met Ala Asn Ala Gly Ser Ser Leu Met Gly Ile
                245                 250                 255
Gly Thr Ala Thr Gly Lys Ser Arg Ala Arg Asp Ala Ala Leu Asn Ala
                260                 265                 270
Ile Gln Ser Pro Leu Leu Asp Ile Gly Ile Glu Arg Ala Thr Gly Ile
    275                 280                 285
Val Trp Asn Ile Thr Gly Gly Ser Asp Leu Thr Leu Phe Glu Val Asn
    290                 295                 300
Ala Ala Ala Glu Val Ile Tyr Asp Leu Val Asp Pro Thr Ala Asn Leu
305                 310                 315                 320
Ile Phe Gly Ala Val Val Asp Pro Ala Leu Ser Gly Gln Val Ser Ile
                325                 330                 335
Thr Leu Ile Ala Thr Gly Phe Lys Arg Gln Glu Gly Glu Gly Arg
                340                 345                 350
Thr Val Gln Met Val Gln Ala Asp Ala Ala Ser Val Gly Ala Thr Arg
    355                 360                 365
Arg Pro Ser Ser Ser Phe Arg Glu Ser Gly Ser Val Glu Ile Pro Glu
370                 375                 380
Phe Leu Lys Lys Lys Gly Ser Ser Arg Tyr Pro Arg Val
385                 390                 395

<210> SEQ ID NO 21
<211> LENGTH: 458
<212> TYPE: PRT
<213> ORGANISM: Physcomitrella patens

<400> SEQUENCE: 21

Met Ala Leu Phe Ser Gly Cys Ser Gly Trp Ala Gly Leu Lys Val Ser
  1               5                  10                  15
Ser Arg Val Gly Gly Glu Ala Cys Arg Thr Pro Val His Cys
                20                  25                  30
Ser Met His Ser Arg Ser Ser Val Arg Ala Leu Arg Arg Ile Asp Arg
                35                  40                  45
Ala Leu Ser Asn Gly Gly Leu Cys Asn Phe Gly Glu Arg Asp Leu Leu
    50                  55                  60
Ala Leu Glu Ala Lys Ser Pro Leu Arg Cys Glu Pro Pro Ser Ser Val
65                  70                  75                  80
Met Arg Asn Pro Val Met Ala Phe Glu Gly Ser Gly Asp Asp Thr Gly
                85                  90                  95
```

-continued

```
Ser Tyr Asn Glu Ala Lys Ile Lys Val Ile Gly Val Gly Gly Gly
            100                 105                 110

Ser Asn Ala Val Asn Arg Met Leu Glu Ser Glu Met Gln Gly Val Glu
        115                 120                 125

Phe Trp Ile Val Asn Thr Asp Ala Gln Ala Met Ala Leu Ser Pro Val
    130                 135                 140

Pro Ala Gln Asn Arg Leu Gln Ile Gly Gln Lys Leu Thr Arg Gly Leu
145                 150                 155                 160

Gly Ala Gly Gly Asn Pro Glu Ile Gly Cys Ser Ala Ala Glu Glu Ser
                165                 170                 175

Lys Ala Met Val Glu Glu Ala Leu Arg Gly Ala Asp Met Val Phe Val
            180                 185                 190

Thr Ala Gly Met Gly Gly Gly Thr Gly Ser Gly Ala Ala Pro Ile Ile
        195                 200                 205

Ala Gly Val Ala Lys Gln Leu Gly Ile Leu Thr Val Gly Ile Val Thr
    210                 215                 220

Thr Pro Phe Ala Phe Glu Gly Arg Arg Arg Ala Val Gln Ala His Glu
225                 230                 235                 240

Gly Ile Ala Ala Leu Lys Asn Asn Val Asp Thr Leu Ile Thr Ile Pro
                245                 250                 255

Asn Asn Lys Leu Leu Thr Ala Val Ala Gln Ser Thr Pro Val Thr Glu
            260                 265                 270

Ala Phe Asn Leu Ala Asp Asp Ile Leu Arg Gln Gly Val Arg Gly Ile
        275                 280                 285

Ser Asp Ile Ile Thr Val Pro Gly Leu Val Asn Val Asp Phe Ala Asp
    290                 295                 300

Val Arg Ala Ile Met Ala Asn Ala Gly Ser Ser Leu Met Gly Ile Gly
305                 310                 315                 320

Thr Ala Thr Gly Lys Ser Arg Ala Arg Glu Ala Ala Leu Ser Ala Ile
                325                 330                 335

Gln Ser Pro Leu Leu Asp Val Gly Ile Glu Arg Ala Thr Gly Ile Val
            340                 345                 350

Trp Asn Ile Thr Gly Gly Ser Asp Met Thr Leu Phe Glu Val Asn Ala
        355                 360                 365

Ala Ala Glu Val Ile Tyr Asp Leu Val Asp Pro Asn Ala Asn Leu Ile
    370                 375                 380

Phe Gly Ala Val Val Asp Glu Ala Leu His Gly Gln Val Ser Ile Thr
385                 390                 395                 400

Leu Ile Ala Thr Gly Phe Ser Gln Asp Glu Pro Asp Ala Arg Ser
                405                 410                 415

Met Gln Asn Val Ser Arg Ile Leu Asp Gly Gln Ala Gly Arg Ser Pro
            420                 425                 430

Thr Gly Leu Ser Gln Gly Ser Asn Gly Ser Ala Ile Asn Ile Pro Ser
        435                 440                 445

Phe Leu Arg Lys Arg Gly Gln Thr Arg His
    450                 455
```

<210> SEQ ID NO 22
<211> LENGTH: 464
<212> TYPE: PRT
<213> ORGANISM: Physcomitrella patens

<400> SEQUENCE: 22

```
Met Ala Leu Leu Gly Ser Arg Ser Gly Leu Val Gly Leu Arg Val Ser
1               5                   10                  15
```

```
Ser Arg Val Gly Gly Glu Ser Arg Ile Val Pro Ala Thr Arg Asp
             20                  25                  30

Arg Phe Cys Val His Leu Arg Pro Ser Thr Arg Ala His Arg Arg Leu
         35                  40                  45

Asp Arg Thr Val Gly Asn Glu Ser Leu Cys Thr Pro Arg Glu Arg Asp
         50                  55                  60

Leu Ala Ala Glu Pro Lys Phe Leu His Thr Gly Trp Glu Ser Ser Ser
 65                  70                  75                  80

Ser Ser Ser Ser Ser Cys Glu Thr Gly Ile Pro Val Thr Ala Phe
                 85                  90                  95

Gly Gly Asn Gly Asp Glu Tyr Glu Ser Ser Asn Glu Ala Lys Ile Lys
             100                 105                 110

Val Ile Gly Val Gly Gly Gly Ser Asn Ala Val Asn Arg Met Leu
             115                 120                 125

Glu Ser Glu Met Gln Gly Val Glu Phe Trp Ile Val Asn Thr Asp Ala
         130                 135                 140

Gln Ala Met Ala Leu Ser Pro Val Pro Ala Gln Asn Arg Leu Gln Ile
145                 150                 155                 160

Gly Gln Lys Leu Thr Arg Gly Leu Gly Ala Gly Asn Pro Glu Ile
                 165                 170                 175

Gly Cys Ser Ala Ala Glu Glu Ser Lys Ala Met Val Glu Glu Ala Leu
             180                 185                 190

Arg Gly Ala Asp Met Val Phe Val Thr Ala Gly Met Gly Gly Gly Thr
         195                 200                 205

Gly Ser Gly Ala Ala Pro Ile Ile Ala Gly Val Ala Lys Gln Leu Gly
    210                 215                 220

Ile Leu Thr Val Gly Ile Val Thr Thr Pro Phe Ala Phe Glu Gly Arg
225                 230                 235                 240

Arg Arg Ser Val Gln Ala His Glu Gly Ile Ala Ala Leu Lys Asn Asn
                 245                 250                 255

Val Asp Thr Leu Ile Thr Ile Pro Asn Asn Lys Leu Leu Thr Ala Val
             260                 265                 270

Ala Gln Ser Thr Pro Val Thr Glu Ala Phe Asn Leu Ala Asp Asp Ile
         275                 280                 285

Leu Arg Gln Gly Val Arg Gly Ile Ser Asp Ile Ile Thr Val Pro Gly
    290                 295                 300

Leu Val Asn Val Asp Phe Ala Asp Val Arg Ala Ile Met Ala Asn Ala
305                 310                 315                 320

Gly Ser Ser Leu Met Gly Ile Gly Thr Ala Thr Gly Lys Ser Lys Ala
                 325                 330                 335

Arg Glu Ala Ala Leu Ser Ala Ile Gln Ser Pro Leu Leu Asp Val Gly
             340                 345                 350

Ile Glu Arg Ala Thr Gly Ile Val Trp Asn Ile Thr Gly Gly Ser Asp
         355                 360                 365

Met Thr Leu Phe Glu Val Asn Ala Ala Ala Glu Val Ile Tyr Asp Leu
    370                 375                 380

Val Asp Pro Asn Ala Asn Leu Ile Phe Gly Ala Val Val Asp Glu Ala
385                 390                 395                 400

Leu His Asp Gln Ile Ser Ile Thr Leu Ile Ala Thr Gly Phe Ser Ser
                 405                 410                 415

Gln Asp Asp Pro Asp Ala Arg Ser Met Gln Tyr Ala Ser Arg Val Leu
             420                 425                 430
```

Glu Gly Gln Ala Gly Arg Ser Ser Met Ala Ser Ser Arg Gly Gly Asn
            435                 440                 445

Ser Ser Thr Ile Asn Ile Pro Asn Phe Leu Arg Lys Arg Gly Gln Arg
    450                 455                 460

<210> SEQ ID NO 23
<211> LENGTH: 398
<212> TYPE: PRT
<213> ORGANISM: Guillardia theta

<400> SEQUENCE: 23

Met Tyr Phe Ile Gln Asn Ile Lys Cys Tyr Gln Phe Asp Lys Lys Asn
1               5                   10                  15

Ile Phe Lys Thr Ile Asn Lys Phe Arg Cys Arg Ser Gln Ser Leu Ile
            20                  25                  30

Lys Ser Asn Ile Ser Glu Asp Ser Phe Phe Asn Gln Glu Ile Ser Ser
        35                  40                  45

Ser Pro Cys Val Ile Lys Val Ile Gly Val Gly Gly Gly Gly Gly Asn
    50                  55                  60

Ala Val Asn Arg Met Val Gly Val Glu Gly Val Glu Phe Trp Ser
65              70                  75                  80

Ile Asn Thr Asp Ala Gln Ala Leu Ser Arg Ser Leu Ala Pro Asn Thr
            85                  90                  95

Cys Asn Ile Gly Ala Lys Leu Thr Arg Gly Leu Gly Ala Gly Gly Asn
            100                 105                 110

Pro Glu Ile Gly Arg Lys Ala Ala Glu Glu Ser Arg Asp Leu Ile Ala
            115                 120                 125

Glu Ala Val Ser Ala Gly Asp Leu Val Phe Val Thr Ala Gly Met Gly
    130                 135                 140

Gly Gly Thr Gly Ser Gly Ala Ala Pro Ile Val Ala Glu Val Ala Lys
145                 150                 155                 160

Glu Met Gly Cys Leu Thr Val Gly Val Val Thr Lys Pro Phe Ala Phe
            165                 170                 175

Glu Gly Lys Arg Arg Met Gln Gln Ala Asn Asp Ala Ile Leu Asn Leu
            180                 185                 190

Arg Asn Lys Val Asp Thr Leu Ile Val Val Ser Asn Asp Lys Leu Leu
        195                 200                 205

Gln Ile Val Pro Asp Asn Thr Pro Leu Gln Asp Ala Phe Ser Val Ala
    210                 215                 220

Asp Asp Ile Leu Arg Gln Gly Val Val Gly Ile Ser Glu Ile Ile Val
225                 230                 235                 240

Arg Pro Gly Leu Ile Asn Val Asp Phe Ala Asp Val Arg Ser Val Met
            245                 250                 255

Ala Asp Ala Gly Ser Ala Leu Met Gly Ile Gly Thr Gly Ser Gly Lys
            260                 265                 270

Thr Arg Ala Gln Asp Ala Ala Val Ala Ile Ser Ser Pro Leu Leu
    275                 280                 285

Asp Phe Pro Ile Glu Lys Ala Arg Gly Ile Val Phe Asn Ile Thr Gly
    290                 295                 300

Gly Gln Asp Met Thr Leu His Glu Ile Asn Ser Ala Ala Glu Val Ile
305                 310                 315                 320

Tyr Glu Ala Val Asp Ser Asn Ala Asn Ile Ile Phe Gly Ala Leu Val
            325                 330                 335

Asp Asp Asn Met Glu Asn Glu Ile Ser Ile Thr Val Val Ala Thr Gly
            340                 345                 350

-continued

Phe Thr Gln Pro Asn Asp Ser Lys Phe Phe Ser Thr Lys Ser Ala Val
        355                 360                 365

Asp Phe Ser Lys Ile Tyr Asp Asn Lys Lys Thr Lys Ser Thr Tyr Lys
        370                 375                 380

Glu Ser Arg Ala Glu Phe Ser Asp Leu Trp Lys Lys Phe Tyr
385                 390                 395

<210> SEQ ID NO 24
<211> LENGTH: 368
<212> TYPE: PRT
<213> ORGANISM: Mallomonas splendens

<400> SEQUENCE: 24

Gly Val Glu Leu Trp Val Val Asn Thr Asp Ala Gln Ala Leu Ser Arg
1               5                   10                  15

Ser Ser Ala Lys Arg Arg Leu Asn Ile Gly Lys Val Leu Ser Arg Gly
            20                  25                  30

Leu Gly Ala Gly Gly Asn Pro Ala Ile Gly Ala Lys Ala Ala Glu Glu
        35                  40                  45

Ser Arg Glu Glu Ile Met Ala Val Val Lys Asn Ala Asp Leu Val Phe
    50                  55                  60

Val Thr Ala Gly Met Gly Gly Thr Gly Ser Gly Ala Ala Pro Val
65                  70                  75                  80

Val Ala Glu Cys Ala Lys Glu Ala Gly Ala Leu Thr Val Gly Val Val
                85                  90                  95

Thr Lys Pro Phe Gly Phe Glu Gly Arg Lys Arg Met Gln Gln Ala Arg
            100                 105                 110

Asn Ala Ile Leu Glu Met Lys Asp Lys Val Asp Thr Leu Ile Val Val
        115                 120                 125

Ser Asn Asp Lys Leu Leu Lys Ile Val Pro Asp Asn Thr Pro Leu Thr
    130                 135                 140

Glu Ala Phe Leu Val Ala Asp Asp Ile Leu Arg Gln Gly Val Val Gly
145                 150                 155                 160

Ile Thr Glu Ile Ile Val Lys Pro Gly Leu Val Asn Val Asp Phe Ala
                165                 170                 175

Asp Val Arg Thr Ile Met Gly Asn Ala Gly Thr Ala Leu Met Gly Ile
            180                 185                 190

Gly His Gly Lys Gly Lys Asn Arg Ala Lys Asp Ala Ala Leu Ser Ala
        195                 200                 205

Ile Ser Ser Pro Leu Leu Asp Phe Pro Ile Thr Arg Ala Lys Gly Ile
    210                 215                 220

Val Phe Asn Ile Val Gly Gly Ser Asp Met Ser Leu Gln Glu Ile Asn
225                 230                 235                 240

Ala Ala Ala Glu Val Ile Tyr Glu Asn Val Asp Gln Asp Ala Asn Ile
                245                 250                 255

Ile Phe Gly Ala Met Val Asp Asp Lys Met Thr Ser Gly Glu Val Ser
            260                 265                 270

Ile Thr Val Leu Ala Thr Gly Phe Ser Thr Asp Tyr Phe Ser Asn Asp
        275                 280                 285

Gly Ser Gly Leu Glu Asn Leu Pro Pro Asn Arg Leu Ser Pro Pro Lys
    290                 295                 300

Thr Val Gly Ser Ala Lys Ser Tyr Ser Glu Tyr Glu Pro Pro Ser Thr
305                 310                 315                 320

Pro Lys Ala Glu Glu Arg Asp Ser Glu Tyr Leu Ser Ala Asp Asp Leu

```
                   325                 330                 335
Thr Asp Glu Ser Lys Glu Arg Asp Gln Asp Gly Lys Lys Asp Glu Glu
                340                 345                 350
Lys Pro Lys Gly Gly Phe Arg Gly Phe Ile Lys Arg Leu Phe Ser
                355                 360                 365

<210> SEQ ID NO 25
<211> LENGTH: 428
<212> TYPE: PRT
<213> ORGANISM: Anabaena PCC7120

<400> SEQUENCE: 25

Met Thr Leu Asp Asn Asn Gln Glu Leu Thr Tyr Arg Asn Ser Gln Ser
  1               5                  10                  15
Leu Gly Gln Pro Gly Phe Ser Leu Ala Val Asn Ser Ser Asn Pro Phe
                 20                  25                  30
Asn His Ser Gly Leu Asn Phe Gly Gln Asn Asn Asp Ser Lys Lys Ile
             35                  40                  45
Ser Val Glu Asn Asn Arg Ile Gly Glu Ile Val Pro Gly Arg Val Ala
         50                  55                  60
Asn Ile Lys Val Ile Gly Val Gly Gly Gly Gly Asn Ala Val Asn
 65                  70                  75                  80
Arg Met Ile Glu Ser Asp Val Ser Gly Val Glu Phe Trp Ser Ile Asn
                 85                  90                  95
Thr Asp Ala Gln Ala Leu Thr Leu Ala Gly Ala Pro Ser Arg Leu Gln
                100                 105                 110
Ile Gly Gln Lys Leu Thr Arg Gly Leu Gly Ala Gly Gly Asn Pro Ala
            115                 120                 125
Ile Gly Gln Lys Ala Ala Glu Glu Ser Arg Asp Glu Ile Ala Thr Ala
        130                 135                 140
Leu Glu Gly Ala Asp Leu Val Phe Ile Thr Ala Gly Met Gly Gly Gly
145                 150                 155                 160
Thr Gly Thr Gly Ala Ala Pro Ile Val Ala Glu Val Ala Lys Glu Met
                165                 170                 175
Gly Ala Leu Thr Val Gly Val Val Thr Arg Pro Phe Val Phe Glu Gly
            180                 185                 190
Arg Arg Arg Thr Ser Gln Ala Glu Gln Gly Ile Glu Gly Leu Lys Ser
        195                 200                 205
Arg Val Asp Thr Leu Ile Ile Ile Pro Asn Asn Lys Leu Leu Glu Val
    210                 215                 220
Ile Pro Glu Gln Thr Pro Val Gln Glu Ala Phe Arg Tyr Ala Asp Asp
225                 230                 235                 240
Val Leu Arg Gln Gly Val Gln Gly Ile Ser Asp Ile Thr Ile Pro
                245                 250                 255
Gly Leu Val Asn Val Asp Phe Ala Asp Val Arg Ala Val Met Ala Asp
            260                 265                 270
Ala Gly Ser Ala Leu Met Gly Ile Gly Val Ser Ser Gly Lys Ser Arg
        275                 280                 285
Ala Arg Glu Ala Ala Ile Ala Ala Ile Ser Ser Pro Leu Leu Glu Cys
    290                 295                 300
Ser Ile Glu Gly Ala Arg Gly Val Val Phe Asn Ile Thr Gly Gly Ser
305                 310                 315                 320
Asp Leu Thr Leu His Glu Val Asn Ala Ala Glu Thr Ile Tyr Glu
                325                 330                 335
```

```
Val Val Asp Pro Asn Ala Asn Ile Ile Phe Gly Ala Val Ile Asp Asp
            340                 345                 350

Arg Leu Gln Gly Glu Val Arg Ile Thr Val Ile Ala Thr Gly Phe Thr
        355                 360                 365

Gly Glu Ile Gln Ala Ala Pro Gln Gln Asn Ala Ala Asn Ala Arg Val
    370                 375                 380

Val Ser Ala Pro Pro Lys Arg Thr Pro Thr Gln Thr Pro Leu Thr Asn
385                 390                 395                 400

Ser Pro Ala Pro Thr Pro Glu Pro Lys Glu Lys Ser Gly Leu Asp Ile
                405                 410                 415

Pro Asp Phe Leu Gln Arg Arg Arg Pro Pro Lys Asn
            420                 425

<210> SEQ ID NO 26
<211> LENGTH: 430
<212> TYPE: PRT
<213> ORGANISM: Synechocystis PCC6803

<400> SEQUENCE: 26

Met Thr Leu Asn Asn Asp Leu Pro Leu Asn Asn Ile Gly Phe Thr Gly
  1               5                  10                  15

Ser Gly Leu Asn Asp Gly Thr Glu Gly Leu Asp Asp Leu Phe Ser Ser
            20                  25                  30

Ser Ile Val Asp Asn Glu Pro Leu Glu Ala Leu Val Glu Thr Pro Thr
        35                  40                  45

Phe Ala Ser Pro Ser Pro Asn Leu Lys Arg Asp Gln Ile Val Pro Ser
 50                  55                  60

Asn Ile Ala Lys Ile Lys Val Ile Gly Val Gly Gly Gly Gly Cys Asn
 65                  70                  75                  80

Ala Val Asn Arg Met Ile Ala Ser Gly Val Thr Gly Ile Asp Phe Trp
                85                  90                  95

Ala Ile Asn Thr Asp Ser Gln Ala Leu Thr Asn Thr Asn Ala Pro Asp
            100                 105                 110

Cys Ile Gln Ile Gly Gln Lys Leu Thr Arg Gly Leu Gly Ala Gly Gly
        115                 120                 125

Asn Pro Ala Ile Gly Gln Lys Ala Ala Glu Glu Ser Arg Asp Glu Ile
    130                 135                 140

Ala Arg Ser Leu Glu Gly Thr Asp Leu Val Phe Ile Thr Ala Gly Met
145                 150                 155                 160

Gly Gly Gly Thr Gly Thr Gly Ala Ala Pro Ile Val Ala Glu Val Ala
                165                 170                 175

Lys Glu Met Gly Cys Leu Thr Val Gly Ile Val Thr Arg Pro Phe Thr
            180                 185                 190

Phe Glu Gly Arg Arg Arg Ala Lys Gln Ala Glu Glu Gly Ile Asn Ala
        195                 200                 205

Leu Gln Ser Arg Val Asp Thr Leu Ile Val Ile Pro Asn Asn Gln Leu
    210                 215                 220

Leu Ser Val Ile Pro Ala Glu Thr Pro Leu Gln Glu Ala Phe Arg Val
225                 230                 235                 240

Ala Asp Asp Ile Leu Arg Gln Gly Val Gln Gly Ile Ser Asp Ile Ile
                245                 250                 255

Ile Ile Pro Gly Leu Val Asn Val Asp Phe Ala Asp Val Arg Ala Val
            260                 265                 270

Met Ala Asp Ala Gly Ser Ala Leu Met Gly Ile Gly Val Gly Ser Gly
        275                 280                 285
```

```
Lys Ser Arg Ala Lys Glu Ala Thr Ala Ala Ile Ser Ser Pro Leu
    290                 295                 300

Leu Glu Ser Ser Ile Gln Gly Ala Lys Gly Val Val Phe Asn Val Thr
305                 310                 315                 320

Gly Gly Thr Asp Leu Thr Leu His Glu Val Asn Val Ala Ala Glu Ile
                325                 330                 335

Ile Tyr Glu Val Val Asp Ala Asp Ala Asn Ile Ile Phe Gly Ala Val
            340                 345                 350

Ile Asp Asp Arg Leu Gln Gly Glu Met Arg Ile Thr Val Ile Ala Thr
        355                 360                 365

Gly Phe Asn Gly Glu Lys Glu Lys Pro Gln Ala Lys Thr Ser Ser Lys
    370                 375                 380

Pro Val Leu Ser Gly Pro Ala Gly Val Glu Thr Val Pro Ser Thr
385                 390                 395                 400

Thr Thr Pro Glu Asp Pro Leu Gly Glu Ile Pro Met Ala Pro Glu Leu
                405                 410                 415

Asp Ile Pro Asp Phe Leu Gln Lys Arg Arg Phe Pro Arg Arg
            420                 425                 430

<210> SEQ ID NO 27
<211> LENGTH: 433
<212> TYPE: PRT
<213> ORGANISM: Arabidopsis thaliana

<400> SEQUENCE: 27

Met Ala Ile Ile Pro Leu Ala Gln Leu Asn Glu Leu Thr Ile Ser Ser
1               5                   10                  15

Ser Ser Ser Ser Phe Leu Thr Lys Ser Ile Ser Ser His Ser Leu His
            20                  25                  30

Ser Ser Cys Ile Cys Ala Ser Ser Arg Ile Ser Gln Phe Arg Gly Gly
        35                  40                  45

Phe Ser Lys Arg Arg Ser Asp Ser Thr Arg Ser Lys Ser Met Arg Leu
    50                  55                  60

Arg Cys Ser Phe Ser Pro Met Glu Ser Ala Arg Ile Lys Val Ile Gly
65                  70                  75                  80

Val Gly Gly Gly Gly Asn Asn Ala Val Asn Arg Met Ile Ser Ser Gly
                85                  90                  95

Leu Gln Ser Val Asp Phe Tyr Ala Ile Asn Thr Asp Ser Gln Ala Leu
            100                 105                 110

Leu Gln Phe Ser Ala Glu Asn Pro Leu Gln Ile Gly Glu Leu Leu Thr
        115                 120                 125

Arg Gly Leu Gly Thr Gly Gly Asn Pro Leu Leu Gly Glu Gln Ala Ala
    130                 135                 140

Glu Glu Ser Lys Asp Ala Ile Ala Asn Ala Leu Lys Gly Ser Asp Leu
145                 150                 155                 160

Val Phe Ile Thr Ala Gly Met Gly Gly Gly Thr Gly Ser Gly Ala Ala
                165                 170                 175

Pro Val Val Ala Gln Ile Ser Lys Asp Ala Gly Tyr Leu Thr Val Gly
            180                 185                 190

Val Val Thr Tyr Pro Phe Ser Phe Glu Gly Arg Lys Arg Ser Leu Gln
        195                 200                 205

Ala Leu Glu Ala Ile Glu Lys Leu Gln Lys Asn Val Asp Thr Leu Ile
    210                 215                 220

Val Ile Pro Asn Asp Arg Leu Leu Asp Ile Ala Asp Glu Gln Thr Pro
```

```
                225                 230                 235                 240
Leu Gln Asp Ala Phe Leu Leu Ala Asp Asp Val Leu Arg Gln Gly Val
                245                 250                 255
Gln Gly Ile Ser Asp Ile Ile Thr Ile Pro Gly Leu Val Asn Val Asp
                260                 265                 270
Phe Ala Asp Val Lys Ala Val Met Lys Asp Ser Gly Thr Ala Met Leu
                275                 280                 285
Gly Val Gly Val Ser Ser Lys Asn Arg Ala Glu Ala Ala Glu
                290                 295                 300
Gln Ala Thr Leu Ala Pro Leu Ile Gly Ser Ser Ile Gln Ser Ala Thr
305                 310                 315                 320
Gly Val Val Tyr Asn Ile Thr Gly Gly Lys Asp Ile Thr Leu Gln Glu
                325                 330                 335
Val Asn Arg Val Ser Gln Val Val Thr Ser Leu Ala Asp Pro Ser Ala
                340                 345                 350
Asn Ile Ile Phe Gly Ala Val Asp Asp Arg Tyr Thr Gly Glu Ile
                355                 360                 365
His Val Thr Ile Ile Ala Thr Gly Phe Ser Gln Ser Phe Gln Lys Thr
                370                 375                 380
Leu Leu Thr Asp Pro Arg Ala Ala Lys Leu Leu Asp Lys Met Gly Ser
385                 390                 395                 400
Ser Gly Gln Gln Glu Asn Lys Gly Met Ser Leu Pro His Gln Lys Gln
                405                 410                 415
Ser Pro Ser Thr Ile Ser Thr Lys Ser Ser Ser Pro Arg Arg Leu Phe
                420                 425                 430
Phe

<210> SEQ ID NO 28
<211> LENGTH: 423
<212> TYPE: PRT
<213> ORGANISM: Pisum sativum

<400> SEQUENCE: 28

Met Ala Thr Leu Leu Pro Ser Thr Ile Ser Asn Pro Asn Lys Leu Thr
1               5                   10                  15
Ser Tyr Ser Ser Leu Phe His Asn Ala Ser Leu Ser Thr Ser Pro Ser
                20                  25                  30
Ser Leu Thr Thr Thr Ser Val Ser Ile Tyr Pro Lys Thr Gln Arg Phe
            35                  40                  45
Gly Arg Arg Phe Gly Ser Val Arg Cys Ser Leu Ala Tyr Val Asp Asn
        50                  55                  60
Ala Lys Ile Lys Val Val Gly Ile Gly Gly Gly Asn Asn Ala Val
65                  70                  75                  80
Asn Arg Met Ile Gly Ser Gly Leu Gln Gly Val Asp Phe Tyr Ala Ile
                85                  90                  95
Asn Thr Asp Ala Gln Ala Leu Leu His Ser Ala Glu Asn Pro Ile
                100                 105                 110
Lys Ile Gly Glu Leu Leu Thr Arg Gly Leu Gly Thr Gly Gly Asn Pro
            115                 120                 125
Leu Leu Gly Glu Gln Ala Ala Glu Glu Ser Lys Glu Ala Ile Ala Asn
        130                 135                 140
Ala Leu Lys Gly Ser Asp Leu Val Phe Ile Thr Ala Gly Met Gly Gly
145                 150                 155                 160
Gly Thr Gly Ser Gly Ala Ala Pro Val Val Ala Gln Ile Ser Lys Glu
```

-continued

```
                165                 170                 175
Ala Gly Tyr Leu Thr Val Gly Val Val Thr Tyr Pro Phe Ser Phe Glu
            180                 185                 190

Gly Arg Lys Arg Ser Leu Gln Ala Leu Glu Ala Ile Glu Lys Leu Gln
        195                 200                 205

Lys Asn Val Asp Thr Leu Ile Val Ile Pro Asn Asp Arg Leu Leu Asp
    210                 215                 220

Ile Ala Asp Glu Gln Met Pro Leu Gln Asp Ala Phe Arg Leu Ala Asp
225                 230                 235                 240

Asp Val Leu Arg Gln Gly Val Gln Gly Ile Ser Asp Ile Ile Thr Ile
            245                 250                 255

Pro Gly Leu Val Asn Val Asp Phe Ala Asp Val Lys Ala Val Met Lys
        260                 265                 270

Asp Ser Gly Thr Ala Met Leu Gly Val Gly Val Ser Ser Gly Lys Asn
    275                 280                 285

Arg Ala Glu Glu Ala Ala Glu Gln Ala Thr Leu Ala Pro Leu Ile Gly
290                 295                 300

Ser Ser Ile Gln Ser Ala Thr Gly Val Val Tyr Asn Ile Thr Gly Gly
305                 310                 315                 320

Lys Asp Ile Thr Leu Gln Glu Val Asn Arg Val Ser Gln Val Val Thr
            325                 330                 335

Ser Leu Ala Asp Pro Ser Ala Asn Ile Ile Phe Gly Ala Val Val Asp
            340                 345                 350

Asp Arg Tyr Thr Gly Glu Ile His Val Thr Ile Ile Ala Thr Gly Phe
        355                 360                 365

Ser Gln Ser Phe Gln Lys Lys Leu Leu Thr Asp Pro Arg Ala Ala Lys
    370                 375                 380

Leu Leu Asp Lys Val Ala Glu Gly Lys Glu Ser Lys Thr Val Pro Pro
385                 390                 395                 400

Pro Leu Lys Ser Ser Asn Phe Ser Ser Lys Val Glu Ser Arg Pro Pro
            405                 410                 415

Pro Pro Arg Lys Leu Phe Phe
        420

<210> SEQ ID NO 29
<211> LENGTH: 413
<212> TYPE: PRT
<213> ORGANISM: Nicotiana tabacum

<400> SEQUENCE: 29

Met Ala Thr Ile Ser Asn Pro Ala Glu Ile Ala Ala Ser Ser Pro Ser
1               5                   10                  15

Phe Ala Phe Tyr His Ser Ser Phe Ile Pro Lys Gln Cys Cys Phe Thr
            20                  25                  30

Lys Ala Arg Arg Lys Ser Leu Cys Lys Pro Gln Arg Phe Ser Ile Ser
        35                  40                  45

Ser Ser Phe Thr Pro Phe Asp Ser Ala Lys Ile Lys Val Ile Gly Val
    50                  55                  60

Gly Gly Gly Gly Asn Asn Ala Val Asn Arg Met Ile Gly Ser Gly Leu
65                  70                  75                  80

Gln Gly Val Asp Phe Tyr Ala Ile Asn Thr Asp Ala Gln Ala Leu Leu
            85                  90                  95

Gln Ser Ala Ala Glu Asn Pro Leu Gln Ile Gly Glu Leu Leu Thr Arg
            100                 105                 110
```

```
Gly Leu Gly Thr Gly Gly Asn Pro Leu Leu Gly Glu Gln Ala Ala Glu
            115                 120                 125

Glu Ser Lys Glu Ala Ile Ala Asn Ser Leu Lys Gly Ser Asp Met Val
130                 135                 140

Phe Ile Thr Ala Gly Met Gly Gly Thr Gly Ser Gly Ala Ala Pro
145                 150                 155                 160

Val Val Ala Gln Ile Ala Lys Glu Ala Gly Tyr Leu Thr Val Gly Val
                165                 170                 175

Val Thr Tyr Pro Phe Ser Phe Glu Gly Arg Lys Arg Ser Val Gln Ala
                180                 185                 190

Leu Glu Ala Ile Glu Lys Leu Gln Lys Asn Val Asp Thr Leu Ile Val
            195                 200                 205

Ile Pro Asn Asp Arg Leu Leu Asp Ile Ala Asp Glu Gln Thr Pro Leu
210                 215                 220

Gln Asp Ala Phe Leu Leu Ala Asp Asp Val Leu Arg Gln Gly Val Gln
225                 230                 235                 240

Gly Ile Ser Asp Ile Ile Thr Ile Pro Gly Leu Val Asn Val Asp Phe
                245                 250                 255

Ala Asp Val Lys Ala Val Met Lys Asp Ser Gly Thr Ala Met Leu Gly
            260                 265                 270

Val Gly Val Ser Ser Ser Lys Asn Arg Ala Glu Glu Ala Ala Glu Gln
            275                 280                 285

Ala Thr Leu Ala Pro Leu Ile Gly Ser Ser Ile Gln Ser Ala Thr Gly
290                 295                 300

Val Val Tyr Asn Ile Thr Gly Gly Lys Asp Ile Thr Leu Gln Glu Val
305                 310                 315                 320

Asn Arg Val Ser Gln Val Val Thr Ser Leu Ala Asp Pro Ser Ala Asn
                325                 330                 335

Ile Ile Phe Gly Ala Val Val Asp Glu Arg Tyr Asn Gly Glu Ile His
            340                 345                 350

Val Thr Ile Ile Ala Thr Gly Phe Thr Gln Ser Phe Gln Lys Thr Leu
            355                 360                 365

Leu Ser Asp Pro Arg Gly Ala Lys Leu Ala Asp Lys Gly Pro Val Ile
370                 375                 380

Gln Glu Ser Met Ala Ser Pro Val Thr Leu Arg Ser Ser Thr Ser Pro
385                 390                 395                 400

Ser Thr Thr Ser Arg Thr Pro Thr Arg Arg Leu Phe Phe
                405                 410

<210> SEQ ID NO 30
<211> LENGTH: 419
<212> TYPE: PRT
<213> ORGANISM: Nicotiana tabacum

<400> SEQUENCE: 30

Met Ala Thr Met Leu Gly Leu Ser Asn Pro Ala Glu Ile Ala Ala Ser
1               5                   10                  15

Ser Pro Ser Ser Thr Ser Phe Ala Phe Tyr His Ser Ser Phe Ile Pro
                20                  25                  30

Lys Gln Cys Cys Phe Thr Lys Ala Arg Arg Lys Ser Leu Cys Lys Pro
            35                  40                  45

Gln Arg Phe Ser Ile Ser Ser Ser Phe Thr Pro Phe Asp Ser Ala Lys
        50                  55                  60

Ile Lys Val Ile Gly Val Gly Gly Gly Asn Asn Ala Val Asn Arg
65                  70                  75                  80
```

```
Met Ile Gly Ser Gly Leu Gln Gly Val Asp Phe Tyr Ala Ile Asn Thr
                85                  90                  95
Asp Ala Gln Ala Leu Leu Gln Ser Ala Ala Glu Asn Pro Leu Gln Ile
            100                 105                 110
Gly Glu Leu Leu Thr Arg Gly Leu Gly Thr Gly Gly Asn Pro Leu Leu
        115                 120                 125
Gly Glu Gln Ala Ala Glu Glu Ser Lys Glu Ala Ile Ala Asn Ser Leu
    130                 135                 140
Lys Gly Ser Asp Met Val Phe Ile Thr Ala Gly Met Gly Gly Thr
145                 150                 155                 160
Gly Ser Gly Ala Ala Pro Val Val Ala Gln Ile Ala Lys Glu Ala Gly
                165                 170                 175
Tyr Leu Thr Val Gly Val Val Thr Tyr Pro Phe Ser Phe Glu Gly Arg
            180                 185                 190
Lys Arg Ser Val Gln Ala Leu Glu Ala Ile Glu Lys Leu Gln Lys Asn
        195                 200                 205
Val Asp Thr Leu Ile Val Ile Pro Asn Asp Arg Leu Leu Asp Ile Ala
    210                 215                 220
Asp Glu Gln Thr Pro Leu Gln Asp Ala Phe Leu Leu Ala Asp Asp Val
225                 230                 235                 240
Leu Arg Gln Gly Val Gln Gly Ile Ser Asp Ile Thr Ile Pro Gly
                245                 250                 255
Leu Val Asn Val Asp Phe Ala Asp Val Lys Ala Val Met Lys Asp Ser
            260                 265                 270
Gly Thr Ala Met Leu Gly Val Gly Val Ser Ser Lys Asn Arg Ala
        275                 280                 285
Glu Glu Ala Ala Glu Gln Ala Thr Leu Ala Pro Leu Ile Gly Ser Ser
    290                 295                 300
Ile Gln Ser Ala Thr Gly Val Val Tyr Asn Ile Thr Gly Gly Lys Asp
305                 310                 315                 320
Ile Thr Leu Gln Glu Val Asn Arg Val Ser Gln Val Val Thr Ser Leu
                325                 330                 335
Ala Asp Pro Ser Ala Asn Ile Ile Phe Gly Ala Val Val Asp Glu Arg
            340                 345                 350
Tyr Asn Gly Glu Ile His Val Thr Ile Ala Thr Gly Phe Thr Gln
        355                 360                 365
Ser Phe Gln Lys Thr Leu Leu Ser Asp Pro Arg Gly Ala Lys Leu Ala
    370                 375                 380
Asp Lys Gly Pro Val Ile Gln Glu Ser Met Ala Ser Pro Val Thr Leu
385                 390                 395                 400
Arg Ser Ser Thr Ser Pro Ser Thr Thr Ser Arg Thr Pro Thr Arg Arg
                405                 410                 415
Leu Phe Phe

<210> SEQ ID NO 31
<211> LENGTH: 408
<212> TYPE: PRT
<213> ORGANISM: Nicotiana tabacum

<400> SEQUENCE: 31

Gly Leu Ser Ser Asn Thr Gly Ile Asp Ile Leu Ser Ser Ser Ser Asn
1               5                   10                  15
Ser Leu Ser Phe Tyr His Ser Thr Arg Phe Thr Gln Cys Phe Ser Pro
            20                  25                  30
```

```
Lys Ser Leu Cys Lys Arg Gln Arg Arg Phe Ser Ile Cys Ser Ser
             35                  40                  45

Leu Ser Ser Ala Lys Ile Lys Val Val Gly Val Gly Gly Gly Asn
 50                  55                  60

Asn Ala Val Asn Arg Met Ile Gly Ser Gly Leu Gln Gly Val Asp Phe
 65                  70                  75                  80

Tyr Ala Val Asn Thr Asp Ala Gln Ala Leu Leu Gln Ser Thr Val Glu
                 85                  90                  95

Asn Pro Ile Gln Ile Gly Glu Leu Leu Thr Arg Gly Leu Gly Thr Gly
                100                 105                 110

Gly Asn Pro Leu Leu Gly Glu Gln Ala Ala Glu Ser Lys Glu His
         115                 120                 125

Ile Ala Asn Ala Leu Lys Gly Ser Asp Met Val Phe Ile Thr Ala Gly
         130                 135                 140

Met Gly Gly Gly Thr Gly Ser Gly Ala Ala Pro Val Val Ala Gln Ile
145                 150                 155                 160

Ala Lys Glu Ala Gly Tyr Leu Thr Val Gly Val Val Thr Tyr Pro Phe
                165                 170                 175

Ser Phe Glu Gly Arg Lys Arg Ser Leu Gln Ala Leu Glu Ala Ile Glu
                180                 185                 190

Lys Leu Gln Lys Asn Val Asp Thr Leu Ile Val Ile Pro Asn Asp Arg
        195                 200                 205

Leu Leu Asp Ile Ala Asp Glu Gln Thr Pro Leu Gln Asn Ala Phe Leu
    210                 215                 220

Leu Ala Asp Asp Val Leu Cys Gln Gly Val Gln Gly Ile Ser Asp Ile
225                 230                 235                 240

Ile Thr Ile Pro Gly Leu Val Asn Val Asp Phe Ala Asp Val Lys Ala
                245                 250                 255

Ile Met Lys Asp Ser Gly Thr Ala Met Leu Gly Val Gly Val Ser Ser
                260                 265                 270

Ser Arg Asn Arg Ala Glu Glu Ala Ala Glu Gln Ala Thr Leu Ala Pro
        275                 280                 285

Leu Ile Gly Leu Ser Ile Gln Ser Ala Thr Gly Val Val Tyr Asn Ile
    290                 295                 300

Thr Gly Gly Lys Asp Ile Thr Leu Gln Glu Val Asn Lys Val Ser Gln
305                 310                 315                 320

Val Val Thr Ser Leu Ala Asp Pro Ser Ala Asn Ile Ile Phe Gly Ala
                325                 330                 335

Val Val Asp Glu Arg Tyr Asn Gly Glu Ile Gln Val Thr Leu Ile Ala
                340                 345                 350

Thr Gly Phe Ala Gln Ser Phe Gln Asn Ser Leu Leu Thr Asp Pro Arg
        355                 360                 365

Gly Ala Lys Leu Val Asp Lys Ser Lys Gly Thr Thr Glu Arg Thr Val
    370                 375                 380

Ser Pro Asp Thr Leu Arg Ser Ser Glu Ser Pro Ser Thr Lys Pro Arg
385                 390                 395                 400

Pro Ala Ala Arg Arg Leu Phe Phe
                405

<210> SEQ ID NO 32
<211> LENGTH: 413
<212> TYPE: PRT
<213> ORGANISM: Nicotiana tabacum
```

```
<400> SEQUENCE: 32

Met Ala Thr Met Leu Gly Leu Ser Ser Asn Thr Gly Ile Asp Ile Leu
 1               5                  10                  15

Ser Ser Ser Ser Asn Ser Leu Ser Phe Tyr His Ser Thr Arg Phe Thr
             20                  25                  30

Gln Cys Phe Ser Pro Lys Ser Leu Cys Lys Arg Gln Arg Arg Arg Phe
         35                  40                  45

Ser Ile Cys Ser Ser Leu Ser Ser Ala Lys Ile Lys Val Val Gly Val
     50                  55                  60

Gly Gly Gly Gly Asn Asn Ala Val Asn Arg Met Ile Gly Ser Gly Leu
 65                  70                  75                  80

Gln Gly Val Asp Phe Tyr Ala Val Asn Thr Asp Ala Gln Ala Leu Leu
                 85                  90                  95

Gln Ser Thr Val Glu Asn Pro Ile Gln Ile Gly Glu Leu Leu Thr Arg
            100                 105                 110

Gly Leu Gly Thr Gly Asn Pro Leu Leu Gly Glu Gln Ala Ala Glu
            115                 120                 125

Glu Ser Lys Glu His Ile Ala Asn Ala Leu Lys Gly Ser Asp Met Val
130                 135                 140

Phe Ile Thr Ala Gly Met Gly Gly Thr Gly Ser Gly Ala Ala Pro
145                 150                 155                 160

Val Val Ala Gln Ile Ala Lys Glu Ala Gly Tyr Leu Thr Val Gly Val
                165                 170                 175

Val Thr Tyr Pro Phe Ser Phe Glu Gly Arg Lys Arg Ser Leu Gln Ala
            180                 185                 190

Leu Glu Ala Ile Glu Lys Leu Gln Lys Asn Val Asp Thr Leu Ile Val
            195                 200                 205

Ile Pro Asn Asp Arg Leu Leu Asp Ile Ala Asp Glu Gln Thr Pro Leu
210                 215                 220

Gln Asn Ala Phe Leu Leu Ala Asp Asp Val Leu Cys Gln Gly Val Gln
225                 230                 235                 240

Gly Ile Ser Asp Ile Ile Thr Ile Pro Gly Leu Val Asn Val Asp Phe
                245                 250                 255

Ala Asp Val Lys Ala Ile Met Lys Asp Ser Gly Thr Ala Met Leu Gly
            260                 265                 270

Val Gly Val Ser Ser Ser Arg Asn Arg Ala Glu Glu Ala Ala Glu Gln
            275                 280                 285

Ala Thr Leu Ala Pro Leu Ile Gly Ser Ser Ile Gln Ser Ala Thr Gly
290                 295                 300

Asp Val Tyr Asn Ile Thr Gly Gly Lys Asp Ile Thr Leu Gln Glu Val
305                 310                 315                 320

Asn Lys Val Ser Gln Val Val Thr Ser Leu Ala Asp Pro Ser Ala Asn
                325                 330                 335

Ile Ile Phe Gly Ala Val Val Asp Glu Arg Tyr Asn Gly Glu Ile Gln
            340                 345                 350

Val Thr Leu Ile Ala Thr Gly Phe Ala Gln Ser Phe Gln Asn Ser Leu
            355                 360                 365

Leu Thr Asp Pro Arg Gly Ala Lys Leu Val Asp Lys Ser Lys Gly Thr
370                 375                 380
```

-continued

```
Thr Glu Arg Thr Val Ser Pro Asp Thr Leu Arg Ser Ser Glu Ser Pro
385                 390                 395                 400

Ser Thr Lys Pro Arg Pro Ala Thr Arg Arg Leu Phe Phe
                405                 410
```

OOMYCETE FTSZ-MT AS A TARGET FOR OOMYCETE-SPECIFIC ANTIMICROBIALS

FIELD OF THE INVENTION

The invention relates to the field of antimicrobials, and more specifically to isolated polynucleotides encoding FtsZ proteins as targets for screening methods to obtain antimicrobials specific for oomycetes and α-proteobacteria.

BACKGROUND OF THE INVENTION

Oomycetes

The Oomycota are filamentous protists which gain their nutrition by absorbing food from surrounding water or soil, or by invading the body of another organism to feed on fluids there. There are more than 500 species in the Oomycota, including the so-called water molds and downy mildews. As such, oomycetes play an important role in the decomposition and recycling of decaying matter. Parasitic species have had a impact on human activities by destroying crops or fish.

"Oomycota" means "egg fungi," which refers to the large round oogonia, or structures containing the female gametes. Oomycetes are oogamous, producing large non-motile gametes called eggs, and smaller gametes called sperm. The Oomycota have a very sparse fossil record. A possible oomycete has been described from Cretaceous amber.

The Oomycota were once classified as fungi, because of their filamentous growth, and because they feed on decaying matter as do fungi. The cell wall of oomycetes is not, however, composed of chitin as in the fungi, but instead is made up of a mix of cellulosic compounds and glycan. Another distinguishing feature is that the nuclei within the filaments are diploid, with two sets of genetic information, not haploid as in the fungi.

The ultrastructure, biochemistry, and molecular sequences of these organisms indicate that they belong with the Chromista. The free-swimming spores which are produced bear two dissimilar flagella, one with mastigonemes, a feature that is common in the chromists, as is the presence of the chemical mycolaminarin, an energy storage molecule similar to those found in kelps and diatoms. Thus, oomycetes are classified as belonging to the taxonomic minority known as heterotrophic chromists.

Some oomycetes, also called molds or water molds, are parasites on other organisms. Water molds may grow on the scales or eggs of fish, or on the skins of amphibians. The water mold *Saprolegnia* causes lesions on fish which cause problems when the water is stagnant as is often the case in aquaria or fish farms, or at high population densities such as when salmon swim upstream to spawn. *Saprolegnia* can spread rapidly, damaging a large surface area. These infections can be difficult to treat. Other species of *Saprolegnia* are parasitic on aquatic invertebrates such as rotifers, nematodes, and arthropods, and on diatoms.

Their greatest impact on humans, however, comes from the many species of oomycete which are parasites on flowering plants. These include root rotting oomycetes, seedling dampening mold, blister rusts, white rusts Albugo, and the downy mildews that affect grapes, lettuce, corn, cabbage, and many other crop plants. Two of these disease-causing oomycetes have had a major impact on world history.

The first of these is *Phytophthora infestans*, the organism which causes late blight of potato. The potato is native to South America, but after it was introduced to Europe in the late 16$^{th}$ century, it quickly became an important food crop. Late blight did not follow its host plant across the Atlantic until much later. The disease organism grows into the stem and leaf tissues, causing death, and may also infest the tubers. The disease spreads rapidly under cool and damp conditions, which are common in western Europe. In one famous case, in just one week during the summer of 1846, this disease wiped out almost the entire potato crop of Ireland, where potatoes were the primary food of the poor. This *Phytophthora* blight caused the deaths of nearly a million inhabitants of Ireland, and precipitated the emigration of an additional 1.5 million to other countries. Other species of *Phytophthora* destroy eucalyptus, avocado, pineapples, and other tropical crop plants. While chemicals have been developed to combat oomycete infections, the emergence of chemical-resistant strains combined with banning of effective chemicals has combined to create a *P. infestans* epidemic which is now a serious problem.

The other oomycete which has severely impacted recent history is *Plasmopara viticola*, the downy mildew of grapes. It is a native of North America, but in the late 1870s was accidentally introduced to Europe. At the time, the French wine industry was concerned over a massive aphid infestation, and so brought resistant vine strains over from America to breed them into their own grapes. When these American stocks arrived, the American vines also brought the downy mildew, which almost wiped out the entire French wine industry. The industry was saved by the serendipitous discovery of Bordeaux mixture, a mixture of lime and copper sulfate, which brought the disease under control when applied to the leaves of the plants. This discovery is also important for being the first known fungicide, and in fact the first chemical used to control a plant disease. However, Bordeaux mixture is hazardous to many other organisms.

A current problem is Sudden Oak Death Syndrome which is caused by a previously unknown species of *Phytophthora*. First observed in 1995, within 5 years the infestation by this plant pest has spread 350 miles along the California coast infecting tan oaks, coast live oaks and black oaks. In some areas, as many as 80% of the trees are infected. A state of emergency has been declared in Marin County, one of the hardest-hit areas. Effective, environmentally-safe means to combat this *Phytophthora* species have not been determined.

This disease not only impacts oaks, but also the thousands of animal species that rely on leaves and acorns from these trees, as well as increasing the fire risk posed by the rapid accumulation of dead trees.

FtsZ proteins

FtsZ (named after filamenting temperature sensitive strain Z) is a 40 kDa protein ubiquitous in Eubacteria and Archaea. The bacterial cell division protein FtsZ is a key component of the bacterial cell division machinery. Fusion constructs of FtsZ with green-fluorescent protein have shown that, at the onset of division, FtsZ forms a filamentous ring at the site of cell division, and disassembles after septation is complete. FtsZ can self-assemble into rafts of long filaments having curving edges, as well as into sheets and rings. A cytoskeletal role for FtsZ has been postulated based on its ability to undergo GTP-dependent polymerization in vitro and its similarity to tubulin. Bacterial FtsZ shares limited sequence identity with tubulin, and the axial repeat of these filaments is around 40 Å, the same as that of tubulin monomers in a protofilament. The structure of FtsZ has been solved by X-ray crystallography using crystals obtained from the FtsZ1 protein from the hyperthermophilic methanogen *Methanococcus jannaschii*. The model, refined to 2.8 Å, includes a molecule of GDP.

Until recently, the only known eukaryotic FtsZs were chloroplastic FtsZs (FtsZ-cp) in plants. In higher plants, the FtsZ protein is involved in plastid division, but there is little information on its involvement in the plastid-dividing apparatus. Comparison of several prokaryotic and eukaryotic FtsZ proteins shows that there are six highly conserved domains in the core region of FtsZ. Phylogenetic analysis indicates that *Cyanidium caldarium* RK-1 and other eukaryotic FtsZ genes are the descendants of cyanobacterial FtsZ genes, supporting the current agreement that FtsZ is involved in plastid division. Expression studies of the gene encoding FtsZ (the FtsZ gene) in *C. caldaium* indicated that the FtsZ gene is transcribed just before plastid division. Eukaryotic FtsZ isolated from *Arabidopsis thaliana* contains a glycine-rich tubulin signature motif which is conserved among FtsZ proteins and tubulins, and which is important for GTP binding, which further supports the suggestion that eukaryotic FtsZ proteins may have a cytoskeletal role analogous to that of tubulin. (U.S. Pat. No. 5,981,836).

In major groups of eukaryotes, such as animals, plants and true fungi, mitochondrial division is mediated by a non-FtsZ mechanism. There are no FtsZ genes in yeast or nematode where the respective genomes have been completely sequenced. The recent discovery of the mitochondrial form of FtsZ (FtsZ-mt) in a chromophyte alga (Beech et al. (2000) *Science* 287: 1276–1279) strongly suggests that in primitive eukaryotes, unlike major groups of eukaryotes, FtsZ-mt is required for mitochondrial division.

SUMMARY OF THE INVENTION

The invention is directed to methods for identifying and using compounds having antimicrobial activity, methods for identifying and using compounds having anti-FtsZ activity, methods for suppressing microbial growth, methods of crop improvement, methods of producing an FtsZ-mt protein, methods of using a virtual screen to identify potential inhibitors of FtsZ-mt proteins which do not inhibit FtsZ-cp proteins, and methods of treating fish infected with an oomycete pathogen. The invention further provides compounds identified by the methods of the present invention and isolated DNA molecules encoding mitochondrial FtsZ proteins, preferably from oomycetes.

Embodiments of the present invention provide a method for identifying compounds having antimicrobial activity by combining at least a portion of a polypeptide or protein which includes an amino acid sequence encoding an oomycete FtsZ-mt protein with a compound to be tested for the ability to bind to an FtsZ-mt protein or to the polypeptide, under conditions conducive to binding, selecting a compound thus identified as capable of binding to the FtsZ-mt protein or the polypeptide, applying the selected compound to a microbe to test for antimicrobial activity, and then selecting compounds having antimicrobial activity. These methods may be practiced using FtsZ-mt protein encoded by an isolated DNA molecule having a nucleotide sequence substantially similar to the sequence of SEQ ID NO: 1, or SEQ ID NO: 3, or SEQ ID NO: 5, or SEQ ID NO: 9. These methods may be practiced using FtsZ-mt protein encoded by an isolated DNA molecule which encodes the amino acid sequence of SEQ ID NO: 2, or SEQ ID NO: 4, or SEQ ID NO: 10. In one embodiment, the microbe is an oomycete such as *Phytophthora infestans*. A further aspect of the present invention is a compound identified by practicing methods of the present invention for identifying compounds having antimicrobial activity.

Embodiments of the present invention provide a method for identifying an inhibitor of FtsZ-mt activity having antimicrobial activity by combining an FtsZ-mt protein or a portion thereof, and a compound to be tested for the ability to inhibit the activity of the FtsZ-mt protein or an active region thereof, under conditions conducive to such inhibition, selecting a compound thus identified as capable of inhibiting said FtsZ-mt activity, applying the compound identified as capable of inhibiting said FtsZ-mt activity to a microbe to test for antimicrobial activity, and selecting compounds having antimicrobial activity. Methods of the present invention for identifying an inhibitor of FtsZ-mt activity having antimicrobial activity may be practiced using at least a portion of an FtsZ-mt protein or a substantially similar polypeptide, encoded by an isolated DNA molecule having a nucleotide sequence substantially similar to the sequence of SEQ ID NO: 1, or SEQ ID NO: 3, or SEQ ID NO: 5, or SEQ ID NO: 9. Methods of the present invention for identifying an inhibitor of FtsZ-mt activity having antimicrobial activity may be practiced using FtsZ-mt protein or a portion thereof, or a substantially similar polypeptide, encoded by an isolated DNA molecule which encodes an amino acid sequence substantially similar or identical to at least a portion of SEQ ID NO: 2, or SEQ ID NO: 4, or SEQ ID NO: 10. In one embodiment of the method for identifying an inhibitor of FtsZ-mt activity having antimicrobial activity, the microbe is an oomycete such as *Phytophthora infestans*. A further aspect of the present invention is a compound identified by the method of the present invention for identifying an inhibitor of FtsZ-mt activity having antimicrobial activity.

Embodiments of the present invention further provide methods for suppressing oomycete growth by applying to an oomycete a compound that inhibits the activity of an oomycete FtsZ-mt protein including an amino acid sequence encoded by a nucleotide sequence substantially similar to a polynucleotide selected from, for example, SEQ ID NO: 1, SEQ ID NO: 3, SEQ ID NO: 5 or SEQ ID NO: 9, in an amount sufficient to suppress growth of the oomycete.

Embodiments of the present invention provide a method of crop improvement by applying to a plant, plant part, plant seed, or surrounding soil a compound having antimicrobial activity identified by methods of the present invention for identifying compounds having antimicrobial activity, where the compound is applied in an amount that inhibits the growth of microbes of at least one microbe taxon without significantly suppressing the growth of the plant or plant seed. Another object is a method of crop improvement by applying to a plant, plant part, plant seed, or surrounding soil a compound having antimicrobial activity identified by methods of the present invention for identifying an inhibitor of FtsZ-mt activity having antimicrobial activity, where the compound is applied in an amount that inhibits the growth of microbes of at least one microbe taxon without significantly suppressing the growth of the plant or seed. Further aspects of methods of crop improvement in accordance with the present invention include microbes of various taxa, such as, for example, Lagena, Peronophythora, Trachysphaera, Pythium, Phytophthora, Albugo, Peronospora, Plasmopora, Pseudoperonospora, Bremia, Bremiella, Basidiophora and the like. Yet further aspects of methods of crop improvement in accordance with the present invention include treatment of any crop plant, such as, for example, potato, tomato, tobacco, oaks, coffee berry (Rhamnus sp.), squash, cotton, sorghum, peas, onion, melon, cucumber, peas, beets, watermelon, peppers, Port Orford Cedar, taro, apple, Brassica species, sweet potato (Ipomea), spinach, beans, grapevine, sunflower, hops, lettuce, violets, asters, soybeans, and cereals including maize, rice, barley, wheat, rye, and the like.

Embodiments of the present invention provide an isolated DNA molecule which encodes a mitochondrial FtsZ protein obtained from an oomycete. In one embodiment, the isolated DNA molecule is obtained from *Phytophthora infestans*. In other embodiments, the isolated DNA molecule obtained from an oomcyete has the sequence of SEQ ID NO: 1, or SEQ ID NO: 3, or SEQ ID NO: 5, or SEQ ID NO: 9.

Embodiments of the present invention provide an isolated DNA molecule capable of hybridizing to a polynucleotide having a sequence selected from, for example, SEQ ID NO: 1, SEQ ID NO: 3, SEQ ID NO: 5, or SEQ ID NO: 9, wherein the hybridization takes place in 7% sodium dodecyl sulfate, 0.5 M NaPO$_4$, 1 mM EDTA at 50° C. for a pre-determined time followed by washing in 2× SSC, 0.1% sodium dodecyl sulfate at 50° C. Further aspects of the invention provide an isolated DNA molecule having at least 65% sequence identity with the polynucleotide sequence of, for example, SEQ ID NO: 1, or SEQ ID NO:3, or SEQ ID NO: 5, or SEQ ID NO: 9.

Other aspects of the invention provide an isolated DNA molecule which encodes a peptide having an amino acid sequence selected from, for example, SEQ ID NO: 2, SEQ ID NO: 4, or SEQ ID NO: 10. Further aspects of the invention provide an isolated peptide having a sequence such as SEQ ID NO: 2, SEQ ID NO: 4, or SEQ ID NO: 10.

Embodiments of the present invention provide methods of producing at least one FtsZ-mt protein by transforming a suitable host cell with a construct including an isolated polynucleotide encoding an oomycete FtsZ-mt protein, culturing the host cells under conditions in which the cells express said isolated polynucleotide, and recovering the oomycete FtsZ-mt protein. Embodiments of these methods include producing FtsZ-mt protein by transforming a suitable host cell with an expression vector including an isolated polynucleotide encoding an oomycete FtsZ-mt protein. In various embodiments, the isolated polynucleotide has a sequence selected from, for example, SEQ ID NO: 1, SEQ ID NO:3, SEQ ID NO: 5, or SEQ ID NO: 9.

Embodiments of the present invention further provide methods of using a virtual screen to identify potential inhibitors of FtsZ-mt proteins which do not inhibit FtsZ-cp proteins, by predicting the three dimensional structure of an FtsZ-mt protein, predicting the three-dimensional structure of an FtsZ-cp protein, and using a computer model to identify molecules which bind to FtsZ-mt proteins but not to FtsZ-cp proteins as potential inhibitors of FtsZ-mt proteins. In some embodiments, the FtsZ-mt protein is an oomycete FtsZ-mt protein. Preferably, the oomycete belongs to the genus Phytophthora. Even more preferably, the oomycete is *Phythophthora infestans*. Preferably, the FtsZ-mt protein has at least about 20 amino acids of the sequence of any of SEQ ID NO: 2, SEQ ID NO: 4, or SEQ ID NO: 10. Also preferably, the FtsZ-mt protein has a sequence selected of any of SEQ ID NO: 2, SEQ ID NO: 4, or SEQ ID NO: 10. Another aspect is an inhibitor of FtsZ-mt proteins identified by the method of using a virtual screen to identify potential inhibitors of FtsZ-mt proteins which do not inhibit FtsZ-cp proteins in accordance with the present invention. In another embodiment, tobacco FtsZ-cp protein can be used. In yet another embodiment, Arabidopsis FtsZ-cp protein can be used.

Embodiments of the present invention provide an antimicrobial which inhibits growth of an oomycete, wherein the antimicrobial affects the FtsZ-mt protein of the oomycete. Embodiments of the present invention provide methods of treating a fish infected with an oomycete pathogen by application of a compound identified by methods of the present invention for identifying compounds having antimicrobial activity, which methods can include the steps of combining a polypeptide having substantial similarity to at least a portion of a an oomycete FtsZ-mt protein, with a compound to be tested for the ability to bind to an FtsZ-mt protein under conditions conducive to binding, selecting a compound thus identified as capable of binding to said FtsZ-mt protein, applying the selected compound to a microbe to test for antimicrobial activity, and then selecting compounds having antimicrobial activity. Preferably, the oomycete pathogen belongs to the genus *Saprolegnia*.

Embodiments of the present invention provide methods of treating a fish infected with an oomycete pathogen by application of a compound identified by methods of the present invention for identifying an inhibitor of FtsZ-mt activity having antimicrobial activity, by combining a FtsZ-mt protein and a compound to be tested for the ability to inhibit the activity of the FtsZ-mt protein, under conditions conducive to such inhibition, selecting a compound thus identified as capable of inhibiting said FtsZ-mt activity, applying the compound identified as capable of inhibiting said FtsZ-mt activity to a microbe to test for antimicrobial activity, and selecting compounds having antimicrobial activity. Preferably, the oomycete pathogen is of the genus *Saprolegnia*.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description of the preferred embodiments which follow.

BRIEF DESCRIPTION OF THE DRAWINGS

These and other features of this invention will now be described with reference to the drawings of preferred embodiments which are intended to illustrate and not to limit the invention.

FIG. 1, 1A–1D. Complete cDNA sequence of FtsZ-mt2 from *Phytophthora infestans*, showing nucleotide sequence (SEQ ID NO:9) and predicted amino acid sequence (SEQ IDN O: 10).

FIG. 2, 2A–2D. Alignment of FtsZ sequences from *Agrobacterium tumefaciens* (SEQ ID NO: 11), *Sinorhizobium meliloti* (SEQ ID NO: 12), *Bartonella clarridgeiae* (SEQ ID NO: 13), *Rickettsia prowazekii* (SEQ ID NO: 14), *Caulobacter crescentus* (SEQ ID NO: 15), *Cyanidioschyzon merolae*-mt (SEQ ID NO: 16), *Phytophthora infestans*-mt2 (SEQ ID NO: 4), *Mallomonas splendens*-mt (SEQ ID NO: 17), *Phytophthora infestans*-mt1 (SEQ ID NO: 2), *Gentiana lutea*-cp (SEQ ID NO: 18), *Nicotiana tabacum*-cp2-1 (SEQ ID NO: 19), *Arabidopsis thaliana*-cp2 (SEQ ID NO: 20), *Physcomitrella patens*-cp1 (SEQ ID NO: 21), *Physcomitrella patens*-cp2 (SEQ ID NO: 22), *Guillardia theta*-cp (SEQ ID NO: 23), *Mallomonas splendens*-cp (SEQ ID NO: 24), Anabaena (SEQ ID NO: 25), Synechocystis (SEQ ID NO: 26), *Arabidopsis thaliana*-cp1 (SEQ ID NO: 27), *Pisum sativum*-cp (SEQ ID NO: 28), *Nicotiana tabacum*-cp1-3

(SEQ ID NO: 29), *Nicotiana tabacum*-cp1 (SEQ ID NO: 30), *Nicotiana tabacum*-cp1-1 (SEQ ID NO: 31), and *Nicotiana tabacum*-cp2 (SEQ ID NO: 32).

Figure 1:
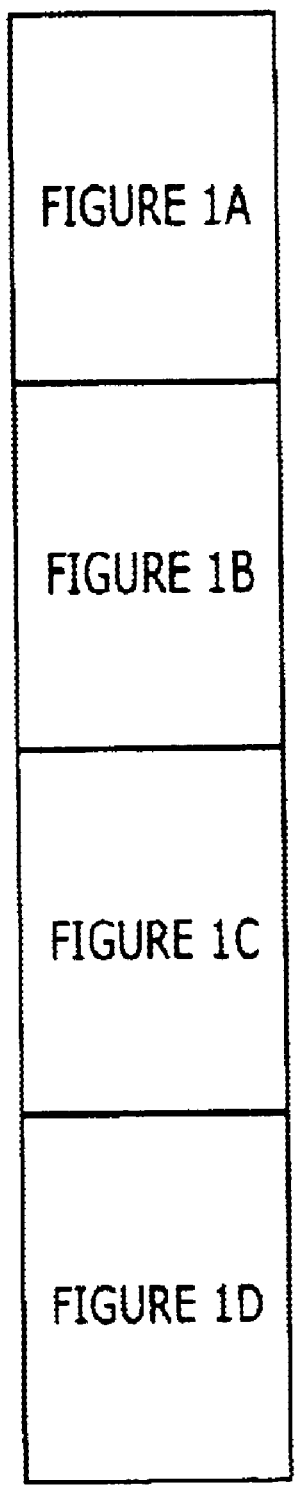
Figure 2:
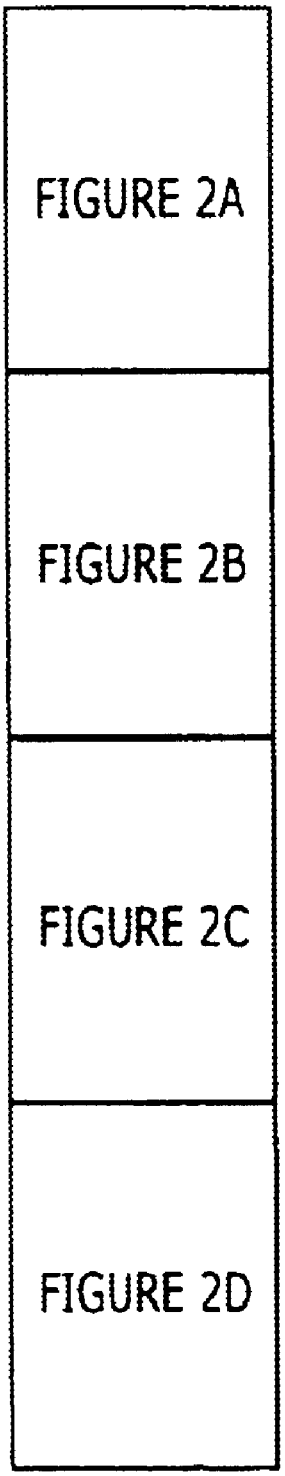
Figure 3:
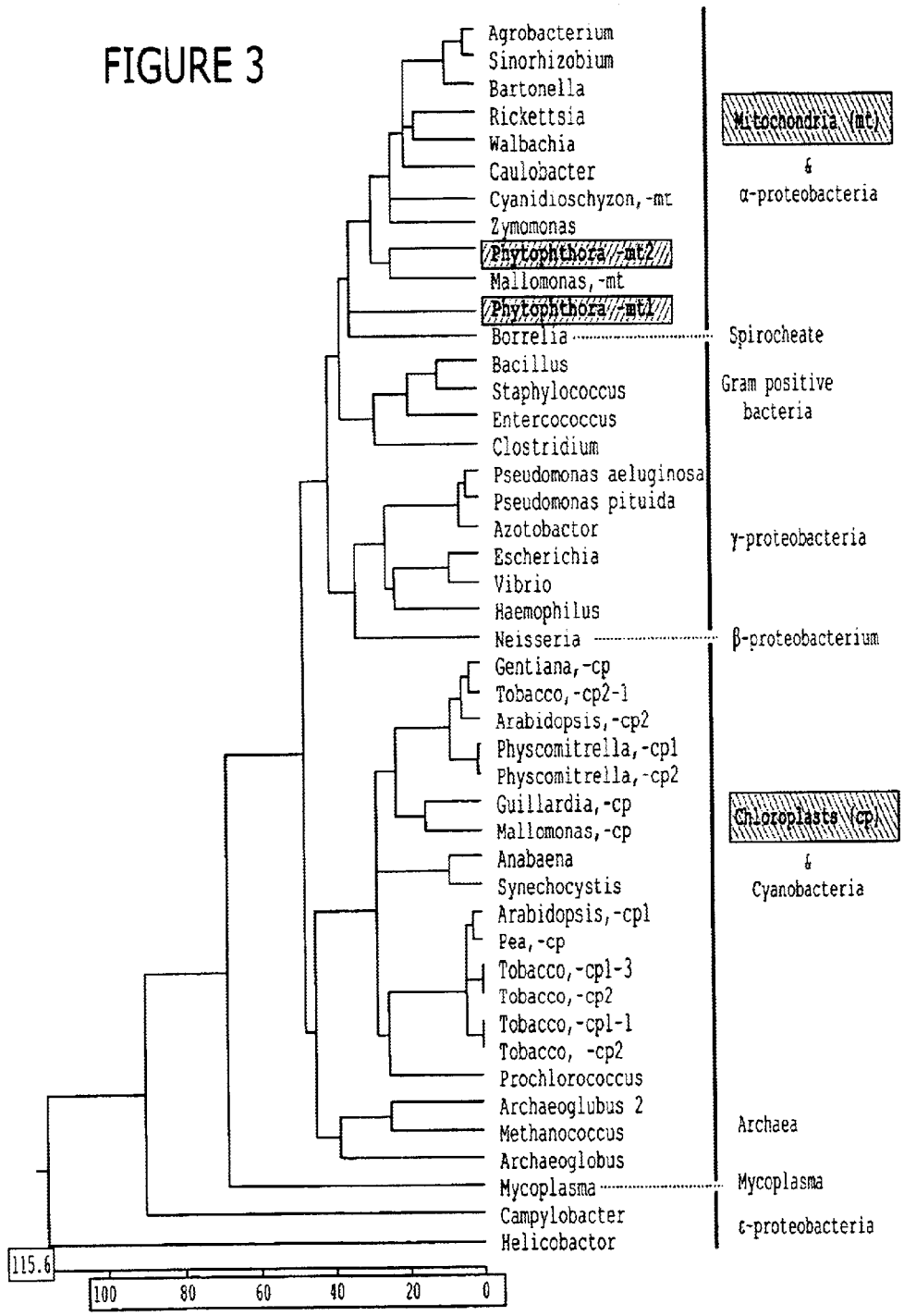

FIG. 3. Phylogenetic tree of FtsZ proteins. The phylogenetic relationship among chloroplastic, cynaobacterial, mitochondrial and proteobacterial FtsZs is shown based upon comparison of amino acid sequences. The phylogenetic tree also includes Archaea and bacteria other than Proteobacteria. Both FIG. 2 and FIG. 3 were constructed using a clustal method (Higgins and Sharp (1989) *Comput Appl Biosci* 5: 151–153).

DETAILED DESCRIPTION OF THE PREFERRED EMBODIMENT

The presently claimed invention is drawn to the use of FtsZ-mt as a target for antimicrobials. FtsZ-mt is an ideal target as it appears to be unique to primitive eukaryotes such as oomycetes and has no counterpart in true fungi and higher eukaryotes.

Preferred embodiments of the present invention will be explained below. However, the present invention includes various embodiments and is not limited to the preferred embodiments.

The invention relates to genes isolated from *Phytophthora infestans* that code for an essential protein having a proposed role in mitochondrial division (Beech et al. (2000) *Science* 287:1276–1279). The invention also includes the methods of using these proteins as antimicrobial targets, based on the essentiality of the gene for normal growth and development. The invention is also useful as a screening assay to identify inhibitors that are potential antimicrobials.

The use of antimicrobials to control the growth of undesirable microbes that cause disease has become almost a universal practice. Antimicrobials against plant disease agents may be applied to a plant, a plant part, and/or the soil surrounding a plant. Antimicrobials against animal disease agents may be applied directly to an animal, or may be applied to the environment, for example in solution to treat fish. However, development of resistance of microbes to antimicrobials is a major problem. Extensive use of the same antimicrobial kills susceptible individuals, while resistant individuals survive, which permits resistant individuals to reproduce and pass on their capacity for resistance to their progeny. The progeny take over niches formerly occupied by susceptible individuals. Eventually, the whole population may become resistant, resulting in a failure of pest management practices.

As antimicrobials are lost to the development of resistance in target populations, the production of effective new antimicrobials becomes increasingly important. It is important that these chemicals also be harmless to higher eukaryotes. Novel antimicrobials can now be discovered using high-throughput screens that implement recombinant DNA technology. Metabolic enzymes found to be essential to microbial growth and development can be recombinantly produced through standard molecular biological techniques and utilized as antimicrobial targets in screens for novel inhibitors of protein functions. Novel inhibitors discovered through such screens may then be used as antimicrobials to control undesirable microbial growth.

Virtual screens can also be used based upon the predicted three-dimensional structure of the protein of interest. Chemicals that bind to the microbial protein, but not to the corresponding higher plant protein, are good candidates for antimicrobials which can then be tested for efficacy in a particular organism. Candidates for antimicrobials may be tested for efficacy in a cultivation system such as a crop system or an aquaculture system, or in a less-managed system such as of oak trees in a mixed stand.

Persistent and ongoing problems with microbial proliferation remain, causing various plant diseases including root rot, fruit rot, mealy rot, damping off, cortical rot, foliar blight, leaf blight, rhizome rot, root disease, white rust, and downy mildew (See Table 1). Furthermore, as human populations continue to grow, there will be increasing food shortages as food is lost to pre-harvest and post-harvest disease. Therefore, there exists a long-felt and yet-unfulfilled need to find new, effective, and economic antimicrobials.

Definitions:

For clarity, certain terms used in the specification are generally defined and presented as follows:

"Chimeric" as used herein, is generally used to indicate that a nucleic acid sequence, such as a vector or a gene, is comprised of more than one nucleic acid sequence of distinct origin, where the nucleic acid sequences are fused by recombinant techniques resulting in a nucleic acid sequence which does not occur naturally.

"Expression" as used herein, generally refers to the transcription and/or translation of an endogenous gene, a transgene, or other construct capable of being transcribed and/or translated. In the case of antisense constructs, for example, expression may refer to the transcription of the antisense RNA.

"Gene" as used herein, generally refers to a coding sequence, optionally associated with regulatory sequences, wherein the coding sequence is normally transcribed into RNA such as, for example, mRNA, rRNA, tRNA, snRNA, sense RNA or antisense RNA. Examples of regulatory sequences are promoter sequences, 5' and 3' untranslated sequences, and the like. Further elements that may be present are, for example, introns.

"Antimicrobial" as used herein, generally refers to a substance, compound, or composition, whether chemical, biological, or otherwise, that is used to kill or suppress the growth or reproduction of microbes such as bacteria, molds, mildews, fungi, and oomycetes.

"Heterologous Sequence" as used herein, generally refers to a nucleic acid or polypeptide sequence not naturally associated with a host cell into which it is introduced, including non-naturally-occurring multiple copies of a naturally occurring nucleic acid or polypeptide sequence, where the term may also refer a nucleic acid or polypeptide sequence not naturally associated with the other nucleic acid or polypeptide sequences in a construct.

"Inhibitor" as used herein, generally refers to a substance, compound, or composition, whether chemical, biological, or otherwise, that inactivates the activity of an active or functional molecule or complex, such as, for example, a biosynthetic enzyme, receptor, signal transduction protein, structural gene product, or transport protein. Preferred inhibitors may disrupt activities that are essential to the growth, reproduction, or survival of a plant.

"Isolated" as used in the context of the present invention, such as an isolated DNA or protein molecule, generally refers to a molecule, substance, compound, or composition that, by the hand of man, exists apart from its native environment and is therefore not a product of nature. For example, an isolated DNA molecule or protein may exist in a purified form or may exist in a non-native environment such as, for example, a transgenic host cell.

"Mature protein" as used herein, generally refers to a protein that is subject to post-translational modifications, and that has undergone one or more such modifications. For example, a protein that is normally targeted to a cellular organelle, such as a chloroplast, from which the transit peptide has been removed, is a mature protein.

"Operably linked to" or "associated with" as used herein, refer generally to two or more nucleic acid sequences that are functionally juxtaposed or adjacent. For example, a regulatory DNA sequence is said to be "operably linked to" or "associated with" a DNA sequence that codes for an RNA or a protein, if the two sequences are situated such that the regulatory DNA sequence affects expression of the coding DNA sequence.

"Plant" as used herein, refers generally to any plant or plant part such as, for example, leaves, stems, roots, flowers or flower parts, fruits, pollen, pollen tubes, ovules, embryo sacs, egg cells, zygotes, embryos, seeds, cuttings, and particularly to seed plants.

"Plant cell" as used herein, refers generally to a structural and physiological unit of a plant. The plant cell may be in form of an isolated single cell or a cultured cell which may or may not contain a cell wall, or as a part of higher organized unit such as, for example, a plant tissue, or a plant organ.

"Plant material" as used herein, refers generally to whole plants or plant parts such as leaves, stems, roots, flowers or flower parts, fruits, pollen, pollen tubes, ovules, embryo sacs, egg cells, zygotes, embryos, seeds, cuttings, cell or tissue cultures, or any other part or product of a plant, such as rubber, agar or wood products.

"Region" or "Portion" of a nucleic acid or polypeptide sequence, as used herein, refers generally to a substantially contiguous segment of adjacent nucleic acids or amino acids in a nucleic acid or polypeptide sequence, such that the segment is of sufficient length to encode or include a functional or active part or domain of a polypeptide, or a plurality of such functional or active domains, whether or not such domains are separated by other sequences. As an alternative, a region or portion can encode or include a part of a polypeptide that is not functional or active from the perspective of a native protein, but which carries at least one other kind of useful feature, such as, for example, an epitope that is recognized by an antibody, a structure that is recognized by an inhibitor, and the like.

"Selectable marker" as used herein, refers generally to a sequence whose expression permits selection of a cell expressing the marker, or differentiation between a cell expressing or containing the marker and a cell that does not express or contain the marker. A preferred selectable marker generally confers a selective advantage on the cell in which it is expressed or which contains it. The selective advantage possessed by transformed cells having the selectable marker may be due to their ability to grow in the presence of a negative selective agent, such as an antibiotic or an antimicrobial, compared to the growth of non-transformed cells. The selective advantage possessed by the transformed cells, compared to non-transformed cells, may also be due to their enhanced or novel capacity to utilize an added compound as a nutrient, growth factor or energy source. "Selectable marker gene" can also refer to a gene or a combination of genes whose expression in a cell gives the cell both a negative and a positive selective advantage.

"Sequence Identity" refers generally to a quantitative measure of the degree to which two or more sequences are identical. The percentage of sequence identity is typically determined using computer programs that are based on dynamic programming algorithms. Computer programs that are preferred within the scope of the present invention include the BLAST (Basic Local Alignment Search Tool) search programs designed to explore all of the available sequence databases regardless of whether the query is protein or DNA. Version BLAST 2.0 (Gapped BLAST) of this search tool has been made publicly available on the Internet (currently available at http://www.ncbi.nim.nih.gov/BLAST/). It uses an heuristic algorithm which seeks local as opposed to global alignments and is therefore able to detect relationships among sequences which share only isolated regions. The scores assigned in a BLAST search have a well-defined statistical significance.

The term "substantially similar" as used herein, generally refers to the correspondence of a given nucleotide or polypeptide sequence to a reference sequence. A nucleic acid sequence that is substantially similar to a reference sequence may encode a polypeptide having substantially the same structure and function as the polypeptide encoded by the reference nucleotide sequence, preferably, for example, where the only changes in amino acids do not affect the polypeptide function. Desirably the substantially similar nucleotide sequence encodes the polypeptide encoded by the reference nucleotide sequence. The term "substantially similar" is specifically intended to include nucleotide sequences wherein the sequence has been modified to optimize expression in particular cells. The percentage of identity between the substantially similar nucleotide sequence and the reference nucleotide sequence desirably is at least about 65%, more desirably at least about 75%, preferably at least about 85%, more preferably at least about 90%, still more preferably at least about 95%, yet still more preferably at least about 99%.

A nucleotide sequence "substantially similar" to a reference nucleotide sequence hybridizes to the reference nucleotide sequence in 7% sodium dodecyl sulfate (SDS), 0.5 M $NaPO_4$, 1 mM EDTA at 50° C. with washing in 2× SSC, 0.1% SDS at 50° C.; more desirably hybridization is in 7% sodium dodecyl sulfate (SDS), 0.5 M $NaPO_4$, 1 mM EDTA at 50° C. with washing in 1× SSC, 0.1% SDS at 50° C.; more desirably still, hybridization is in 7% sodium dodecyl sulfate (SDS), 0.5 M $NaPO_4$, 1 mM EDTA at 50° C. with washing in 0.5× SSC, 0.1% SDS at 50° C.; more preferably, hybridization is in 7% sodium dodecyl sulfate (SDS), 0.5 M $NaPO_4$, 1 mM EDTA at 50° C. with washing in 0.1× SSC, 0.1% SDS at 50° C.; more preferably, hybridization is in 7% sodium dodecyl sulfate (SDS), 0.5 M $NaPO_4$, 1 mM EDTA at 50° C. with washing in 0.1× SSC, 0.1% SDS at 65° C.

"Transformation" as used herein, generally refers to a process for introducing one or more heterologous nucleic acids into a cell, tissue, or plant. Transformed cells, tissues, or plants are understood to encompass not only the end product of a transformation process, but also transgenic progeny thereof.

"Transgenic" as used herein, refers to an organism containing a cell or cells that are transformed with, for example, a recombinant DNA molecule that preferably comprises a suitable promoter operatively linked to a DNA sequence of interest.

One object of the present invention is to provide essential genes in oomycetes for use in screening assays for inhibitory compounds having antimicrobial activity. Both FtsZ-mt and FtsZ-cp are nuclear-encoded. The protein products are transported into mitochondria and chloroplasts, respectively, by an N-terminal signal peptide. The FtsZ-mt gene is thought to be essential for mitochondrial division in oomycetes but has relatively low sequence identity to the corresponding chloroplast gene, FtsZ-cp (see FIG. 3). This indicates that some chemicals which inhibit the function of the FtsZ protein in oomycetes can have detrimental effects on oomycetes, but little or no effect on their plant hosts, and thus are potentially good antimicrobial candidates. FtsZ-mt also has no counterpart in higher eukaryotes such as mammals. Thus, selected chemicals with activity against FtsZ-mt will be harmless to major groups of higher eukaryotes, and toxicity to humans is expected to be non-existent. On the other hand, chemicals with activity against oomycetes would be expected to have activity against other microbes such as α-proteobacteria, due to conservation between genes encoding FtsZ in these organisms. The present invention therefore provides methods of using a purified protein encoded by the gene sequences described herein to identify inhibitors thereof, which can then be used as antimicrobials to suppress the growth of oomycetes such as Phytophthora, especially *Phytophthora infestans*, as well as α-proteobacteria such as *Agrobacterium* species, on plants.

Another object of the present invention is to provide methods of crop improvement using compounds identified as having antimicrobial activity. Antimicrobials to suppress the growth of oomycetes and α-proteobacteria may be applied to a plant, plant part, plant seed, or surrounding soil. Methods for applying compounds identified as having antimicrobial activity in accordance with methods of the present invention may include foliar application of these compounds in a suitable mixture, application to roots in the form of a root drench or root dip, introduction of these compounds directly into plants as in injection under bark or into xylem, introduction via grafting or cut surfaces, or application in fields where crops are grown. Aspects of the present invention include treatment of a wide variety of plants, particularly agronomically important crops including, but not limited to, potato, tomato, tobacco, oaks, coffee berry (Rhamnus sp.), squash, cotton, sorghum, peas, onion, melon, cucumber, peas, beets, watermelon, peppers, Port Orford Cedar, taro, apple, Brassica species, sweet potato (Ipomea), spinach, beans, grapevine, sunflower, hops, lettuce, violets, asters, soybeans, and cereals including maize, rice, barley, wheat, and rye, and the like.

In an alternate embodiment, the identified inhibitors may also be used against fish pathogens such as the oomycete *Saprolegnia*, as well as α-proteobacterial species which are disease agents for animals, including humans. An advantage of the present invention is that the newly discovered essential genes whose products serve as targets of a novel antimicrobial mode of action enables one skilled in the art to easily and rapidly identify novel antimicrobials. Another advantage of the present invention is that compounds identified as having antimicrobial activity in accordance with the methods of the present invention will have no effect on higher eukaryotes treated with the compounds.

In one embodiment, the present invention provides novel polynucleotides having the sequences of SEQ ID NOS: 1, 3, 5, or 9. The nucleotide sequence of SEQ ID NO: 1 encodes a protein designated as FtsZ-mt1 having the deduced amino acid sequence of SEQ ID NO: 2. Also provided is a second novel polynucleotide having the sequence shown in SEQ ID NO: 5 which encodes a second FtsZ-mt protein designated as FtsZ-mt2 (genomic) and having the amino acid sequence of SEQ ID NO: 4. FtsZ-mt2 (genomic) encodes a partial genomic sequence which has two introns as determined by the "GT-AG" rule and by amino acid sequence homology to other FtsZ proteins. The corresponding cDNA sequence for FtsZ-mt2 (genomic) is shown in SEQ ID NO: 3. The complete cDNA sequence corresponding to the partial genomic sequence FtsZ-mt2 is shown in SEQ ID NO: 9.

The present invention also encompasses nucleotide sequences substantially similar to those set forth in SEQ ID NOS: 1, 3, 5, or 9, wherein said nucleotide sequence is an oomycete, bacterial, or primitive eukaryote such as protistan, nucleotide sequence. Preferred is a nucleotide sequence substantially similar to those set forth in SEQ ID NOS: 1, 3, 5, or 9, wherein said nucleotide sequence is a *Phytophthora infestans* nucleotide sequence.

Further encompassed is a polynucleotide having a nucleotide sequence substantially similar to those set forth in SEQ ID NOS: 1, 3, 5, or 9, wherein the encoded protein has FtsZ activity. Particularly preferred is a nucleotide sequence substantially similar to those set forth in SEQ ID NOS: 1, 3, 5, or 9 wherein said encoded protein has FtsZ activity. Further encompassed is an amino acid sequence including an amino acid sequence encoded by a nucleotide sequence substantially similar to SEQ ID NOS: 1, 3, 5, or 9. Also encompassed is an amino acid sequence including an amino acid sequence encoded by SEQ ID NOS: 1, 3, 5, or 9.

Also encompassed are polynucleotides with substantial sequence identity to any of SEQ ID NOS: 1, 3, 5, or 9, more preferably at least about 65% sequence identity, yet more preferably at least about 70% sequence identity, yet more preferably at least about 75% sequence identity, yet more preferably at least about 80% sequence identity, yet more preferably at least about 85% sequence identity, yet more preferably at least about 90% sequence identity, yet more preferably at least about 95% sequence identity, yet more preferably at least about 99% sequence identity to any one of SEQ ID NOS: 1, 3, or 5.

The present invention also encompasses proteins whose amino acid sequences are substantially similar to the amino acid sequences set forth in SEQ ID NOS: 2, 4 or 10. Also encompassed is an amino acid sequence including an amino acid sequence substantially similar to any of SEQ ID NOS: 2, 4 or 10. Preferred is an amino acid sequence including an amino acid sequence which is SEQ ID NO: 2 or 4 or 10.

Encompassed herein is an amino acid sequence including an amino acid sequence encoded by a nucleotide sequence substantially similar to any of SEQ ID NOS: 1, 3, 5, or 9, wherein the protein has FtsZ activity. Further encompassed is an amino acid sequence including at least 20 consecutive amino acid residues of the amino acid sequence of any of SEQ ID NOS: 2, 4 or 10.

A further embodiment is a chimeric gene comprising a promoter operably linked to a nucleotide sequence substantially similar to any of SEQ ID NOS: 1, 3, 5, or 9. Further encompassed is a recombinant vector including a chimeric gene comprising a promoter operably linked to a nucleotide sequence substantially similar to any of SEQ ID NOS: 1, 3, 5, or 9, wherein said vector is capable of being stably transformed into a host cell. Further encompassed is a host cell including a vector comprising a chimeric gene comprising a promoter operatively linked to a nucleotide sequence substantially similar to any of SEQ ID NOS: 1, 3, 5, or 9, wherein said vector is capable of being stably transformed into a host cell and wherein said nucleotide sequence is expressible in said cell.

A preferred host cell according to the invention is either a prokaryotic or a eukaryotic cell. Most preferred is a host cell which is an *Escherichia coli* (*E. coli*), a yeast, or an insect cell.

In another embodiment, a novel polynucleotide having the sequence of SEQ ID NOS: 1, 3, 5, or 9 is overexpressed or underexpressed in an oomycete and effects on cell division, growth, nutrient uptake, reproduction, etc are measured.

Further embodied is a process of identifying compounds having antimicrobial activity including:

a) combining a protein comprising an amino acid sequence encoded by a nucleotide sequence substantially similar to a nucleotide sequence selected from the group consisting of SEQ ID NO: 1, SEQ ID NO: 3, SEQ ID NO: 5 and SEQ ID NO: 9 and a compound to be tested for the ability to bind to said protein, under conditions conducive to binding, b) selecting a compound identified in step (a) that is capable of binding said protein, c) applying the compound identified compound in step (b) to an oomycete or other microbe to test for antimicrobial activity, and d) selecting compounds having antimicrobial activity.

Further encompassed is a compound having antimicrobial activity identifiable by a process according to the invention. Further encompassed is a process of identifying an inhibitor of FtsZ activity having antimicrobial activity including:

a) combining a FtsZ-mt protein and a compound to be tested for the ability to inhibit the activity of said FtsZ-mt protein, under conditions conducive to such inhibition, b) selecting a compound identified in step (a) that is capable of inhibiting said FtsZ-mt protein activity, c) applying the compound identified in step (b) to a microbe such as an oomycete or α-proteobacterium to test for antimicrobial activity, and d) selecting compounds having antimicrobial activity.

In yet another embodiment, expression of the novel polynucleotide having the sequence of SEQ ID NOS: 1, 3, 5, or 9 in an oomycete is decreased and effects on cell division, growth, nutrient uptake, reproduction, etc is measured. Any inhibitor of FtsZ activity has potential as a fungicide for control of oomycete infection in higher plants.

A further embodiment of the invention is a compound having antimicrobial activity identifiable by a process according to the invention. Further encompassed is a method for suppressing the growth of an oomycete comprising, applying to said oomycete a compound that inhibits the activity of the amino acid sequence comprising an amino acid sequence encoded by a nucleotide sequence substantially similar to SEQ ID NOS: 1, 3, 5, or 9 in an amount sufficient to suppress the growth of said oomycete. In a preferred embodiment, the inhibiting compound is applied to *Phytophthora infestans*.

Further encompassed is a process of identifying compounds having antimicrobial activity including:

a) combining a protein selected from the group consisting of SEQ ID NO: 2, SEQ ID NO: 4 and SEQ ID NO: 10 and a compound to be tested for the ability to bind to said protein, under conditions conducive to binding, b) selecting a compound identified in step (a) that is capable of binding said protein, c) applying a compound identified in step (b) to a microbe such as an oomycete to test for antimicrobial activity, and d) selecting compounds having antimicrobial activity.

Further encompassed is a method of improving crops including, applying to a plant, plant part, plant seed, or surrounding soil a compound according to the invention having antimicrobial activity in an amount that inhibits the growth of undesirable microbes without significantly suppressing the growth of the plant or seed.

Furthermore, the invention can be used in a screening assay to identify inhibitors that are potential antimicrobials. Further embodied is a method which employs a virtual screen of inhibitors of the FtsZ function to be tested, including a) determining the 3-dimensional structure of an FtsZ-mt protein using a computer model, b) determining the 3-dimensional structure of an FtsZ-cp protein using a computer model, and c) testing chemicals for their ability to bind to FtsZ-mt, and not to FtsZ-cp, using a computer model.

The invention also provides methods for suppressing the growth of an oomycete or an α-proteobacterium including the step of applying to the oomycete or the α-proteobacterium a chemical that inhibits the naturally occurring FtsZ-mt activity in the oomycete or α-proteobacterium. In a related aspect, the present invention is directed to a method for selectively suppressing the growth of plant pests including, but not limited to, microbes such as those from the genera *Agrobacterium, Lagena, Peronophythora, Trachysphaera, Pythium, Phytophthora, Albugo, Peronospora, Plasmopora, Pseudoperonospora, Bremia, Bremiella* and *Basidiophora*, in a field containing a crop of planted crop seeds or plants, including the steps of:

a) optionally planting crops or crop; and b) applying to the crop plant, plant part, plant seed, or surrounding soil in the field an antimicrobial in amounts that inhibit naturally occurring FtsZ-mt activity in an oomycete or an α-proteobacterium without affecting FtsZ-cp activity in the plant plastid, wherein the antimicrobial suppresses the growth of microbes such as those from the genera *Lagena, Peronophythora, Trachysphaera, Pythium, Phytophthora, Albugo, Peronospora, Plasmopora, Pseudoperonospora, Bremia, Bremiella* and *Basidiophora* without significantly suppressing the growth of the crops.

A further aspect of the invention provides means to treat plant species including, but not limited to, potato, tomato, tobacco, oaks, coffee berry (Rhamnus sp.), squash, cotton, sorghum, peas, onion, melon, cucumber, peas, beets, watermelon, peppers, Port Orford Cedar, taro, apple, Brassica species, sweet potato (Ipomea), spinach, beans, grapevine, sunflower, hops, lettuce, violets, asters, soybeans, and cereals including maize, rice, barley, wheat, and rye, and the like.

In an alternate embodiment, the present invention provides means to treat fish infected with an oomycete, such as an oomycete from the genus *Saprolegnia*. The infected fish may be treated with a chemical that inhibits the naturally occurring FtsZ-mt activity in the oomycete. A fish may be treated by direct external or internal application of a compound identified by methods of the present invention, and/or may be treated by exposure to a compound identified by methods of the present invention in solution.

Recombinant Production of FtsZ and Uses Thereof. For recombinant production of FtsZ in a host organism, a nucleotide sequence encoding FtsZ protein is inserted into an expression cassette designed for the chosen host and introduced into the host, where it is recombinantly produced. The choice of specific regulatory sequences such as promoter, signal sequence, 5' and 3' untranslated sequences, and enhancer appropriate for the chosen host is within the scope of knowledge of one of skill in the art. The resultant molecule, containing the individual elements operably linked in proper reading frame, may be inserted into a vector capable of being transformed into the host cell. Suitable expression vectors and methods for recombinant production of proteins are well known for host organisms such as *E. coli*, yeast, and insect cells (see, e.g., Luckow and Summers (1988) *BioTechnol* 6: 47) and baculovirus expression vectors, e.g., those derived from the genome of *Autographa californica* nuclear polyhedrosis virus (AcMNPV).

In a preferred embodiment, the nucleotide sequence encoding a protein having FtsZ-mt activity is derived from an oomycete and most preferably from *P. infestans*. In a further preferred embodiment, the nucleotide sequence is identical or substantially similar to the nucleotide sequence set forth in any of SEQ ID NOS: 1, 3, 5, or 9, or encodes a protein having FtsZ-mt activity, whose amino acid sequence is identical or substantially similar to the amino acid sequence set forth in any of SEQ ID NOS: 2, 4 or 10.

The nucleotide sequence set forth in SEQ ID NO: 1 is a genomic sequence which encodes a *Phytophthora infestans* FtsZ-mt1 protein, whose amino acid sequence is set forth in SEQ ID NO:2. The genomic nucleotide sequence set forth in SEQ ID NO: 5 also encodes a FtsZ-mt2 protein containing 2 introns as determined by the "GT-AG" rule and amino acid sequence homology to known FtsZ proteins. The corresponding cDNA is set forth in SEQ ID NO: 3. SEQ ID NO: 9 shows the sequence of a full length cDNA corresponding to the FtsZ-mt2 genomic sequence. The corresponding protein sequence is shown as SEQ ID NO: 10. The FtsZ-mt2 protein (SEQ ID NO: 10) is predicted by TargetP (Emanuelsson et al. (2000) *J. Mol. Biol* 300:1005–1016) to be transported into the mitochondrion.

Recombinantly produced FtsZ-mt is isolated and purified using a variety of standard techniques. The actual techniques that may be used will vary depending upon the host organism used (see, e.g., chapter 16 of Ausubel, F. et al., "Current Protocols in Molecular Biology", pub. by John Wiley & Sons, Inc. (1994)).

Screening of Random Chemicals and Known Antimicrobials. Recombinantly produced FtsZ-mt proteins are useful for a variety of purposes. For example, they can be used in in vitro assays to screen known antimicrobial chemicals whose target has not been identified, to determine if they inhibit FtsZ-mt. Such in vitro assays may also be used as more general screens to identify chemicals that inhibit FtsZ protein function and that are therefore novel antimicrobial candidates. Alternatively, recombinantly produced FtsZ proteins may be used to elucidate the complex structure of these molecules and to further characterize their association with known inhibitors in order to rationally design new inhibitory antimicrobials as well as antimicrobial-tolerant forms of the enzymes.

Nucleotide sequences substantially similar to any of SEQ ID NOS: 1, 3, 5, or 9 and proteins substantially similar to SEQ ID NOS:2, 4 or 10 from any source, including microbial sources, can be used in the assays exemplified herein. Desirably, such nucleotide sequences and proteins are derived from oomycetes. More desirably, they are derived from *P. infestans.*

Novel technologies are being examined that can detect interactions between a protein and a ligand without regard to the biological function of the protein. A short description of three methods is presented, including fluorescence correlation spectroscopy, surface-enhanced laser desorption/ionization, and biacore technologies. Many more of these methods are currently being discovered, and some may be amenable to automated, large scale screening in light of this disclosure.

Fluorescence Correlation Spectroscopy (FCS) theory was developed in 1972 but only in recent years has the technology to perform FCS became available (Madge et al. (1972) *Phys Rev Lett,* 29: 705–708; Maiti et al. (1997) *Proc Natl Acad Sci USA,* 94: 11753–11757). FCS measures the average diffusion rate of a fluorescent molecule within a small sample volume. The sample size can be as low as 103 fluorescent molecules and the sample volume as low as the cytoplasm of a single bacterium. The diffusion rate is a function of the mass of the molecule and decreases as the mass increases. FCS can therefore be applied to protein-ligand interaction analysis by measuring the change in mass and therefore in diffusion rate of a molecule upon binding.

Surface-Enhanced Laser Desorption/Ionization (SELDI) was invented by Hutchens and Yip during the late 1980's (Hutchens and Yip (1993) *Rapid Comm Mass Spectrom* 7: 576–580). When coupled to a time-of-flight mass spectrometer (TOF), SELDI provides a means to rapidly analyze molecules retained on a chip. It can be applied to ligand-protein interaction analysis by covalently binding the target protein on the chip and analysis by MS of the small molecules retained by this protein (Worrall et al. (1998) *Anal Biochem* 70: 750–756).

Biacore relies on changes in the refractive index at the surface layer upon binding of a ligand to a protein immobilized on the layer. In this system, a collection of small ligands is injected sequentially in a 2–5 microliter cell with the immobilized protein. Binding is detected by surface plasmon resonance (SPR) by recording laser light refracting from the surface. In general, the refractive index change for a given change of mass concentration at the surface layer is practically the same for all proteins and peptides, allowing a single method to be applicable for any protein (Liedberg et al. (1983) *Sensors Actuators* 4: 299–304; Malmquist (1993) *Nature,* 361: 186–187).

Virtual Screens. Virtual screens are also possible based upon the structure of the proteins to be tested or upon the 3-dimensional structures determined by crystallography of recombinantly produced FtsZ-mt proteins. Alternatively, the 3-dimensional structures of FtsZ-mt proteins can be modeled on the computer utilizing the known 3-dimensional structure of the archaeon FtsZ. The model can then be used to virtually screen for chemicals which bind to the FtsZ-mts of the present invention. Chemicals which react at or near interaction surfaces are particularly good candidates because FtsZ proteins are known to interact with other protein molecules, including other FtsZ protein molecules, as part of their normal function during cell division.

Chemicals which react with the three-dimensional FtsZ-mt model will be further tested against a model of a FtsZ-cp protein. In order to be a good candidate for a specific microbial inhibitor, the test chemical must not bind the FtsZ-cp protein, in order to provide that there is no potential inhibition of plant growth. Such chemicals are also potential candidates as target-specific antimicrobials against pathogens in other higher eukaryotes including animals and humans.

Chemicals which bind to the FtsZ-mt model but not to the FtsZ-cp model are then selected as good candidates for potential specific inhibitors of oomycetes.

Potential targeting sites may be determined empirically and by any means known in the art. One strategy is to pinpoint sites which differ between oomycete mitochondrial forms of FtsZ and higher plant chloroplast forms of FtsZ. FIGS. 2, 2A–2D shows a comparison of the FtsZ-mt1 and FtsZ-mt2 protein sequences with other known FtsZ proteins. Differences between clusters of similar sequences can be determined by comparison of sequence alignments. Potential targeting sites are found at the following positions in the protein sequence: amino acid position 18, 30, 31, 62, 135, 142, 156–157, 159, 163, 189–190, 198, 210, 217, 223, 227, 236, 245, 251–252, 266, 271, 276, 287–289, 300, 302, and 306 (FIGS. 2, 2A–2D). These sites show differences in FtsZ protein sequences between the cluster for mitochondria from lower eukaryoltes and an α-proteobacteria, and the cluster for higher plant chloroplasts and cyanobacteria. Consequently, these sites represent a preferred embodiments for targeting with potntial inhibitors of FtsZ-mt function.

In vivo Inhibitor Assay. In one embodiment, a suspected antimicrobial, for example identified by in vitro or virtual screening, is applied to a microbe, preferably an oomycete, more preferably to *P. infestans* at various concentrations. After application of the suspected antimicrobial its effect, for example death or suppression of growth, is recorded.

Compounds active against oomycete FtsZ can be used to control the oomycete pathogens listed and combat the oomycete-caused diseases listed in Table I.

TABLE 1

Oomycete Pathogens of Economically Important Plant Species

| PATHOGEN | REPRESENTATIVE PLANT HOST(S) | REPRESENTATIVE DISEASES |
|---|---|---|
| | Order Pythiales | |
| *Lagena radicicola* | *Hordeum vulgare* (barley), *Triticum aestivum* (wheat), *Secale cereale* (rye) | Browning root rot |
| *Peronophythora litchii* | *Litchi* species (litchi) | Blossom blight, fruit rot |
| *Trachysphaera fructigena* | *Rhamnus californica* (coffee berry) | Mealy rot |
| *Pythium aphanidermatum* | *Cucurbita* species (squash), *Gossypium* species (cotton), *Glycine max* (soybean), *Nicotiana tobacum* (tobacco), *Lycopersicon esculentum* (tomato) | Damping off, root rot |
| *Pythium arrhenomanes* | *Zea mays* (corn), *Sorghum bicolor* (sorghum) | Damping off, root rot |
| *Pythium mamillatum* | *Pisum* species (peas), *Allium* species (onions), *Gossypium* species (cotton), *Cucumis* species (melons and cucumbers), *Zea mays* (corn) | Damping off, root rot |
| *Pythium splendens* | *Zea mays* (corn), and others | Cortical rot |
| *Pythium ultimum* | *Pisum* species (peas), *Beta* species (beets), *Citrullus lantus* (watermelon), *Glycine max* (soybean) | Damping off, root rot, fruit rot |
| *Phytophthora infestans* | *Solanum tuberosum* (potato) | Foliar blight |
| *Phytophthora capsici* | *Capsicum* species (peppers), *Citrullus lanatus* (watermelon), *Cucumis* species (melons and cucumbers) | Fruit rots |
| *Phytophthora lateralis* | *Chamaecyparis lawsoniana* (Port Orford Cedar) | Root disease |
| *Phytophthora colocasiae* | *Colocasia esculenta* (taro) | Leaf blight, rhizome rot |
| *Phytophthora syringae* | *Malus* species (apple) | Fruit rot |
| | Order Peronosporales | |
| *Albugo candida* | *Brassica* species (*cruciferous* plants) | White rust |
| *Albugo ipomoeae-panduratae* | *Ipomoea batatas* (sweet potato) | White rust |
| *Peronospora destructor* | *Allium cepa* (onion) | Downy mildew |
| *Peronospora farinosa* | *Beta* species (beets), *Spinacia oleracea* (spinach) | Downy mildew |
| *Peronospora hyoscyami* | *Nicotiana tobacum* (tobacco) | Downy mildew |
| *Peronospora manshurica* | *Glycine max* (soybean), *Pisum* species (peas), *Phaseolus* species (beans), *Vigna* species (beans) | Downy mildew |
| *Plasmopora viticola* | *Vitis vinifera* (grapevine) | Downy mildew |
| *Plasmopora halstedii* | *Helianthus* species (sunflower) | Downy mildew |
| *Pseudoperonospora cubensis* | *Cucurbita* species (squash) | Downy mildew |
| *Pseudoperonospora humuli* | *Humulus lupulus* (hops) | Downy mildew |
| *Bremia lactucae f.* sp. *Lactucae* | *Lactuca sativa* (lettuce) | Downy mildew |
| *Bremiella megasperma* | *Viola* species (violets) | Downy mildew |
| *Basidiophora entospora* | *Aster* species (asters) | Downy mildew |

EXAMPLES

Example 1

Isolation of genomic FtsZ sequences from *Phytophthora infestans*

FtsZ-mt1 (SEQ ID NO: 1) and FtsZ-mt2 (genomic) (SEQ ID NO: 5) were obtained from *P. infestans* genomic sequences by degenerate PCR using Platinum Taq (LTI, for hot start PCR) using the reaction conditions recommended by manufacturer (LTI). A 30 μl reaction contained 20 ng of *P. infestans* genomic DNA and 15 pmol each of the primers. One of two combinations of the primers (PI01A & PI03B or PI01A & PI06B; primers shown below) were used. The letter "I" in the primers shown below indicates that inosine is used at that site. The letter "Y" in primer PI01A (SEQ ID NO: 6) is used to indicate that T or C (a pyrimidine base) may be used at that site. The letter "R" in primer PI06B (SEQ ID NO: 8) is used to indicate that G or A (a purine base) may be used at that site.

PI01A
5'-AAYGCIGTIAAYAAYATGAT-3' (SEQ ID NO: 6)
PI03B
5'-GTICCIGTICCICCICCCAT-3' (SEQ ID NO: 7)
PI06B
5'-GTICKIACRTCIGCRAARTC-3' (SEQ ID NO: 8)

The PCR program was:

1) 94° C., 3 min.
2) 94° C., 15 sec
3) 52° C., 25 sec
4) 72° C., 45 sec

Steps 2-4 were repeated 34 times (total 35 thermal cycles)
5) 72° C., 15 min.

The annealing temperature used in step 3 was determined based on a preliminary temperature gradient experiment.

The PCR products were separated by agarose gel electrophoresis. Two products of 250 bp (for FtsZ-mt1) and 420 bp (FtsZ-mt2 (genomic)) from the reaction with the primer combination of PI01A (SEQ ID NO: 6) and PI03B (SEQ ID NO: 7), and one product of 600 bp (FtsZ-mt1) from the reaction with the primer combination of PI01A (SEQ ID NO: 6) and PI06B (SEQ ID NO: 8) were isolated from the gel.

The isolated PCR products were cloned into PCR2.1-TOPO vector using TOPO-TA cloning kit (Invitrogen) and the sequence of the insert sequences was determined. FtsZ-mt1 (SEQ ID NO: 1) does not have an intron. The deduced amino acid sequence for FtsZ-mt1 is shown in SEQ ID NO: 2. FtsZ-mt2 (genomic) (SEQ ID NO: 5) has two introns and the FtsZ-mt2 (genomic) cDNA (SEQ ID NO: 3) is the sequence artificially spliced based on the "GT-AG" rule and the amino acid sequence homology. The deduced amino acid sequence for FtsZ-mt2 (genomic) is shown in SEQ ID NO: 4.

Example 2

Isolation of a Full Length FtsZ-mt2 cDNA from *Phytophthora infestans*

A full length FtsZ-mt2 cDNA was isolated by searching a *P. infestans* EST sequence library prepared by Novartis Agribusiness Biotechnology Research, Inc.(NABR1). Clones identified by screening with FtsZ-specific probes were isolated, and the inserts of EST clones positive for FtsZ-mt2 were sequenced. FtsZ-mt2 (cDNA) (SEQ ID NO: 9) represents the complete cDNA sequence corresponding the FtsZ-mt2 (genomic) cDNA (SEQ ID NO: 3). The deduced amino acid sequence for FtsZ-mt2 (cDNA) is shown in SEQ ID NO: 10.

Example 3

Screening Methods for Inhibitors of FtsZ: Computer Modeling

The 3-dimensional structure of FtsZ-mt1 and FtsZ-mt2 (genomic and cDNA) and the chloroplast FtsZ (FtsZ-cp) will be determined by computer using a software program such as MolSoft™. Chemicals will be virtually screened to look for those which can bind to FtsZ-mt, but not to FtsZ-cp. Any chemicals which are capable of binding to FtsZ-mt, but not to FtsZ-cp are good candidates for specific inhibitors of FtsZ-mt and have potential as antimicrobial agents in methods of pest control. In addition, FtsZ proteins are known to interact with other proteins as part of their normal function during cell division. Consequently, chemicals that bind at or near interaction surfaces will make especially good candidates as potential antimicrobials.

FIGS. 2, 2A–2D shows a comparison of the FtsZ-mt1 and FtsZ-mt2 protein sequences with other known FtsZ proteins. Potential targeting sites are found at the following positions in the protein sequenc: amino acid position 18, 30, 31, 62, 135, 142, 156–157, 159, 163, 189–190, 198, 210, 217, 223, 227, 236, 245, 251–252, 266, 271, 276, 287–289, 300, 302, and 306. The indicated sites were well-clustered by homology with FtsZs from an (α)-proteobacteria and other mitochondrial forms, but well-separated from the cluster for the chloroplast forms and cyanobacterial FtsZs. Chemicals will be designed that can discriminate and recognize one of the amino acids in a given cluster. Such chemicals will only kill primitive eukaryotes having FtsZ-mt proteins, such as oomycetes, and some bacteria that have highly homologous FtsZ proteins, such as an α-proteobacterium, but will not affect other eukaryotes, including plants and animals.

The indicated residues were well conserved within the clusters which indicated a constraint to conserve the residue within this branch of phylogeny. Due to the constraint, if a chemical targets one of the residues listed above, it is likely that the oomycete pathogen will not easily develop resistance to that chemical because mutations in these positions would likely cause negative effects. Also, other oomycetes will also have the conserved residue. Thus, the chemical will be effective on a wide variety of microbial pathogens, not just *Phytophthora infestans*.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method of identifying compounds having antimicrobial activity comprising:

a) combining an oomycete FtsZ-mt protein having the amino acid sequence of SEQ ID NO:2, and a compound to be tested for an ability to bind to said polypeptide, under conditions conducive to binding, b) selecting a compound of step (a) that is capable of binding to said polypeptide, c) applying a compound of step (b) to a microbe to test for antimicrobial activity, and d) selecting a compound of step (c) having antimicrobial activity.

2. The method of claim 1, wherein said polypeptide is encoded by an isolated DNA molecule comprising a nucleotide sequence identical to the sequence of SEQ ID NO: 1.

3. The method of claim 1, wherein the microbe is an oomycete.

4. The method of claim 3, wherein the oomycete is *Phytophthora infestans*.

* * * * *